(12) United States Patent
Hyde et al.

(10) Patent No.: US 8,606,592 B2
(45) Date of Patent: *Dec. 10, 2013

(54) METHODS AND SYSTEMS FOR MONITORING BIOACTIVE AGENT USE

(75) Inventors: Roderick A. Hyde, Redmond, WA (US); Muriel Y. Ishikawa, Livermore, CA (US); Eric C. Leuthardt, St. Louis, MO (US); Royce A. Levien, Lexington, MA (US); Robert W. Lord, Seattle, WA (US); Mark A. Malamud, Seattle, WA (US); Elizabeth A. Sweeney, Seattle, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 96 days.

This patent is subject to a terminal disclaimer.

(21) Appl. No.: 12/217,620

(22) Filed: Jul. 7, 2008

(65) Prior Publication Data

US 2009/0271120 A1 Oct. 29, 2009

Related U.S. Application Data

(63) Continuation-in-part of application No. 12/217,509, filed on Jul. 3, 2008, and a continuation-in-part of application No. 12/214,547, filed on Jun. 19, 2008, and a continuation-in-part of application No. 12/157,989, filed on Jun. 13, 2008, and a continuation-in-part of application No. 12/157,922, filed on Jun. 13, 2008, and a continuation-in-part of application No. 12/157,160, filed on Jun. 6, 2008, and a continuation-in-part of application No. 12/156,949, filed on Jun. 5, 2008, and a continuation-in-part of application No. 12/156,440, filed on May 30, 2008, and a continuation-in-part of application No. 12/154,275, filed on May 21, 2008, and a continuation-in-part of application No. 12/152,266, filed on May 13, 2008, now abandoned, and a continuation-in-part of application No. 12/150,122, filed on Apr. 24, 2008.

(51) Int. Cl.
*G06Q 10/00* (2012.01)
*G06F 19/00* (2011.01)
*A61M 11/00* (2006.01)

(52) U.S. Cl.
USPC .......................... 705/2; 702/19; 128/200.16

(58) Field of Classification Search
USPC .......................................................... 705/2
See application file for complete search history.

(56) References Cited

U.S. PATENT DOCUMENTS 3,036,568 A  5/1962  Stark
4,570,640 A  2/1986  Barsa (Continued)

FOREIGN PATENT DOCUMENTS

WO  WO 2003/048789 A2  6/2003
WO  WO 2006/048417 A1  5/2006
WO  WO2007/016241  2/2007

OTHER PUBLICATIONS

Kris Bosworth, et al., A computer-Based Violence Prevention Intervention for Young Adolescents: A Pilot Study, Adolescence, Winter 1998, pp. 785-796, vol. 33, No. 132, Publisher: Libra Publishers, Inc., Published in: US.

(Continued)

*Primary Examiner* — Hiep V Nguyen

(57) ABSTRACT

Methods, computer program products, and systems are described that include accepting at least one indication of a bioactive agent use by an individual and/or assigning an artificial sensory experience to monitor at least one desired effect of the bioactive agent on the individual.

26 Claims, 48 Drawing Sheets

(56) References Cited

U.S. PATENT DOCUMENTS

| | | | |
|---|---|---|---|
| 4,734,585 A | 3/1988 | Owers | |
| 4,755,043 A | 7/1988 | Carter | |
| 4,973,149 A | 11/1990 | Hutchinson | |
| 4,974,729 A | 12/1990 | Steinnagel | |
| 5,135,752 A | 8/1992 | Snipes | |
| 5,277,188 A | 1/1994 | Selker | |
| 5,348,268 A | 9/1994 | Klein | |
| 5,463,564 A | 10/1995 | Agrafiotis et al. | |
| 5,577,981 A | 11/1996 | Jarvik | |
| 5,610,674 A | 3/1997 | Martin | |
| 5,645,072 A | 7/1997 | Thrall et al. | |
| 5,671,752 A | 9/1997 | Sinderby et al. | |
| 5,722,754 A | 3/1998 | Langner | |
| 5,724,983 A | 3/1998 | Selker et al. | |
| 5,725,472 A | 3/1998 | Weathers | |
| 5,822,726 A | 10/1998 | Taylor et al. | |
| 5,845,255 A | 12/1998 | Mayaud | |
| 5,846,086 A | 12/1998 | Bizzi et al. | |
| 5,891,049 A | 4/1999 | Cyrus et al. | |
| 5,919,141 A | 7/1999 | Money et al. | |
| 6,053,866 A | 4/2000 | McLeod | |
| 6,067,523 A | 5/2000 | Bair et al. | |
| 6,149,586 A | 11/2000 | Elkind | |
| 6,152,563 A | 11/2000 | Hutchinson et al. | |
| 6,186,145 B1 | 2/2001 | Brown | |
| 6,198,953 B1 | 3/2001 | Webster et al. | |
| 6,282,458 B1 | 8/2001 | Murayama et al. | |
| 6,314,384 B1 | 11/2001 | Goetz | |
| 6,315,719 B1 | 11/2001 | Rode et al. | |
| 6,334,778 B1 | 1/2002 | Brown | |
| 6,383,135 B1 | 5/2002 | Chikovani et al. | |
| 6,397,080 B1 | 5/2002 | Viktorsson et al. | |
| 6,421,650 B1 | 7/2002 | Goetz et al. | |
| 6,425,764 B1 | 7/2002 | Lamson | |
| 6,448,030 B1 | 9/2002 | Rust et al. | |
| 6,487,520 B1 | 11/2002 | Kurtzberg et al. | |
| 6,542,858 B1 | 4/2003 | Grass et al. | |
| 6,561,811 B2 | 5/2003 | Rapoza et al. | |
| 6,565,359 B2 | 5/2003 | Calhoun et al. | |
| 6,647,358 B2 | 11/2003 | Grass et al. | |
| 6,702,767 B1 | 3/2004 | Douglas et al. | |
| 6,807,492 B2 | 10/2004 | Oren et al. | |
| 6,826,498 B2 | 11/2004 | Birkner et al. | |
| 6,832,178 B1 | 12/2004 | Fernandez et al. | |
| 6,852,069 B2 | 2/2005 | Park | |
| 6,886,653 B1 | 5/2005 | Bellehumeur | |
| 6,909,359 B1 | 6/2005 | McGovern | |
| 6,947,790 B2 | 9/2005 | Gevins et al. | |
| 6,952,695 B1 | 10/2005 | Trinks et al. | |
| 6,968,375 B1 | 11/2005 | Brown | |
| 6,997,880 B2 | 2/2006 | Carlebach et al. | |
| 7,002,476 B2 | 2/2006 | Rapchak | |
| 7,033,025 B2 | 4/2006 | Winterbotham | |
| 7,039,878 B2 | 5/2006 | Auer et al. | |
| 7,044,911 B2* | 5/2006 | Drinan et al. | 600/300 |
| 7,049,103 B2 | 5/2006 | Ishiguro et al. | |
| 7,076,437 B1 | 7/2006 | Levy | |
| 7,084,874 B2 | 8/2006 | Kurzweil | |
| 7,144,680 B2 | 12/2006 | Park et al. | |
| 7,148,208 B2 | 12/2006 | Barkan et al. | |
| 7,161,579 B2 | 1/2007 | Daniel | |
| 7,177,675 B2 | 2/2007 | Suffin et al. | |
| 7,197,492 B2 | 3/2007 | Sullivan | |
| 7,198,044 B2* | 4/2007 | Trueba | 128/200.16 |
| 7,226,164 B2 | 6/2007 | Abourizk et al. | |
| 7,229,288 B2 | 6/2007 | Stuart et al. | |
| 7,245,956 B2 | 7/2007 | Matthews et al. | |
| 7,272,431 B2 | 9/2007 | McGrath | |
| 7,294,107 B2 | 11/2007 | Simon et al. | |
| 7,353,065 B2* | 4/2008 | Morrell | 607/45 |
| 7,461,651 B2 | 12/2008 | Brown | |
| 7,513,622 B2 | 4/2009 | Khaderi | |
| 7,575,865 B2 | 8/2009 | Leamon et al. | |
| 7,623,927 B2* | 11/2009 | Rezai | 607/45 |
| 7,890,340 B2 | 2/2011 | Abraham-Fuchs et al. | |
| 2001/0001144 A1 | 5/2001 | Kapp | |
| 2001/0010541 A1 | 8/2001 | Fernandez et al. | |
| 2002/0103428 A1 | 8/2002 | deCharms | |
| 2002/0128061 A1 | 9/2002 | Blanco | |
| 2003/0036683 A1 | 2/2003 | Kehr et al. | |
| 2003/0144884 A1 | 7/2003 | Mayaud | |
| 2003/0214630 A1 | 11/2003 | Winterbotham | |
| 2004/0078027 A1 | 4/2004 | Shachar | |
| 2004/0078239 A1 | 4/2004 | Dacosta | |
| 2004/0123667 A1 | 7/2004 | McGrath | |
| 2004/0172285 A1* | 9/2004 | Gibson | 705/2 |
| 2004/0196184 A1 | 10/2004 | Hollander et al. | |
| 2005/0021372 A1 | 1/2005 | Mikkelsen et al. | |
| 2005/0054942 A1 | 3/2005 | Melker et al. | |
| 2005/0065813 A1 | 3/2005 | Mishelevich et al. | |
| 2005/0086077 A1 | 4/2005 | Forman | |
| 2005/0124878 A1 | 6/2005 | Sharony | |
| 2005/0165115 A1 | 7/2005 | Murphy et al. | |
| 2005/0197654 A1 | 9/2005 | Edman et al. | |
| 2005/0240084 A1 | 10/2005 | Morice et al. | |
| 2005/0277911 A1 | 12/2005 | Stewart et al. | |
| 2006/0031099 A1 | 2/2006 | Vitello et al. | |
| 2006/0058694 A1 | 3/2006 | Clark et al. | |
| 2006/0059145 A1 | 3/2006 | Henschke et al. | |
| 2006/0062852 A1 | 3/2006 | Holmes | |
| 2006/0084877 A1 | 4/2006 | Ujhazy et al. | |
| 2006/0111644 A1 | 5/2006 | Guttag et al. | |
| 2006/0161408 A1 | 7/2006 | Bachman et al. | |
| 2006/0161456 A1 | 7/2006 | Baker et al. | |
| 2006/0183980 A1 | 8/2006 | Yang | |
| 2006/0235724 A1 | 10/2006 | Rosenthal | |
| 2006/0241718 A1* | 10/2006 | Tyler et al. | 607/45 |
| 2006/0247489 A1 | 11/2006 | Carbis et al. | |
| 2006/0252761 A1 | 11/2006 | Davis et al. | |
| 2006/0265253 A1 | 11/2006 | Rao et al. | |
| 2007/0016265 A1 | 1/2007 | Davoodi et al. | |
| 2007/0067186 A1 | 3/2007 | Brenner et al. | |
| 2007/0088404 A1 | 4/2007 | Wyler et al. | |
| 2007/0112624 A1 | 5/2007 | Jung et al. | |
| 2007/0123783 A1 | 5/2007 | Chang | |
| 2007/0136093 A1 | 6/2007 | Rankin et al. | |
| 2007/0172814 A1 | 7/2007 | Li | |
| 2007/0179534 A1 | 8/2007 | Firlik et al. | |
| 2008/0045832 A1 | 2/2008 | McGrath | |
| 2008/0097167 A1 | 4/2008 | Yudkovitch et al. | |
| 2008/0125978 A1 | 5/2008 | Robson et al. | |
| 2008/0132383 A1 | 6/2008 | Einav et al. | |
| 2008/0139870 A1 | 6/2008 | Gliner et al. | |
| 2008/0139902 A1 | 6/2008 | Kotulla et al. | |
| 2008/0167571 A1 | 7/2008 | Gevins | |
| 2008/0172044 A1 | 7/2008 | Shelton | |
| 2008/0212847 A1 | 9/2008 | Davies et al. | |
| 2008/0221847 A1 | 9/2008 | Fenetteau | |
| 2008/0226730 A1 | 9/2008 | Schmitke et al. | |
| 2008/0243544 A1 | 10/2008 | Cafer | |
| 2008/0275731 A1 | 11/2008 | Rao et al. | |
| 2008/0278682 A1 | 11/2008 | Huxlin et al. | |
| 2008/0305518 A1 | 12/2008 | Klausen et al. | |
| 2009/0171697 A1 | 7/2009 | Glauser et al. | |
| 2009/0306741 A1* | 12/2009 | Hogle et al. | 607/54 |
| 2009/0312817 A1 | 12/2009 | Hogle et al. | |
| 2010/0015184 A1 | 1/2010 | Tuel | |
| 2010/0163027 A1 | 7/2010 | Hyde et al. | |
| 2010/0168525 A1 | 7/2010 | Hyde et al. | |
| 2010/0168602 A1 | 7/2010 | Hyde et al. | |
| 2010/0324874 A9 | 12/2010 | Bangs et al. | |

OTHER PUBLICATIONS

M.R. Smith, et al., A Data Extrapolation Algorithm Using a Complex Domain Neuralnetwork, Circuits and Systems II: Analog and Digital Signal Processing, IEEE Transactions on, Feb. 1997, pp. 143-147, vol. 44, No. 2.

Max Bayard, et al., Alcohol Withdrawal Syndrome, American Family Physician, Mar. 15, 2004, pp. 1443-1450, vol. 69, Published in: US.

Hunter G. Hoffman, et al., Analgesic Effects of Opioids and Immersive Virtual Reality Distraction: Evidence from Subjective and Functional Brain Image Assessments, Anesthesia & Analgesia, 2007, pp. 1776-1783, vol. 105, Published in: US.

(56) References Cited

OTHER PUBLICATIONS

D. Shaw, et al., Anxiolytic Effects of Lavender Oil Inhalation on Open-Field Behaviour in Rats, Phytomedicine, Mar. 19, 2007, pp. 613-620, vol. 14.

Laurent Jeanpierre, et al., Automated Medical Diagnosis with Fuzzy Stochastic Models: Monitoring Chronic Diseases, Acta Biotheoretica, 2004, pp. 291-311, vol. 52, No. 4, Publisher: Springer.

Xueliang Huo, et al., A Wireless Pharmaceutical Compliance Monitoring System Based on Magneto-Inductive Sensors, Sensors Journal, IEEE, Dec. 2007, pp. 1171-1719, vol. 7, No. 12, Published in: US.

Barbara Ortutay, Brain-Reading Headset to Sell for $299, Feb. 20, 2008, Publisher: Associated Press, Published in: US.

E. Grossman, et al., Breathing-Control lowers Blood Pressure, Journal of Human Hypertension, Apr. 2001, pp. 263-269, vol. 15, No. 4, Publisher: Nature Publishing Group.

Jennifer Vasterling, et al., Cognitive Distraction and Relaxation Training for the Control of Side Effects Due to Cancer Chemotherapy, Journal of Behavioral Medicine, Feb. 1993, pp. 65-80, vol. 16, No. 1, Publisher: Springer Netherlands.

Robert E.L. Faris, Cultural Isolation and the Schizophrenic Personality, The American Journal of Sociology, Sep. 1934, pp. 155-164, vol. 40, No. 2, Publisher: University of Chicago Press, Published in: US.

Sandra L. Siedliecki, et al., Efect of Music on power, pain, Depression, and Disability, Journal of Advanced Nursing, Jan. 13, 2006, pp. 553-562, vol. 54, Publisher: Blackwell Publishing, Published in: US.

Maura Paul-Labrador, et al., Effects of a Randomized Controlled Trail of Transcendental Meditation on Components of the Metabolic Syndrome in Subjects With Coronary Heart Disease, Arch Intern Med, Jun. 12, 2006, pp. 1218-1224, vol. 166, Publisher: American Medical Society, Published in: US.

Igor Knez, Effects of Colour of Light on Nonvisual Psychological Processes, Jun. 2001, pp. 201-208, vol. 21, No. 2, Publisher: Journal of Environmental Psychology, Published in: US.

E. Glenn Schellenberg, et al., Exposure to Music and Cognitive Performance: Tests of Children and Adults, Psychology of Music, 2007, pp. 5-19, vol. 35, Published in: Canada.

Leonid Skorin, Jr., How to Diagnose and Manage Headaches, Review of Optometry, Nov. 1999, pp. 73-76, vol. 136, Published in: US.

Dale A. Lawrence, et al., Human Perception of Friction in Haptic Interfaces, Proc. ASME Dynamic Systems and Control Division, Nov. 1998, pp. 287-294, vol. 64, Published in: US.

Peter Clarke, IBEC Has a Brain Wave: Feed EEG Emotion Back Into Games, EE Times online, Nov. 1, 2007, Publisher: http://www.eetimes.eu/design/202801063.

F.J. Canadas-Quesada, et al., Improvement of Perceived Stiffness Using Auditory Stimuli in Haptic Virtual Reality, IEEE Melecon, May 16-19, 2006, Published in: Benalmadena, Spain.

J.N. Cohn, Introduction to Surrogate Markers, Circulation, 2004, pp. IV20-IV21, vol. 109, Publisher: American Heart Association, Published in: US.

Kuan Zhang, et al., Measurement of Human Daily Physical Activity, Obesity Research, Jan. 1, 2003, pp. 33-40, vol. 11, No. 1, Published in: US.

Sander Greenland, et al., Methods for Trend Estimation from Summarized Dose-Response Data, with Applications to Meta-Analysis, American Journal of Epidemiology, 1992, pp. 1301-1309, vol. 135, No. 11, Published in: US.

Russell N. Carney, et al., Mnemonic Instruction, With a Focus on Transfer, Dec. 2000, pp. 783-790, vol. 92, Publisher: Journal of Educational Psychology, Published in: US.

Fernando Patolsky, et al., Nanowire Sensors for Medicine and the Life Sciences, Future Medicine, Jun. 2006, pp. 51-65, vol. 1, No. 1, Published in: US.

M.R. Basso, Jr., Neurobiological Relationships Between Ambient Lighting and the Startle Response to Acoustic Stress in Humans, Sep. 2001, pp. 147-157, vol. 110, No. 3-4, Publisher: International Journal of Neuroscience, Published in: US.

New Horizons of Nerve Repair: Biomedical Engineer Trips Up Proteins in Nerve Regeneration System, Science Daily, Jul. 26, 2002, Publisher: http:www.sciencedaily.com/releases/2002/07/020725082253.htm, Published in: US.

New Mini-Sensor May Have Biomedical and Security Applications, Physorg.com, Nov. 1, 2007, Publisher: http://www.physorg.com/news113151078.html, Published in: US.

Luc Marlier, et al., Olfactory Stimulation Prevents Apnea in Premature Newborns, Pediatrics, Jan. 3, 2005, pp. 83-88, vol. 115, No. 1, Published in: US.

T. Green, et al., PC-Based Medical Data Acquisition and Analysis, 1995, p. 159 Publisher: 8th IEEE Symposium on Computer-Based Medical Systems (CBMS '95), Published in: US.

Neda Gould, et al., Performance on a Virtual Reality Spatial Memory Navigation Task in Depressed Patients, American Journal of Psychiatry, Mar. 10, 2007, pp. 516-519, vol. 165, Published in: US.

Phosphodiesterase Isoenzymes as Pharmacological Targets in the Treatment of Male Erectile Dysfunction, World Journal of Urology, Feb. 2001, pp. 14-22, vol. 19, No. 1, Publisher: Springer Berlin/Heidelberg.

JM Jokiniitty, et al., Prediction of Blood Pressure Level and Need for Antihypertensive Medication: 10 Years of Follow-up, J. Hypertension, Jul. 2001, pp. 1193-1201, vol. 19, No. 7.

K. Yamada, et al., Prediction of Medication Noncompliance in Outpatients with Schizophrenia: 2-year follow-up study, Psychiatry Research, 2004, pp. 61-69, vol. 141, No. 1.

G. Parker, et al., Prediction of Response to Antidepressant Medication by a Sign-Based Index of Melancholia, Australian and New Zealand Journal of Psychiatry, 1993, pp. 56-61, vol. 27, No. 1.

Kozarek, et al., Prospective Trial using Virtual Vision as Distraction Technique in Patients Undergoing Gastric Laboratory Procedures, Gastroenterology Nursing, Jan. 1997, pp. 12-14, vol. 20, No. 1, Published in: US.

Jan A. Staessen, et al., Randomised Double-Blind Comparison of Placebo and Active Treatment for Older Patients Wtih Isolated Systolic Hypertensio, The Lancet, Sep. 13, 1997, pp. 757-764, vol. 350, No. 9080.

Axelrod, et al., Smoke and Mirrors: Gathering User Requirements for Emerging Affective Systems, Jun. 10, 2004, pp. 323-328, vol. 1, Publisher: 26th International Conference on Information Technology Interfaces, 2004.

Alan G. Sanfey, Social Decision-Making: Insights from Game Theory and Neuroscience, Science Magazine, Oct. 26, 2007, pp. 598-602, vol. 318, No. 5850, Published in: US.

Something in the Way He Moves, The Economist, Sep. 27, 2007, Publisher: http://www.economist.com/science/PrinterFriendly.cfm?story_id=9861412, Published in: US.

Raymond W. Lam, et al., The Can-SAD Study: A Randomized Controlled Trial of the Effectiveness of Light Therapy and Fluoxetine in Patients With, May 2006, pp. 805-812, vol. 163, Publisher: American Journal of Psychiatry, Published in: US.

F. Joseph McClernon, et al., The Effects of Controlled Deep Breathing on Smoking Withdrawal Symptoms in Dependent Smokers, ScienceDirect, Jun. 2004, pp. 765-772, vol. 29, No. 4, Publisher: Elsevier Ltd., Published in: US.

Jin-Lain Ming, et al., The Efficacy of Acupressure to Prevent Nausea and Vomiting in Post-Operative Patients, Joumal of Advanced Nursing, Aug. 2002, pp. 343-351, vol. 39, No. 4, Published in: US.

Elizabeth Von Muggenthaler, The Felid Purr: A Bio-Mechanical Healing Mechanism, Sep. 18, 2006, Publisher: 12th International Conference on Low Frequency Noise and Vibration and its Control, Published in: Bristol, UK.

De Matthews, et al., Using and Understanding Medical Statistics, S. Karger Basel AG, 2007, pp. 111-127, Published in: US.

Shelley Wiechman Askay, Using Hypnosis for Spinal Cord Injury Pain Management, SCI Forum Report, Sep. 11, 2007, Publisher: http://sci.washington.edu/info/forums/reports/hypnosis_for_sci_pain.asp, Published in: US.

Video Game May Help Detect Depression, New Scientist, Mar. 10, 2007, p. 18, No. 2594, Published in: US.

Matthew M. Kurtz, et al., A Virtual Reality Apartment as a Measure of Medication Management Skills in Patients with Schizophrenia: A

(56) References Cited

OTHER PUBLICATIONS

Pilot Study, Schizophrenia Bulletin, 2007, pp. 1162-1170, vol. 33, No. 5, Publisher: Oxford University Press, Published in: US.
Virtual Reality Medical Center, Publisher: http://www.vrphobia.com/, Published in: US, printed on Mar. 4, 2008.
Virtual Reality Pain Reduction, Human Interface Technology Lab (HITL), Apr. 18, 2008, pp. 1-3, Publisher: http://hitl.washington.edu/projects/vrpain/, Published in: US.
Hunter G. Hoffman, Virtual-Reality Therapy, Scientific American, Jul. 26, 2004, pp. 60-65, Published in: US.
Albert Rizzo, et al., Virtual Therapeutic Environments with Haptics: An Interdisciplinary Approach for Developing Post-Stroke Rehabilitation S, CPSN 2005, Jun. 20-23, 2005, pp. 70-76, Publisher: Proceedings of the 2005 International Conference on Computers for People with Special needs, Published in: Las Vegas.
Alessandra Gorini, et al., Virtual Worlds, Real Healing, Science, Dec. 7. 2007, p. 1549, vol. 318, No. 5856, Publisher: AAAS, Published in: US.
J.A. Spencer, et al., White Noise and Sleep Induction, Archives of Disease in Childhood, 1990, pp. 135-137, vol. 65, Publisher: BMJ Publishing Group, Published in: London.
U.S. Appl. No. 12/315,366, Hyde et al.
U.S. Appl. No. 12/315,072, Hyde et al.
U.S. Appl. No. 12/290,456, Hyde et al.
U.S. Appl. No. 12/290,227, Hyde et al.
U.S. Appl. No. 12/287,886, Hyde et al.
U.S. Appl. No. 12/287,686, Hyde et al.
U.S. Appl. No. 12/286,751, Hyde et al.
U.S. Appl. No. 12/286,730, Hyde et al.
U.S. Appl. No. 12/283,742, Hyde et al.
U.S. Appl. No. 12/283,619, Hyde et al.
U.S. Appl. No. 12/229,612, Hyde et al.
U.S. Appl. No. 12/229,531, Hyde et al.
U.S. Appl. No. 12/220,706, Hyde et al.
U.S. Appl. No. 12/218,627, Hyde et al.
U.S. Appl. No. 12/218,503, Hyde et al.
U.S. Appl. No. 12/214,547, Hyde et al.
U.S. Appl. No. 12/157,989, Hyde et al.
Harland, C.J. et al.; "Electric potential probes—new directions in the remote sensing of the human body"; Measurement Science and Technology; bearing a date of 2002; pp. 163-169; vol. 13; Institute of Physics Publishing.
Harland, C.J. et al.; "High Resolution Ambulatory Electrocardiographic Monitoring Using Wrist-Mounted Electric Potential Sensors"; Measuring Science and Technology; bearing a date of May 23, 2003; pp. 923-928; vol. 14; IOP Publishing Ltd.
Harland, C.J. et al.; "Remote Detection of Human Electroencephalograms Using Ultrahigh Input Impedance Electric Potential Sensors"; Applied Physics Letters; bearing a date of Oct. 21, 2002; pp. 3284-3286; vol. 81, No. 17; American Institute of Physics.
Morishita, S. et al.; "Induction of Mania in Depression by Paroxetine"; Human Psychopharmacol; bearing a date of Oct. 2003; pp. 565-568; vol. 18, No. 7; Dept. of Psychiatry, Kawasaki Medical School [Abstract Only].
Piquepaille, Roland; "Virtual Reality Helps Diagnose Heart Defects"; bearing a date of Dec. 28, 2005; 2008 CNET Networks, Inc.
Prance, R.J. et al.; "Adaptive Electric Potential Sensors for Smart Signal Acquisition and Processing"; Journal of Physics: Conference Series 76; Sensors and their Applications XIV (SENSORS07); bearing a date of 2007; pp. 1-5; IOP Publishing Ltd.
Sulaiman, S. et al.; "Human Motion Analysis Using Virtual Reality"; Research and Development, 2007; SCOReD 2007; 5$^{th}$ Student Conference; bearing a date of Dec. 11-12, 2007; pp. 1-4; IEEE; published in Selangor, Malaysia [Abstract Only].
"Virtual Reality Games Used to Distract Young Burn Victims From Pain and Anxiety"; Medical News Today; bearing a date of Sep. 29, 2007; p. 1; located at http://www.medicalnewstoday.com/articles/84055.php.
"Virtual-Reality Video Game Helps Link Depression to Specific Brain Area"; ScienceDaily; bearing a date of Mar. 2, 2007; p. 1; located at http://www.sciencedaily.com/releases/2007/03/070301100807.htm: NIH (National Institute of Mental Health).
Yoshino, Kohzoh et al.; "An Algorithm for Detecting Startle State Based on Physiological Signals"; ScienceDirect; bearing a date of 2006; pp. 1-3; located at http://www.sciencedirect.com/science?_ob=ArticleURL&_udi=B6V5S-4M3BCCB-1&_user=10&_coverDate=03%2F31%2F2007&_alid=918001417&_rdoc=2&_fmt=high&_orig=search&_edi=5794&_sort=d&_docanchor=&view=c&_ct=5&_acct=C000050221&_version=1&_urlVersion=0&_userid=10&md5=bc77a78ef5a694a6ecf4dc397676f14f; Elsevier B.V. [Abstract Only].
U.S. Appl. No. 12/584,200, Leuthardt et al.
U.S. Appl. No. 12/584,129, Leuthardt et al.
U.S. Appl. No. 12/462,404, Leuthardt et al.
U.S. Appl. No. 12/462,344, Leuthardt et al.
U.S. Appl. No. 12/462,197, Leuthardt et al.
U.S. Appl. No. 12/462,129, Leuthardt et al.
U.S. Appl. No. 12/460,327, Leuthardt et al.
U.S. Appl. No. 12/460,252, Leuthardt et al.
U.S. Appl. No. 12/459,623, Leuthardt et al.
U.S. Appl. No. 12/459,493, Leuthardt et al.
U.S. Appl. No. 12/459,386, Leuthardt et al.
U.S. Appl. No. 12/459,287, Leuthardt et al.
U.S. Appl. No. 12/459,195, Leuthardt et al.
U.S. Appl. No. 12/459,029, Leuthardt et al.
U.S. Appl. No. 12/455,308, Leuthardt et al.
U.S. Appl. No. 12/455,148, Leuthardt et al.
U.S. Appl. No. 12/387,961, Leuthardt et al.
Barrientos, Ruth M. et al.; "Memory for context is impaired by injecting anisomycin into dorsal hippocampus following context exploration"; Behavioural Brain Research; bearing a date of Aug. 21, 2002; pp. 299-306; vol. 134, Issues 1-2; Elsevier Science B.V. (abstract only).
Grollman, Arthur P.; "Inhibitors of Protein Biosynthesis"; The Journal of Biological Chemistry; bearing a date of Jul. 10, 1967; pp. 3266-3233; vol. 242, No. 13.
Bonson, Katherine R.; "Hallucinogenic Drugs"; Encyclopedia of Life Sciences; bearing a date of 2001; pp. 1-7; Nature Publishing Group.
McKendree-Smith et al.; "Self-Administered Treatments for Depression: A Review"; Journal of Clinical Psychology; bearing a date of Mar. 2003; pp. 275-288; vol. 59, No. 3; Wiley Periodicals, Inc.
Pampallona et al; "Combined Pharmacotherapy and Psychological Treatment for Depression: A Systematic Review"; Arch Gen Psychiatry; bearing a date of Jul. 2004; pp. 714-719; vol. 61; American Medical Association.
"Seromycin-cycloserine capsule"; Physician's Desk Reference Digital Drug Database; bearing a revision date of Jun. 2007; pp. 1-5; PDR Network, LLC.
Silva, Alcino J. et al.; "Creb and Memory"; Annu. Rev. Neurosci.; 1998; pp. 127-137; vol. 21; Annual Reviews Inc.
Difede, Joann, Ph.D. et al.; "Virtual Reality Exposure Therapy for World Trade Center Post-traumatic Stress Disorder: A Case Report"; CyberPsychology & Behavior; 2002; pp. 529-535; vol. 5, No. 6; CyberPsychology & Behavior.
Hollifield, Michael, MD et al.; "Integrating Therapies for Anxiety Disorders"; Psychiatric Annals; May 2006; pp. 329-338; vol. 36, No. 5.
Kuzma, John M., MD et al.: "Integrating Pharmacotherapy and Psychotherapy in the Management of Anxiety Disorders"; Current Psychiatry Reports; 2004; pp. 268-273; vol. 6; Current Science Inc.
Vaiva, Guillaume et al.; "Immediate Treatment with Propranolol Decreases Posttraumatic Stress Disorder Two Months after Trauma"; Biological Psychiatry; 2003; pp. 947-949; vol. 54; Society of Biological Psychiatry.
Davis, Michael et al.; "Combining Pharmacotherapy With Cognitive Behavioral Therapy: Traditional and New Approaches"; Journal of Traumatic Stress; bearing a date of Oct. 2006; pp. 571-581; vol. 19, No. 5; InterScience.

(56) References Cited

OTHER PUBLICATIONS

IEEE 100: The Authoritative Dictionary of IEEE Standards Terms, Seventh Edition; The Institute of Electrical and Electronics Engineering Press.

Munjack, Dennis J. et al.; "Alprazolam, Propranolol, and Placebo in the Treatment of Panic Disorder and Agoraphobia with Panic Attacks"; Journal of Clinical Psychopharmacology; bearing a date of 1989; pp. 22-27; vol. 9, No. 1; Williams and Wilkins Co.

Ressler, Kerry J. et al.; "Cognitive Enhancers as Adjuncts to Psychotherapy Use of D-Cycloserine in Phobic Individuals to Facilitate Extinction of Fear"; bearing a date of Nov. 2004; pp. 1136-1144; vol. 61; Arch Gen Psychiatry.

Rothbaum, Barbara O. et al.; "Applying Learning Principles to the Treatment of Post-Trauma Reactions"; Annals New York Academy of Sciences; bearing a date of 2003; pp. 112-121; vol. 1008; New York Academy of Sciences.

Wiederhold, Brenda K.; "The Use of Virtual Reality Technology in the Treatment of Anxiety Disorders"; Information Technologies in Medicine; bearing a date of 2001; pp. 19-37; vol. II; John Wiley & Sons, Inc.

"Alter" Excerpt from The Merriam-Webster English Dictionary; Printed on Jul. 8, 2013; total of 4 pages; Merriam-Webster Incorporated.

IEEE 100: The Authoritative Dictionary of IEEE Standards Terms, Seventh Edition; The Institute of Electrical and Electronics Engineering Press; Dec. 2000; 10 pages; ISBN 0-7381-2601-2; The Institute of Electrical and Electronics Engineers, Inc.; New York, NY.

Lehrner et al.; "Ambient odors of orange and lavender reduce anxiety and improve mood in a dental office"; Physiology & Behavior; Apr. 27, 2005; pp. 92-95; vol. 86; Elsevier Inc.

Banos et al.; "Virtual Reality Treatment of Flying Phobia"; IEEE Transactions on Information Technology in Biomedicine; Bearing a date of Sep. 2002; pp. 206-212; vol. 6, No. 3; IEEE.

Coelho et al.; "Research Article: Deconstructing Acrophobia: Physiological and Psychological Precursors to Developing a Fear of Heights"; Depression and Anxiety; Bearing a date of Apr. 8, 2010; pp. 864-870; vol. 27; Wiley-Liss, Inc.

Mueller et al.; "Noradrenergic Modulation of Extinction Learning and Exposure Therapy"; Behavioural Brain Research; Bearing a date of Dec. 1, 2009; pp. 1-11; vol. 208; Elsevier B.V.

Rothbaum et al.; "A Controlled Study of Virtual Reality Exposure Therapy for the Fear of Flying"; Journal of Consulting and Clinical Psychology; Bearing a date of May 4, 2000; pp. 1020-1026; vol. 68, No. 6; American Psychological Association, Inc.

Van Gerwen et al.; "People Who Seek Help for Fear of Flying: Typology of Flying Phobics"; Behavior Therapy; Bearing a date of Mar. 11, 1997; pp. 237-251; vol. 28; Association for Advancement of Behavior Therapy.

* cited by examiner

METHODS AND SYSTEMS FOR MONITORING BIOACTIVE AGENT USE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of United States Patent Application entitled COMBINATION TREATMENT SELECTION METHODS AND SYSTEMS, naming Roderick A. Hyde; Muriel Y. Ishikawa; Eric C. Leuthardt; Royce A. Levien; Robert W. Lord; Mark A. Malamud; Elizabeth A. Sweeney; Lowell L. Wood, Jr.; and Victoria Y. H. Wood as inventors, filed Apr. 24, 2008, application Ser. No. 12/150,122, which is currently co-pending, or is an application of which a currently co-pending application is entitled to the benefit of the filing date.

For purposes of the USPTO extra-statutory requirements, the present application constitutes a continuation-in-part of United States Patent Application entitled COMBINATION TREATMENT MODIFICATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed May 13, 2008 now abandoned, application Ser. No. 12/152,266.

For purposes of the USPTO extra-statutory requirements, the present application constitutes a continuation-in-part of United States Patent Application entitled COMBINATION TREATMENT ALTERATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed May 21, 2008, application Ser. No. 12/154,275, which is currently co-pending, or is an application of which a currently co-pending application is entitled to the benefit of the filing date.

For purposes of the USPTO extra-statutory requirements, the present application constitutes a continuation-in-part of United States Patent Application entitled COMBINATION THERAPEUTIC PRODUCTS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed May 30, 2008, application Ser. No. 12/156,440, which is currently co-pending, or is an application of which a currently co-pending application is entitled to the benefit of the filing date.

For purposes of the USPTO extra-statutory requirements, the present application constitutes a continuation-in-part of United States Patent Application entitled SIDE EFFECT AMELIORATING COMBINATION THERAPEUTIC PRODUCTS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 5, 2008, application Ser. No. 12/156,949, which is currently co-pending, or is an application of which a currently co-pending application is entitled to the benefit of the filing date.

For purposes of the USPTO extra-statutory requirements, the present application constitutes a continuation-in-part of United States Patent Application entitled COMBINATION TREATMENT MODIFICATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 6, 2008, application Ser. No. 12/157,160, which is currently co-pending, or is an application of which a currently co-pending application is entitled to the benefit of the filing date.

For purposes of the USPTO extra-statutory requirements, the present application constitutes a continuation-in-part of United States Patent Application entitled COMBINATION TREATMENT SELECTION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 13, 2008, application Ser. No. 12/157,922, which is currently co-pending, or is an application of which a currently co-pending application is entitled to the benefit of the filing date.

For purposes of the USPTO extra-statutory requirements, the present application constitutes a continuation-in-part of United States Patent Application entitled COMBINATION TREATMENT MODIFICATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 13, 2008, application Ser. No. 12/157,989, which is currently co-pending, or is an application of which a currently co-pending application is entitled to the benefit of the filing date.

For purposes of the USPTO extra-statutory requirements, the present application constitutes a continuation-in-part of United States Patent Application entitled COMBINATION TREATMENT ALTERATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 19, 2008, application Ser. No. 12/214,547, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR MONITORING BIOACTIVE AGENT USE, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jul. 3, 2008, application Ser. No. 12/217,509, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

This description relates to methods and systems for combining medicine with an artificial sensory experience.

SUMMARY

In one aspect, a method includes but is not limited to accepting at least one indication of a bioactive agent use by an individual and assigning an artificial sensory experience to monitor at least one desired effect of the bioactive agent on the individual. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to means for accepting at least one indication of a bioactive agent use by an individual and means for assigning an artificial sensory experience to monitor at least one desired effect of the bioactive agent on the individual. In addition to the foregoing, other method aspects are described in the claims, drawings, and text forming a part of the present disclosure.

In one aspect, a system includes but is not limited to circuitry for accepting at least one indication of a bioactive agent use by an individual and circuitry for assigning an artificial sensory experience to monitor at least one desired effect of the bioactive agent on the individual. In addition to the foregoing, other method aspects are described in the claims, drawings, and text forming a part of the present disclosure.

In one aspect, a computer program product includes but is not limited to a signal-bearing medium bearing one or more instructions for accepting at least one indication of a bioactive agent use by an individual and one or more instructions for assigning an artificial sensory experience to monitor at least one desired effect of the bioactive agent on the individual. In addition to the foregoing, other method aspects are described in the claims, drawings, and text forming a part of the present disclosure.

In one aspect, a system includes but is not limited to a computing device and instructions that when executed on the computing device cause the computing device to accept at least one indication of bioactive agent use by an individual and assign an artificial sensory experience to monitor at least one desired effect of the bioactive agent on the individual. In addition to the foregoing, other method aspects are described in the claims, drawings, and text forming a part of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

DETAILED DESCRIPTION

Figure 1:
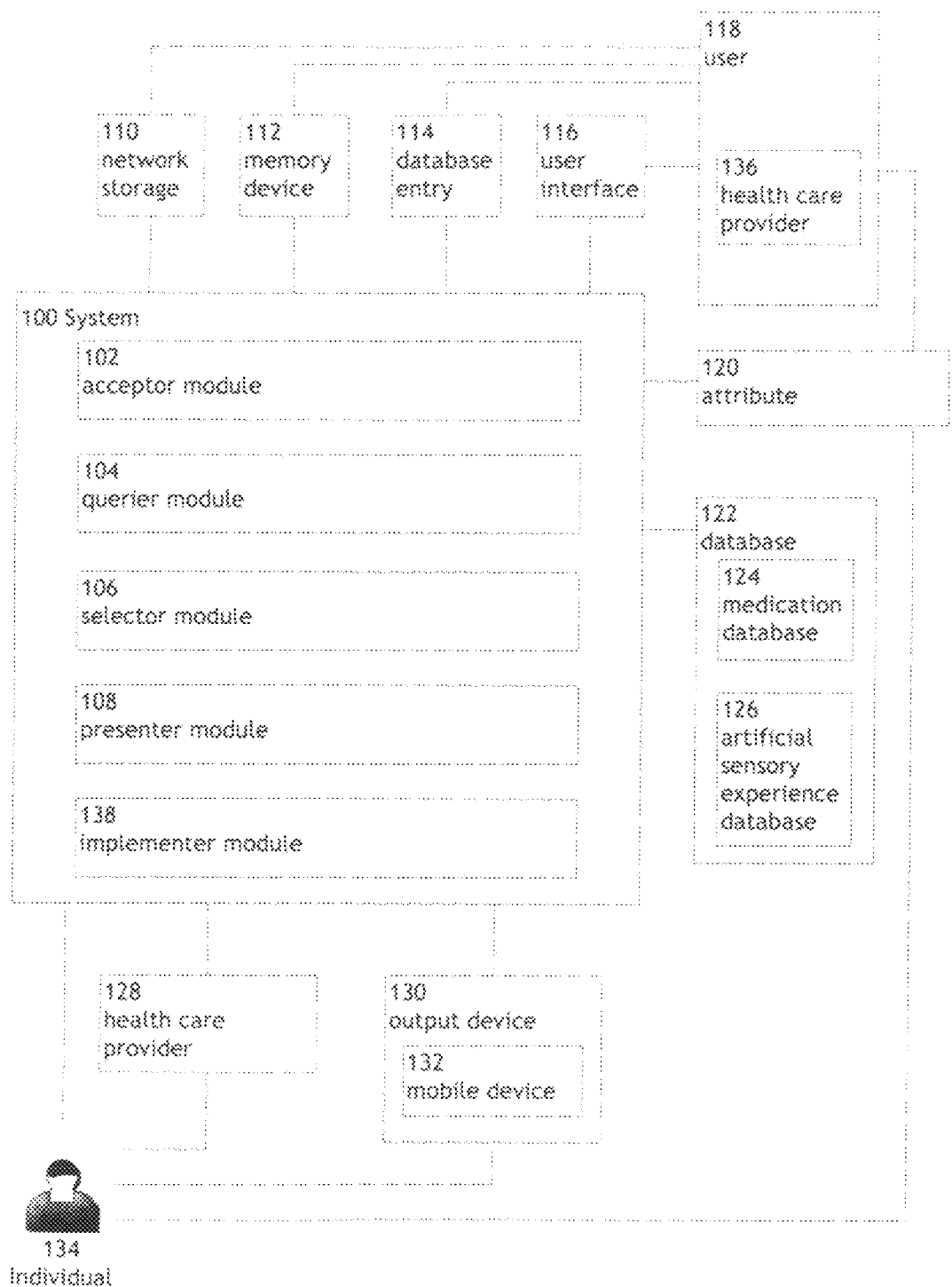
FIG. 1 illustrates an exemplary environment in which one or more technologies may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates a system 100 for accepting at least one attribute of at least one individual, querying at least one database at least partly based on the at least one attribute, selecting from the at least one database at least one prescription medication and at least one artificial sensory experience to address the at least one attribute of at least one individual, and presenting an indication of the at least one prescription medication and the at least one artificial sensory experience at least partly based on the selecting from the at least one database at least one prescription medication and at least one artificial sensory experience to address the at least one attribute of at least one individual. The system 100 may include acceptor module 102, querier module 104, selector module 106, presenter module 108, implementer module 138, and/or modifier module 140. Acceptor module 102 may receive attribute 120 from network storage 110, memory device 112, database entry 114, and/or user interface 116. User interface 116 may receive information from user 118. User 118 may include health care provider 136. Querier module 104 may search database 122. Database 122 may include medication database 124 and/or artificial sensory experience database 126. Presenter module 108 may present to health care provider 128, output device 130, and/or individual 134. Output device 130 may include mobile device 132. Modifier module 140 may include restrictor module 142, granter module 144, alterer module 146, adder module 148, deleter module 150, and/or acceptor module 152. System 100 generally represents instrumentality for accepting at least one attribute of at least one individual, querying at least one database at least partly based on the at least one attribute, selecting from the at least one database at least one prescription medication and at least one artificial sensory experience to address the at least one attribute of at least one individual, and presenting an indication of the at least one prescription medication and the at least one artificial sensory experience at least partly based on the selecting from the at least one database at least one prescription medication and at least one artificial sensory experience to address the at least one attribute of at least one individual. The operations of accepting at least one attribute of at least one individual, querying at least one database at least partly based on the at least one attribute, selecting from the at least one database at least one prescription medication and at least one artificial sensory experience to address the at least one attribute of at least one individual, and presenting an indication of the at least one prescription medication and the at least one artificial sensory experience at least partly based on the selecting from the at least one database at least one prescription medication and at least one artificial sensory experience to address the at least one attribute of at least one individual may be accomplished electronically, such as with a set of interconnected electrical components, an integrated circuit, and/or a computer processor.

Figure 2:
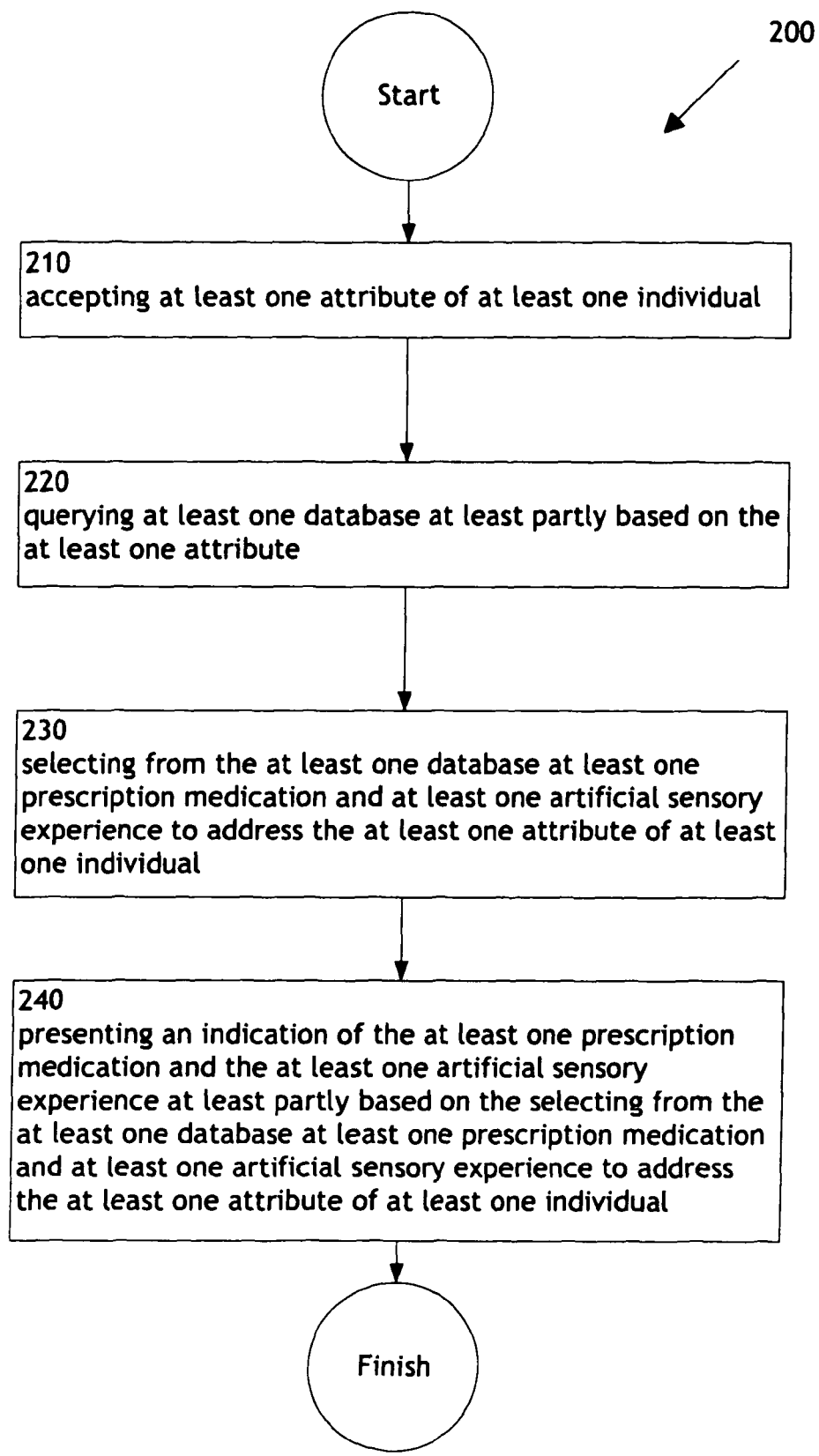
FIG. 2 illustrates an operational flow representing example operations related to selecting a combination of at least one prescription medication and at least one artificial sensory experience.

FIG. 2 illustrates an operational flow 200 representing example operations related to accepting at least one attribute of at least one individual, querying at least one database at least partly based on the at least one attribute, selecting from the at least one database at least one prescription medication and at least one artificial sensory experience to address the at least one attribute of at least one individual, and/or presenting an indication of the at least one prescription medication and the at least one artificial sensory experience at least partly based on the selecting from the at least one database at least one prescription medication and at least one artificial sensory experience to address the at least one attribute of at least one individual. In FIG. 2 and in following figures that include various examples of operational flows, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 200 moves to an operation 210. Operation 210 depicts accepting at least one attribute of at least one individual. For example, as shown in FIG. 1, acceptor module 102 may accept at least one attribute of at least one individual. In one instance, acceptor module 102 can accept from a user 118 and a user interface 116 an attribute 120 including an attribute of a personal health history associated with an individual named John Smith. In some instances, acceptor module 102 may include a computer processor.

Then, operation 220 depicts querying at least one database at least partly based on the at least one attribute. For example, as shown in FIG. 1, querier module 104 may search at least one database at least partly based on the at least one attribute. In one example and continuing with the previous example, querier module 104 can search a database 122 including a medication database 124 and artificial sensory experience database 126 at least partly based on the attribute including an attribute of a personal health history associated with an individual named John Smith. In some instances, querier module 104 may include a computer processor.

Then, operation 230 depicts selecting from the at least one database at least one prescription medication and at least one artificial sensory experience to address the at least one attribute of at least one individual. For example, as shown in FIG. 1, selector module 106 may select from the at least one database at least one prescription medication and at least one artificial sensory experience to address the at least one attribute of at least one individual. In one instance and continuing with the previous example, selector module 106 can select from a medication database 124 and artificial sensory experience database 126 a prescription medication and an artificial sensory experience for addressing the attribute 120 including an attribute of a personal health history associated with an individual named John Smith. In some instances, selector module 106 may include a computer processor.

Then, operation 240 depicts presenting an indication of the at least one prescription medication and the at least one artificial sensory experience at least partly based on the selecting from the at least one database at least one prescription medication and at least one artificial sensory experience to address the at least one attribute of at least one individual. For example, as shown in FIG. 1, presenter module 108 may present the at least one prescription medication and the at least one artificial sensory experience at least partly based on the searching at least one database at least partly based on the at least one attribute. In one instance and continuing with the previous example, presenter module 108 can present to a medical professional the prescription medication and the artificial sensory experience based on searching the medication database 124 and artificial sensory experience database 126 based on the at least one attribute 120 including an attribute of a personal health history associated with an individual named John Smith. In some instances, presenter module 108 may include a computer processor.

Figure 3:
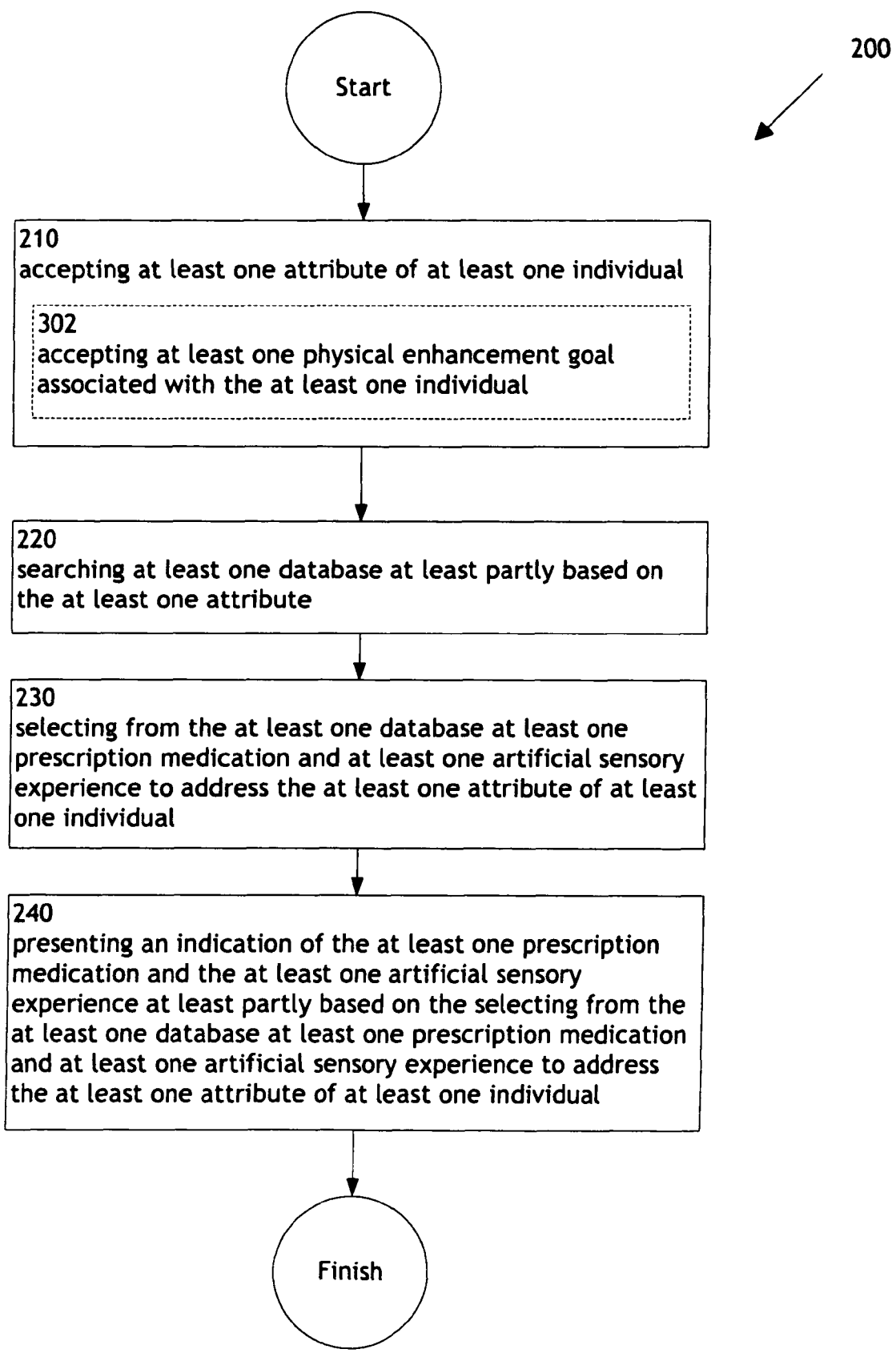
FIG. 3 illustrates an alternative embodiment of the operational flow of FIG. 2.

FIG. 3 illustrates alternative embodiments of the example operational flow 200 of FIG. 2. FIG. 3 illustrates example embodiments where the operation 210 may include at least one additional operation. Additional operations may include an operation 302.

Operation 302 illustrates accepting at least one physical enhancement goal associated with the at least one individual. For example, as shown in FIG. 1, acceptor module 102 may accept from a database entry 114 at least one physical enhancement goal associated with the at least one individual. In one instance and continuing with the above example, acceptor module 102 accepts from memory device 112 at least one physical enhancement goal associated with an individual named John Smith. A physical enhancement goal may include a physical state and/or situation an individual may plan to achieve. Some examples of a physical enhancement goal may include achieving a certain state of relaxation, reaching a certain body mass, maintaining a specific cholesterol level, achieving an athletic performance goal, and/or lowering a blood pressure level. In some instances, acceptor module 102 may include a computer processor.

Figure 4:
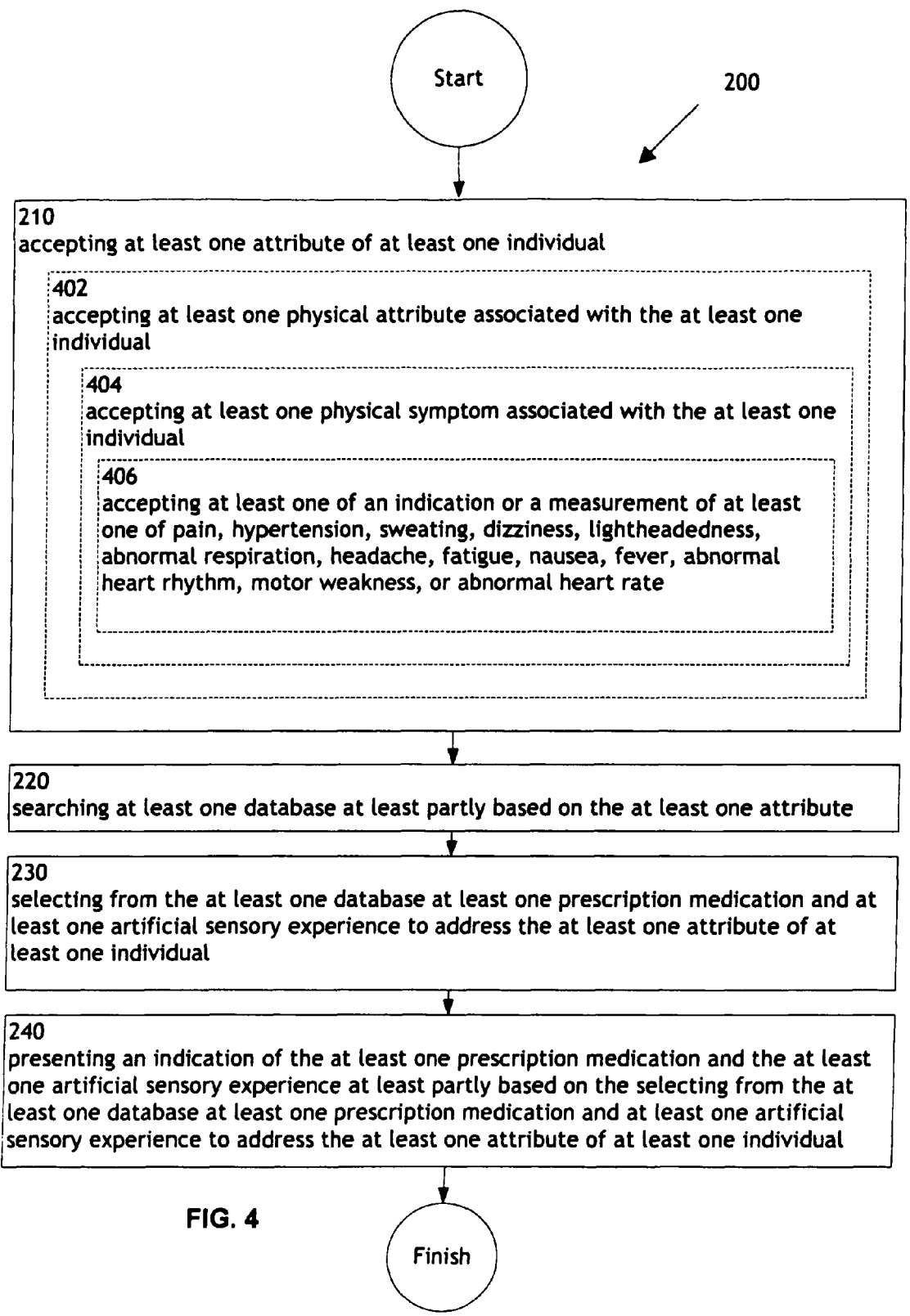
FIG. 4 illustrates an alternative embodiment of the operational flow of FIG. 2.

FIG. 4 illustrates alternative embodiments of the example operational flow 200 of FIG. 2. FIG. 4 illustrates example embodiments where the operation 210 may include at least one additional operation. Additional operations may include an operation 402, an operation 404, and/or an operation 406.

Operation 402 illustrates accepting at least one physical attribute associated with the at least one individual. For example, as shown in FIG. 1, acceptor module 102 may accept from network storage 110 at least one physical attribute associated with the at least one individual. In one instance, acceptor module 102 can accept a physical attribute 120 associated with a group of twenty individuals including an individual weight for each individual. A physical attribute may include an attribute that may be described and/or detected using senses, that has substance and/or a material existence, and/or that may be acted upon by physical force. Some examples of a physical attribute may include a biochemical measurement such as blood sugar level, a smell, an appearance, a physiological measurement such as blood pressure, and/or skin conductivity. In some instances, acceptor module 102 may include a computer processor.

Operation 404 illustrates accepting at least one physical symptom associated with the at least one individual. For example, as shown in FIG. 1, acceptor module 102 may accept at least one physical symptom associated with the at least one individual. In one example, acceptor module 102 can accept from a user 118 and/or user interface 116 a physical symptom including an indication of influenza such as a fever associated with an individual named Mark White. A physical symptom may include a manifestation, sign, and/or an indication of the presence of a disease and/or some other bodily disorder and/or abnormality. Some examples of a physical symptom may include pain, swelling, fever, rash, and/or discoloration. In some instances, acceptor module 102 may include a computer processor.

Operation 406 illustrates accepting at least one of an indication or a measurement of at least one of pain, hypertension, sweating, dizziness, lightheadedness, abnormal respiration, headache, fatigue, nausea, fever, abnormal heart rhythm, motor weakness, or abnormal heart rate. For example, as shown in FIG. 1, acceptor module 102 may accept from at least one of an indication or a measurement of at least one of pain, high blood pressure, sweating, dizziness, lightheadedness, abnormal respiration, headache, fatigue, hunger, nausea, fever, abnormal heart rhythm, motor weakness, or abnormal heart rate. In one example, acceptor module 102 can accept an indication of pain and a measurement of high blood pressure from network storage 110. Pain may include a sensation of somatic hurt or disorder and may include acute pain and/or chronic pain. Hypertension may include chronically elevated blood pressure and may be considered to be present when a person's systolic blood pressure is consistently about 140 mm Hg or greater and/or their diastolic blood pressure is consistently about 90 mm Hg or greater. Sweating may include the excessive production and/or evaporation of fluid excreted by the sweat glands in the skin. Dizziness may include vertigo, disequilibrium, pre-syncope, and/or other balance disorders. Lightheadedness may include a sensation of dizziness and/or fainting. Abnormal respiration may include atypical and/or pathological breathing patterns. Headache may include pain in the head, neck, and/or upper back and may be a symptom of tension, migraine, dehydration, eye strain, sinus disorders, and/or low blood sugar. Fatigue may include muscle weakness and/or lack of strength. Nausea may include the sensation of unease and/or discomfort in the stomach, often with the urge to vomit. Fever may include an increase in internal body temperature to levels above normal. Abnormal heart rhythm may include inconsistent and/or irregular rhythmic contractions in the heart such as sick sinus syndrome, atrial fibrillation, and/or atrial flutter. Motor weakness may include a lack of strength and/or function in the portion of the central nervous system involved in movement. An abnormal heart rate may include an irregular heart contraction frequency such as bradycardia, tachycardia or the like. In some instances, acceptor module 102 may include a computer processor.

Figure 5:
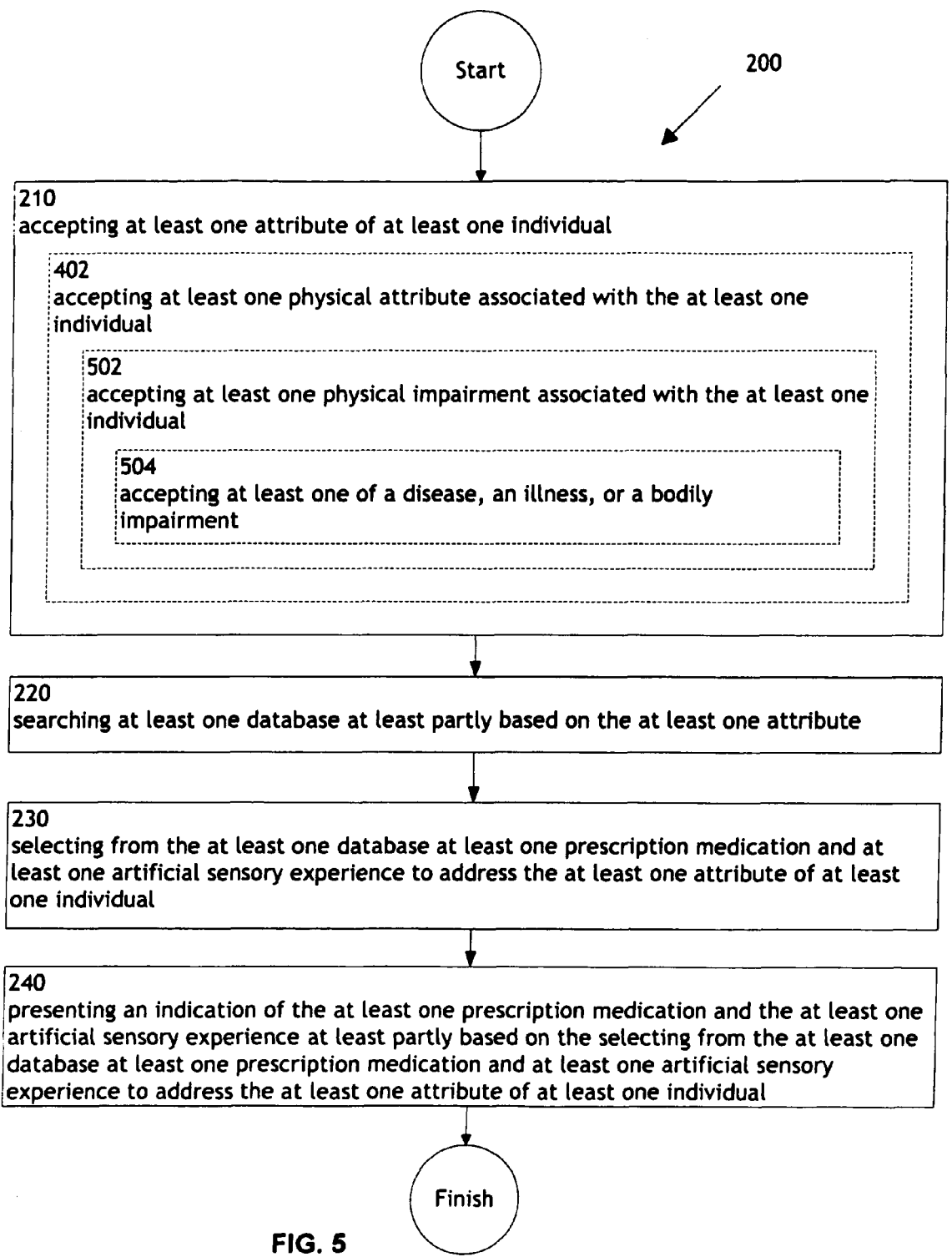
FIG. 5 illustrates an alternative embodiment of the operational flow of FIG. 2.

FIG. 5 illustrates alternative embodiments of the example operational flow 200 of FIG. 2. FIG. 5 illustrates example embodiments where the operation 210 may include at least one additional operation. Additional operations may include an operation 502, and/or an operation 504. Further, operation 502 illustrates accepting at least one physical impairment associated with the at least one individual. For example, as shown in FIG. 1, acceptor module 102 may accept at least one physical impairment associated with the at least one individual from a user 118 and a user interface 116. In one instance, acceptor module 102 accepts a physical impairment including a bodily impairment associated with an individual named Fred Johnson from a user 118 and/or a user interface 116. A physical impairment may include a condition or function judged to be significantly impaired relative to the usual standard of an individual of their group and may include physical impairment, sensory impairment, and/or disease. In some instances, acceptor module 102 may include a computer processor.

Operation 504 illustrates accepting at least one of a disease, an illness, or a bodily impairment. For example, as shown in FIG. 1, acceptor module 102 may accept at least one of a disease, an illness, or a bodily impairment. In one example, acceptor module 102 accepts an indication of a disease and a bodily impairment from database entry 114. A disease may include an abnormal condition of an organism that impairs bodily functions associated with one or more specific symptoms and signs and may include discomfort, distress, dysfunction, injury, a disorder, a syndrome, infection, and/or other atypical variation associated with structure and/or function of the body. An illness may include any state of poor health. Some examples of an illness may include cancer, the common cold, influenza, pneumonia, and/or high cholesterol. A bodily impairment may include a diminished ability in body function and/or structure. In some instances, acceptor module 102 may include a computer processor.

Figure 6:
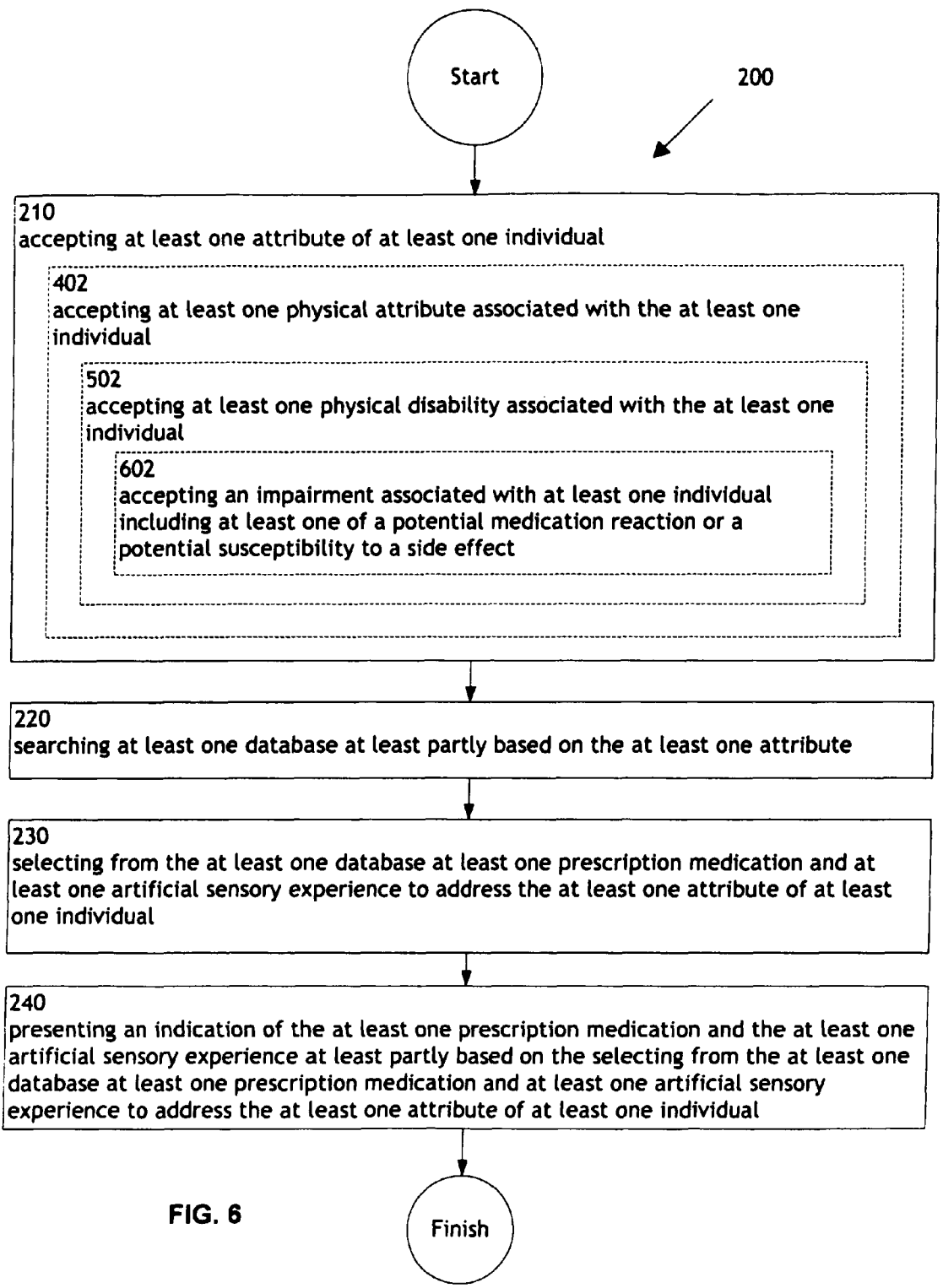
FIG. 6 illustrates an alternative embodiment of the operational flow of FIG. 2.

FIG. 6 illustrates alternative embodiments of the example operational flow 200 of FIG. 2. FIG. 6 illustrates example embodiments where operation 210 may include at least one additional operation. Additional operations may include an operation 602. Operation 602 illustrates accepting an impairment associated with at least one individual including at least one of a potential medication reaction or a potential susceptibility to a side effect. For example, as shown in FIG. 1, acceptor module 102 may accept an impairment associated with at least one individual including at least one of a potential medication reaction or a potential susceptibility to a side effect. In one example, acceptor module 102 can accept from network storage 110 an impairment associated with at least one individual including at least one of a potential medication reaction or a potential susceptibility to a side effect. A potential medication reaction may include a possible response a person may exhibit resulting from at least one drug and/or medication administered to the person. A potential medication reaction may include an allergy and/or a drug and/or medication interaction with a separate drug and/or medication. A potential susceptibility to a side effect may include the probability a certain person may be vulnerable to a side effect coupled with a specific drug and/or medication. In some instances, acceptor module 102 may include a computer processor.

Figure 7:
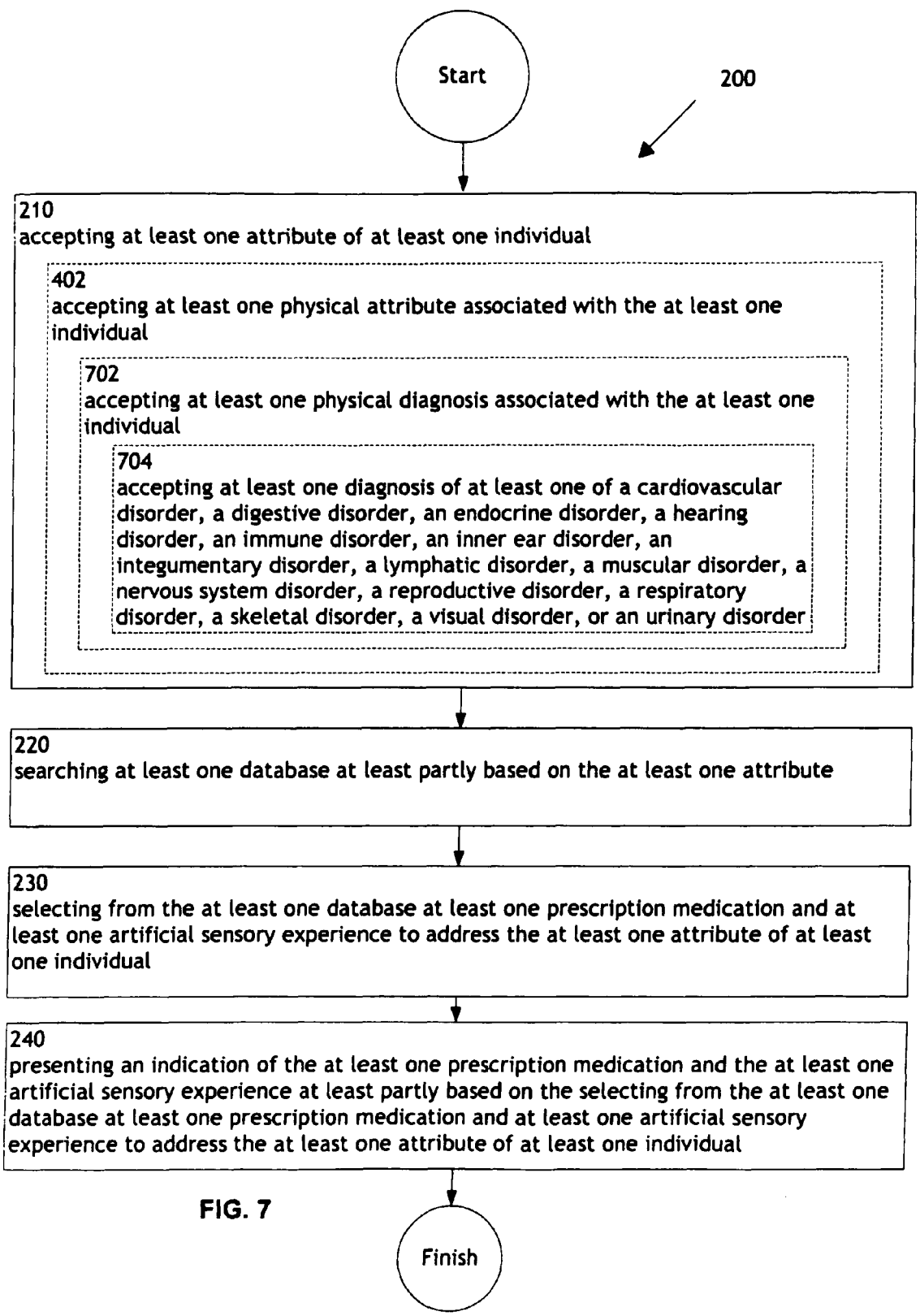
FIG. 7 illustrates an alternative embodiment of the operational flow of FIG. 2.

FIG. 7 illustrates alternative embodiments of the example operational flow 200 of FIG. 2. FIG. 7 illustrates example embodiments where the operation 210 may include at least one additional operation. Additional operations may include an operation 702, and/or an operation 704. Further, operation 702 illustrates accepting at least one physical diagnosis associated with the at least one individual. For example, as shown in FIG. 1, acceptor module 102 may accept at least one physical diagnosis associated with the at least one individual. In a specific example, acceptor module 102 accepts from memory device 112 a physical diagnosis associated with a group of ten individuals. A physical diagnosis may include identifying a disease and/or condition by its outward signs and/or symptoms. Some examples of a physical diagnosis may include identifying influenza and/or identifying Alzheimer's disease. In some instances, acceptor module 102 may include a computer processor.

Operation 704 illustrates accepting at least one diagnosis of at least one of a cardiovascular disorder, a digestive disorder, an endocrine disorder, a hearing disorder, an immune disorder, an inner ear disorder, an integumentary disorder, a lymphatic disorder, a muscular disorder, a nervous system disorder, a reproductive disorder, a respiratory disorder, a skeletal disorder, a visual disorder, or an urinary disorder. For example, as shown in FIG. 1, acceptor module 102 may accept at least one diagnosis of at least one of a cardiovascular disorder, a digestive disorder, an endocrine disorder, an integumentary disorder, a lymphatic disorder, a muscular disorder, a nervous system disorder, a reproductive disorder, a respiratory disorder, a skeletal disorder, or an urinary disorder. In a specific instance, acceptor module 102 can accept from user interface 116 and/or user 118 a diagnosis of a respiratory disorder. A cardiovascular disorder may include a disorder associated with the circulatory system including the pumping and channeling of blood to and from the body and lungs with the heart, the blood, and the blood vessels. Examples of a circulatory disorder include high blood pressure, coronary heart disease, atherosclerosis, or the like. A digestive disorder may include a disorder associated with the esophagus, the stomach, the liver, the gallbladder, the pancreas, the intestines, the rectum, the anus, and/or the digestive system including digestion and processing food with salivary glands. Examples of a digestive disorder include GERD, Crohn's disease, IBS, stomach ulcers including those associated with *H. pylori* infection, or the like. An endocrine disorder may include a disorder associated with the endocrine system including the pancreas, the pituitary gland, the pineal body and/or the pineal gland, the thyroid, the parathyroids, the adrenal glands, and/or communication within the body using hormones made by the endocrine glands, such as the hypothalamus. Examples of an endocrine disorder include diabetes, acromegaly, or the like. A hearing disorder may include a full or partial decrease in the ability to detect or understand sounds. Some examples of a hearing disorder may include otosclerosis, deafness, loss due to death of auditory hair cells, for example that caused by trauma, and/or unilateral hearing loss. An immune disorder may include a dysfunction of the immune system. Examples of an immune disorder may include an immunodeficiency, such as malfunctioning lymphocytes; autoimmunity, such as Coeliac disease and/or autoimmune hepatitis; and/or hypersensitivity, such as asthma. An inner ear disorder may include a balance disorder, such as vertigo, disequilibrium, and/or pre-syncope. An integumentary disorder may include a disorder associated with the integumentary system including the skin, hair, and/or nails, such as psoriasis, eczema, dermatitis, or the like. A lymphatic disorder may include a disorder associated with the lymphatic system including structures involved in the transfer of lymph between tissues and the blood stream and/or the lymph and the nodes and vessels that transport lymph including the immune system, including defending against disease-causing agents with leukocytes, and/or including the tonsils, the adenoids, the thymus, and/or the spleen. Examples of a lymphatic disorder include lymphedema, lymphadenopathy, or the like. A muscle disorder may include a disorder associated with the muscular system including the structure and/or movement of muscles. Examples of a muscle disorder include muscular dystrophy, myasthenia gravis, an injury, such as a strain, or the like. A nervous system disorder may include a disorder associated with the nervous system including collecting, transferring, and/or processing information with the brain, the spinal cord, the peripheral nerves, and/or the nerves. Examples of a nervous system disorder include multiple sclerosis, fibromyalgia, carpal tunnel syndrome, or the like. A reproductive disorder may include a disorder associated with the reproductive system including the sex organs, such as ovaries, fallopian tubes, the uterus, the vagina, mammary glands, testes, the vas deferens, seminal vesicles, the prostate, and/or the penis. Examples of a reproductive disorder include erectile dysfunction, endometriosis, fibroids, or the like. A respiratory disorder may include a disorder associated with the respiratory system including the organs used for breathing, the pharynx, the larynx, the trachea, the bronchi, the lungs, and/or the diaphragm. Examples of a respiratory disorder include emphysema, asthma, or the like. A skeletal disorder may include a disorder associated with the skeletal system including the structural support and protection with bones, cartilage, ligaments, and/or tendons. Examples of a skeletal disorder include osteoporosis, arthritis, tendonitis, a skeletal injury, such as a bone fracture, or the like. A visual disorder may include a disease, impairment, and/or lack of function in the eye and/or in visual perception.

Some examples of a visual disorder may include amblyopia, macular degeneration, glaucoma, and/or blindness. A urinary disorder may include a disorder associated with the urinary system including the kidneys, the ureters, the bladder and/or urethra involved in fluid balance, electrolyte balance and/or the excretion of urine. Examples of a urinary disorder include bladder dysfunction, kidney disease, bladder or urethra infection, or the like. In some instances, acceptor module 102 may include a computer processor.

Figure 8:
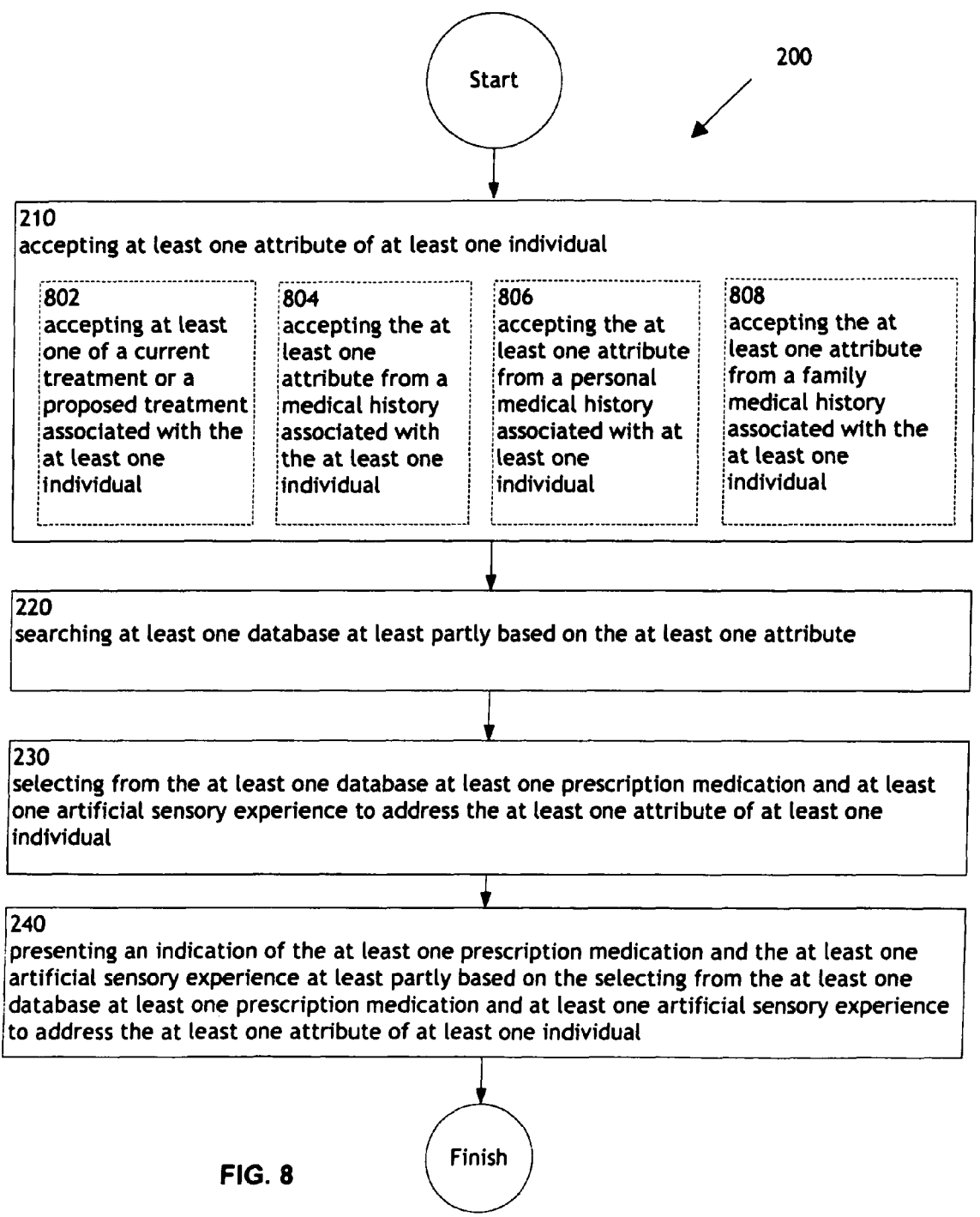
FIG. 8 illustrates an alternative embodiment of the operational flow of FIG. 2.

FIG. 8 illustrates alternative embodiments of the example operational flow 200 of FIG. 2. FIG. 8 illustrates example embodiments where the operation 210 may include at least one additional operation. Additional operations may include an operation 802, an operation 804, an operation 806, and/or operation 808.

Operation 802 illustrates accepting at least one of a current treatment or a proposed treatment associated with the at least one individual. For example, as shown in FIG. 1, acceptor module 102 may accept at least one of a current treatment or a proposed treatment associated with the at least one individual. In one instance, acceptor module 102 accepts a current treatment regime associated with an individual named Cathy Hansen. A current treatment may include one or a series of treatments recommended, administered, and/or prescribed for a certain individual. A proposed treatment may include one or a series of treatments recommended, prescribed, and/or not currently administered to a certain individual. In some instances, acceptor module 102 may include a computer processor.

Operation 804 illustrates accepting the at least one attribute from a medical history associated with the at least one individual. For example, as shown in FIG. 1, acceptor module 102 may accept the at least one attribute from a medical history associated with the at least one individual. In one example, acceptor module 102 may accept from database entry 114 an attribute 120 from a medical history including the number of blood relatives with diabetes associated with an individual named Emily Smith. A medical history may include a list of previous illnesses, symptoms, medicines, treatments, health risk factors, operations, and/or doctor visits for an individual and/or a relation of an individual. In some instances, acceptor module 102 may include a computer processor.

Operation 806 illustrates accepting the at least one attribute from a personal medical history associated with at least one individual. For example, as shown in FIG. 1, acceptor module 102 may accept the at least one attribute from a personal medical history associated with at least one individual. In a specific instance, acceptor module 102 can accept from database entry 114 an attribute 120 including, for example, a list of operations from a personal medical history associated with an individual named Robert Murphy. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. In some instances, acceptor module 102 may include a computer processor.

Operation 808 illustrates accepting the at least one attribute from a family medical history associated with the at least one individual. For example, as shown in FIG. 1, acceptor module 102 may accept the at least one attribute from a family medical history associated with the at least one individual. In one example, acceptor module 102 can accept from network storage 110 an attribute 120 including a list of family members that have had ovarian cancer from a family medical history associated with an anonymous individual or an individual named Elizabeth Green. A family medical history may include a list of previous illnesses, symptoms, medicines, treatments, health risk factors, operations, and/or doctor visits associated with family members related to the at least one individual. In some instances, acceptor module 102 may include a computer processor.

Figure 9:
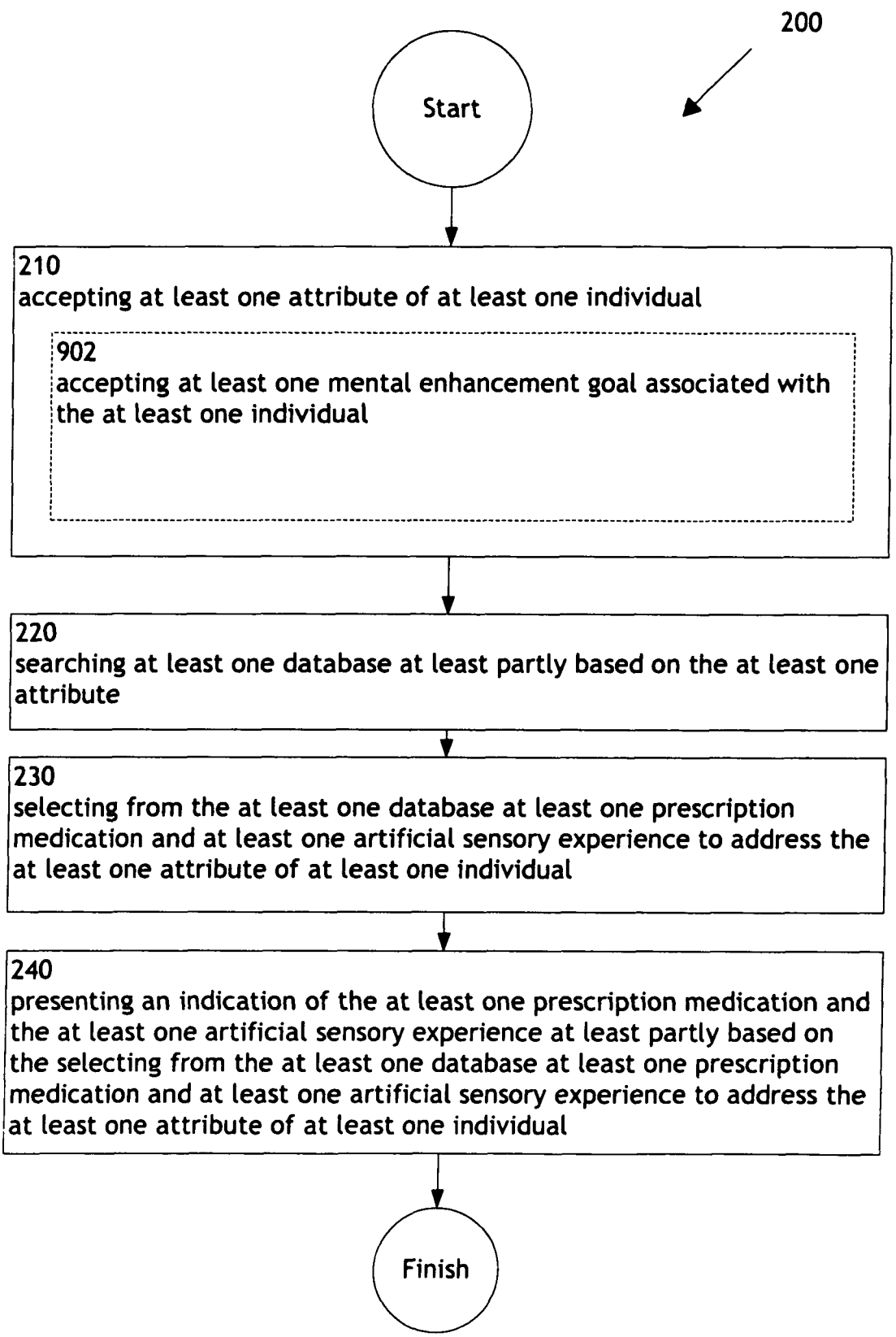
FIG. 9 illustrates an alternative embodiment of the operational flow of FIG. 2.

FIG. 9 illustrates alternative embodiments of the example operational flow 200 of FIG. 2. FIG. 9 illustrates example embodiments where operation 210 may include at least one additional operation. Additional operations may include an operation 902.

Operation 902 illustrates accepting at least one mental enhancement goal associated with the at least one individual. For example, as shown in FIG. 1, acceptor module 102 may accept at least one mental enhancement goal associated with the at least one individual. In one instance, acceptor module 102 can accept a mental enhancement goal associated with, for example, an individual named Dorothy Anderson. A mental enhancement goal may include a mental state and/or situation an individual may plan to achieve. Some examples of a mental enhancement goal may include achieving a certain state of mental awareness such as increased alertness or visual perception, reaching a certain cognitive capability such as enhanced memory or pattern recognition, maintaining a specific attention level, and/or reducing or eliminating a phobia. In some instances, acceptor module 102 may include a computer processor.

Figure 10:
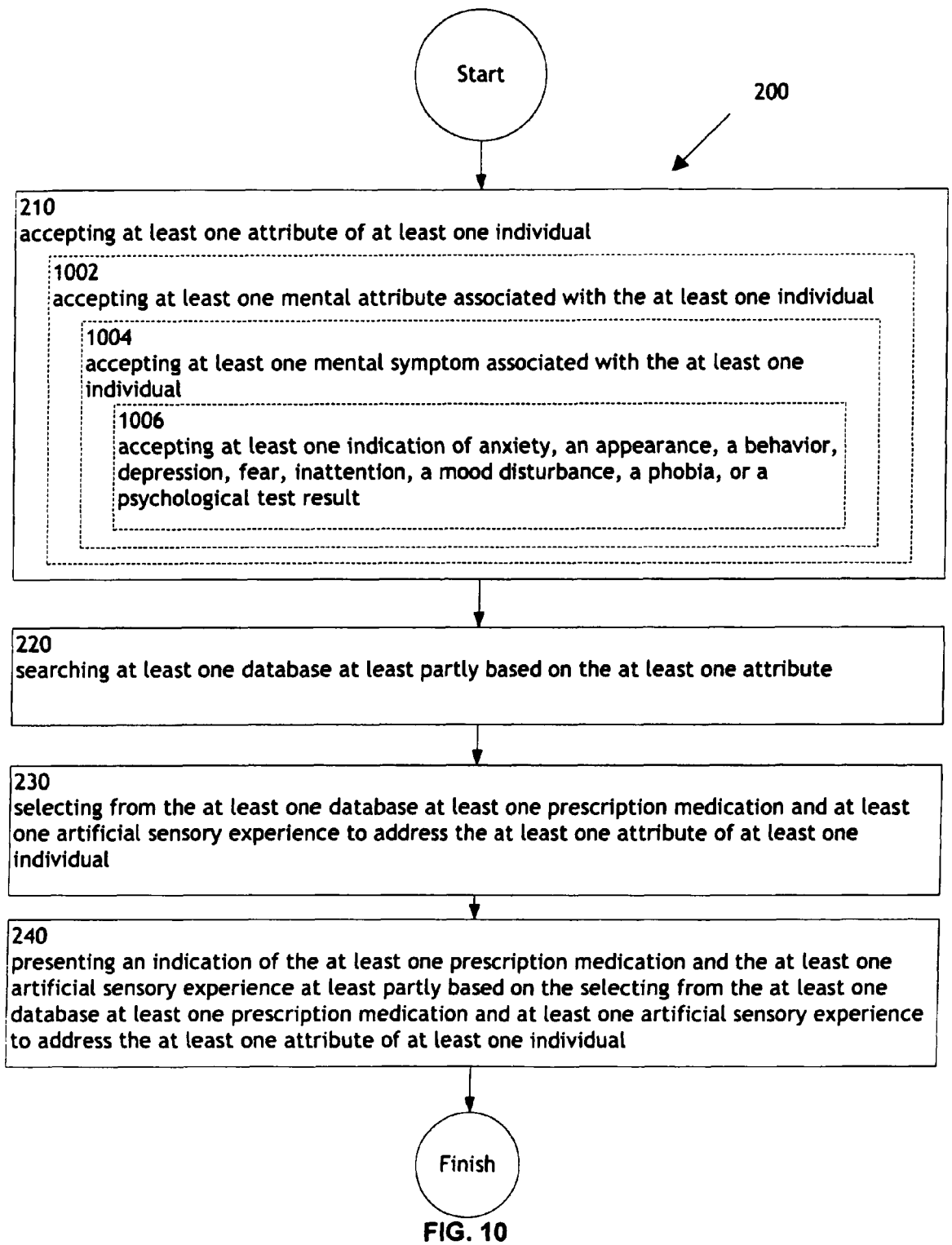
FIG. 10 illustrates an alternative embodiment of the operational flow of FIG. 2.

FIG. 10 illustrates alternative embodiments of the example operational flow 200 of FIG. 2. FIG. 10 illustrates example embodiments where operation 210 may include at least one additional operation. Additional operations may include an operation 1002, an operation 1004, and/or an operation 1006.

Operation 1002 illustrates accepting at least one mental attribute associated with the at least one individual. For example, as shown in FIG. 1, acceptor module 102 may accept at least one mental attribute associated with the at least one individual. In one example, acceptor module 102 can accept a mental attribute 120 including, for example, an intelligence quotient associated with an individual named Judy Peterson. A mental attribute may include an attribute that may be related to and/or associated with basic mental function and/or high-level brain function. Some examples of a mental attribute may include an intelligence quotient (IQ), measurements of brain activity for example using functional MRI or near infra-red technology, and/or measurements of mental development. In some instances, acceptor module 102 may include a computer processor.

Operation 1004 illustrates accepting at least one mental symptom associated with the at least one individual. For example, as shown in FIG. 1, acceptor module 102 may accept at least one mental symptom associated with the at least one individual. In one example, acceptor module 102 can accept from network storage 110 a mental symptom including a stress level measurement associated with an individual named Heather Swanson. A mental symptom may include a manifestation, sign, and/or an indication of the presence of a disease and/or some other mental disorder and/or abnormality. Some examples of a mental symptom may include lack of attention, indication of stress, hyperactivity, nervousness, and/or lack of responsiveness. In some instances, acceptor module 102 may include a computer processor.

Operation 1006 illustrates accepting at least one indication of anxiety, an appearance, a behavior, depression, fear, inattention, a mood disturbance, a phobia, or a psychological test result. For example, as shown in FIG. 1, acceptor module 102 may accept at least one indication of anxiety, appearance, behavior, depression, fear, inattention, mood disturbance, phobia, or psychological test result. In one example, acceptor module 102 can accept from user interface 116 and user 118 an indication of anxiety and depression. Anxiety may include feelings of fear, apprehension, and/or worry and may be accompanied by physical sensations. An appearance may include an outward, audible, and/or visible aspect of a person and/or thing associated with a person. A behavior may include the manner in which a person and/or thing associated with a person acts and/or reacts. Depression may include a mental state characterized by pessimism, a sense of inadequacy, despondence, despair, a low level of energy, and/or a lack of activity. Fear may be caused by impending danger, perceived evil, and/or pain, whether real or imagined. Inattention may include the failure of a person to focus attention. A mood disturbance may include a change in emotional state. A phobia may include an irrational, and/or persistent fear of certain situations, objects, activities, and/or people. A psychological test result may include a sample behavior for inferring a certain generalization about a person. For example, a personality test result may indicate that person has obsessive/compulsive characteristics. In some instances, acceptor module 102 may include a computer processor.

Figure 11:
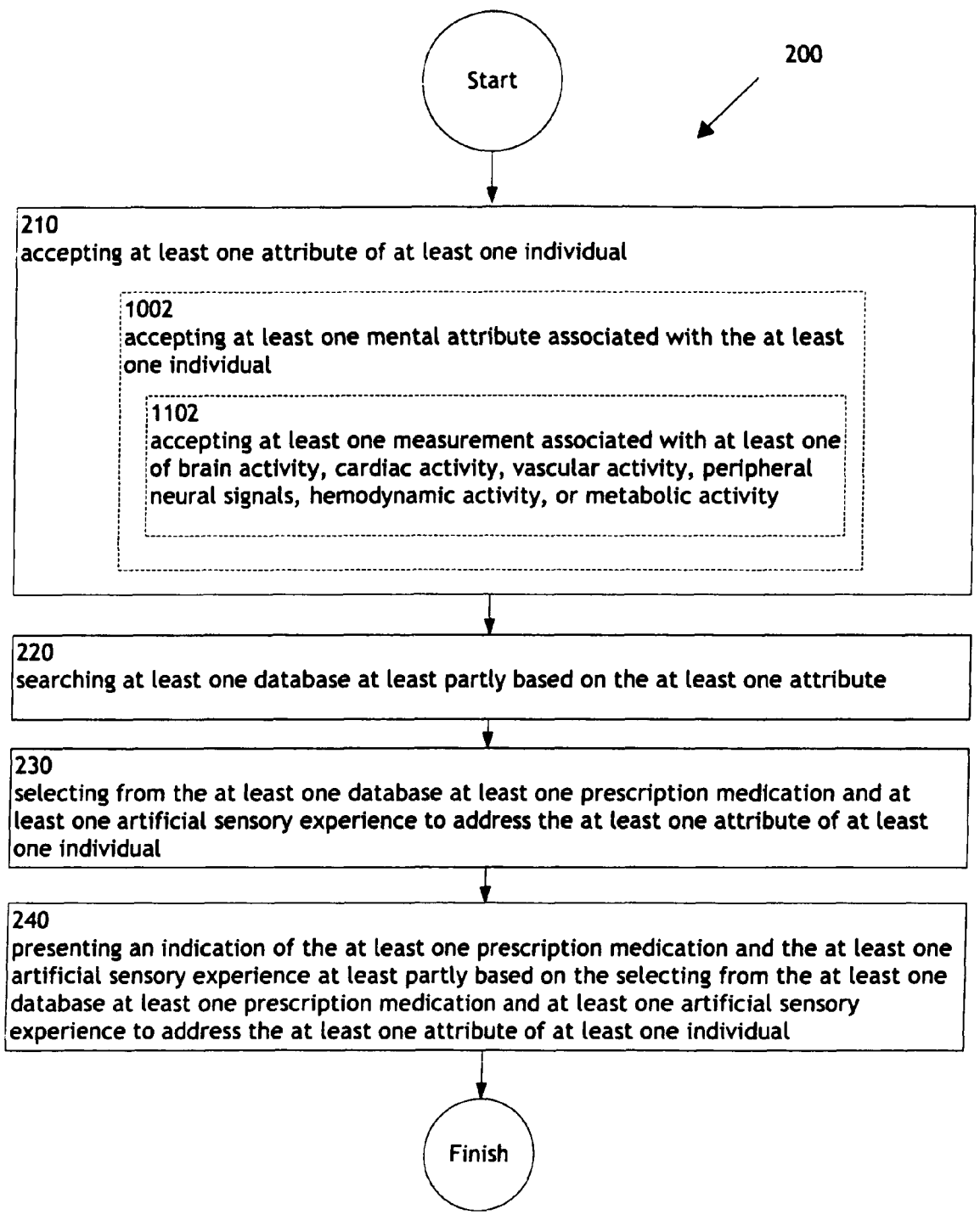
FIG. 11 illustrates an alternative embodiment of the operational flow of FIG. 2.

FIG. 11 illustrates alternative embodiments of the example operational flow 200 of FIG. 2. FIG. 11 illustrates example embodiments where operation 210 may include at least one additional operation. Additional operations may include an operation 1102.

Operation 1102 illustrates accepting at least one measurement associated with at least one of brain activity, cardiac activity, vascular activity, peripheral neural signals, hemodynamic activity, or metabolic activity. For example, as shown in FIG. 1, acceptor module 102 may accept at least one measurement associated with at least one of brain activity, cardiac activity, vascular activity, peripheral neural signals, hemodynamic activity, or metabolic activity. In one instance, acceptor module 102 can accept from database entry 114 a measurement associated with brain activity. Brain activity may include the electrical activity of the brain, such as that measured by EEG, MEG, or the like. Other brain activity measurements may include functional MRI imaging, near infra-red imaging, PET scanning, or the like. Cardiac activity may include electrical activity in the heart, such as that measured by EKG or visual imaging. Vascular activity may include any activity and/or function of the circulatory system. Peripheral neural signals may include neural signals sent through the peripheral nervous system. Hemodynamic activity may include any activity associated with the circulatory system. Metabolic activity may include any activity associated with the biochemical reactions occurring in a living organism. In some instances, acceptor module 102 may include a computer processor.

Figure 12:
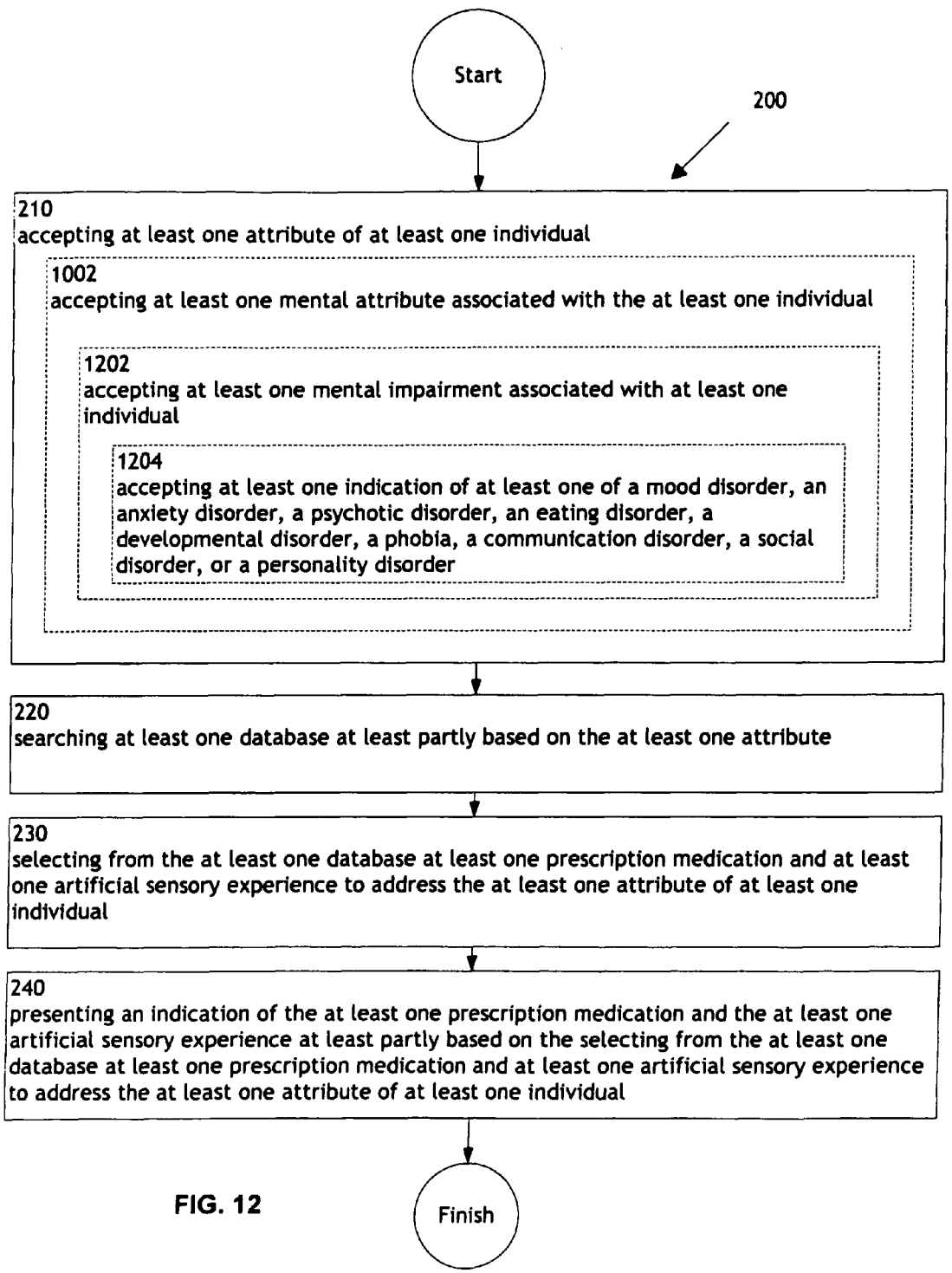
FIG. 12 illustrates an alternative embodiment of the operational flow of FIG. 2.

FIG. 12 illustrates alternative embodiments of the example operational flow 200 of FIG. 2. FIG. 12 illustrates example embodiments where operation 210 may include at least one additional operation. Additional operations may include an operation 1202, and/or an operation 1204.

Operation 1202 illustrates accepting at least one mental impairment associated with at least one individual. For example, as shown in FIG. 1, acceptor module 102 may accept at least one mental impairment associated with at least one individual. In one example, acceptor module 102 can accept from memory device 112 a mental impairment associated with an individual named Richard Lewis. A mental impairment may include a condition or function judged by a health care provider to be significantly impaired relative to the usual standard of an individual of their group, and may include mental impairment, sensory impairment, and/or mental disease. In some instances, acceptor module 102 may include a computer processor.

Operation 1204 illustrates accepting at least one indication of at least one of a mood disorder, an anxiety disorder, a psychotic disorder, an eating disorder, a developmental disorder, a phobia, a communication disorder, a social disorder, or a personality disorder. For example, as shown in FIG. 1, acceptor module 102 may accept at least one indication of at least one of a mood disorder, an anxiety disorder, a psychotic disorder, an eating disorder, a developmental disorder, a phobia, or a personality disorder. In one instance, acceptor module 102 can accept from user interface 116 and/or user 118 an indication of a mood disorder including a mood change and the onset of depression in a specific individual. A mood disorder may include a condition whereby the prevailing emotional mood is distorted or inappropriate to the circumstances, and may include examples such as bipolar disorder, an alteration in mood, and/or depression. An anxiety disorder may include nervous system disorders such as irrationality, illogical worry not based on fact, fear, and/or phobia. A psychotic disorder may include a state of mind in which thinking becomes irrational and/or disturbed and may include hallucinations, abnormal perception, mania, dementia, delusions and/or delusional beliefs, delirium, depression, psychosis personality disorder, personality changes, and/or disorganized thinking. An eating disorder may include a compulsion to eat and/or avoid eating that negatively affects physical and/or mental health. Some examples of an eating disorder may include anorexia nervosa and bulimia nervosa. A developmental disorder may include a disorder occurring in a child's development, which may retard development. Some examples of a developmental disorder may include an emotional disorder, a cognitive disorder, and/or a mental disorder accompanied by physical traits, such as Down syndrome. A phobia may include an irrational, intense, and/or persistent fear of certain situations, objects, activities, and/or persons. Examples of phobias include social phobias, arachnophobia, xenophobia, and/or claustrophobia. A communication disorder may include a disease and/or a condition partially or totally preventing human communication. Some examples of a communication disorder may include autism, stuttering, and/or aphasia. A social disorder may include a condition characterized by a difficulty in human interaction and/or emotional discomfort in social situations. Some examples of a social disorder may include stage fright, social anxiety disorder, and/or shyness. A personality disorder may include a disorder characterized by pathological trends in personality structure. Some examples of a personality disorder may include a paranoid personality disorder, a narcissistic personality disorder, and/or an obsessive-compulsive personality disorder. In some instances, acceptor module 102 may include a computer processor.

Figure 13:
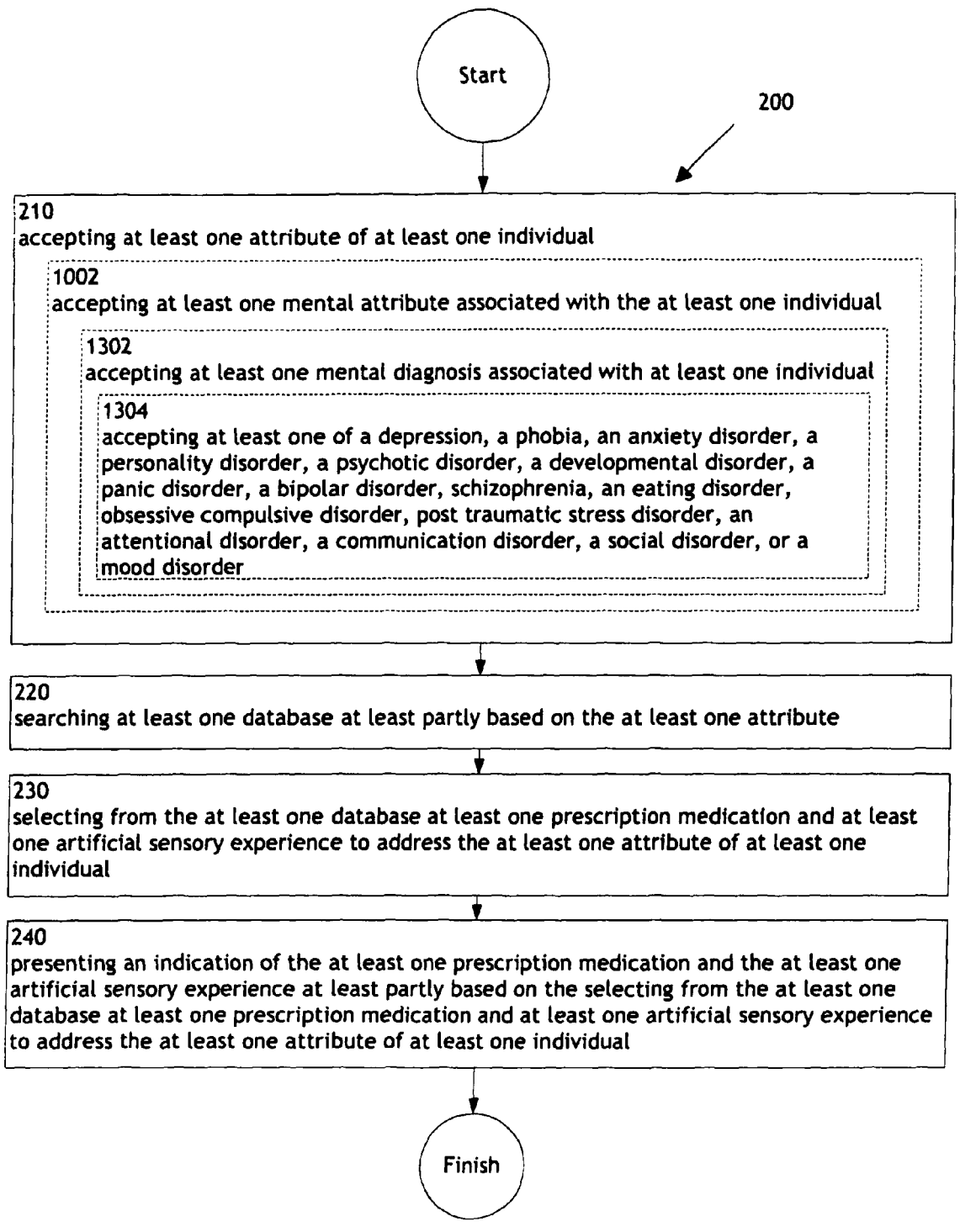
FIG. 13 illustrates an alternative embodiment of the operational flow of FIG. 2.

FIG. 13 illustrates alternative embodiments of the example operational flow 200 of FIG. 2. FIG. 13 illustrates example embodiments where operation 210 may include at least one additional operation. Additional operations may include an operation 1302, and/or an operation 1304. Further, operation 1302 illustrates accepting at least one mental diagnosis associated with at least one individual. For example, as shown in FIG. 1, acceptor module 102 may accept at least one mental diagnosis associated with at least one individual. In a specific instance, acceptor module 102 accepts from memory device 112 a mental diagnosis including a phobia associated with an anonymous individual or an individual named Roy Black. A mental diagnosis may include identifying a mental disorder and/or condition by its symptoms. Some examples of a mental diagnosis may include a mood disorder such as depression, an anxiety disorder such as PTSD, a behavioral disorder such as ADHD, a personality disorder such as borderline personality disorder, and/or a phobia. Mental disorders may include those listed in the Diagnostic and Statistical Manual of Mental Disorders (DSM). In some instances, acceptor module 102 may include a computer processor.

Operation 1304 illustrates accepting at least one of a depression, a phobia, an anxiety disorder, a personality disorder, a psychotic disorder, a developmental disorder, a panic disorder, a bipolar disorder, schizophrenia, an eating disorder, obsessive compulsive disorder, post traumatic stress disorder, an attentional disorder, a communication disorder, a social disorder, or a mood disorder. For example, as shown in FIG. 1, acceptor module 102 may accept at least one of a depression, a phobia, an anxiety disorder, a personality disorder, a psychotic disorder, a developmental disorder, a panic disorder, or a mood disorder. In one example, acceptor module 102 accepts from database entry 114 a diagnosis of depression. Depression may include a mental state characterized by a pessimistic sense of inadequacy and/or a despondent lack of activity. A phobia may include an irrational, intense, and/or persistent fear of certain situations, objects, activities, and/or persons. Some phobias may include social phobias, arachnophobia, xenophobia, and/or claustrophobia. An anxiety disorder may include nervous system disorders such as irrationality, illogical worry not based on fact, fears, and/or phobias. A personality disorder may include a disorder characterized by pathological trends in personality structure. Some examples of a personality disorder may include a paranoid personality disorder, a narcissistic personality disorder, and/or an obsessive-compulsive personality disorder. A psychotic disorder may include a state of mind in which thinking becomes irrational and/or disturbed and may include hallucinations, delusional beliefs, personality changes, and/or disorganized thinking. A developmental disorder may include a disorder occurring in a child's development, which may often retard development. Some examples of a developmental disorder may include psychological or physical disorders. A panic disorder may include a condition characterized by recurring panic attacks in combination with significant behavioral change. A bipolar disorder may include a mood disorder characterized by the presence of one or more episodes of abnormally elevated mood, such as Bipolar I disorder, Bipolar II disorder, cyclothymia, and/or Bipolar-NOS. Schizophrenia may include a mental illness characterized by impairments in the perception or expression of reality, most commonly manifesting as auditory hallucinations, paranoid or bizarre delusions or disorganized speech and thinking in the context of significant social or occupational dysfunction. An eating disorder may include a compulsion to eat or avoid eating, such as anorexia nervosa and/or bulimia nervosa. Obsessive compulsive disorder may include a psychiatric anxiety disorder characterized by obsessive, distressing, intrusive thoughts and related compulsions which attempt to neutralize the obsessions. Post traumatic stress disorder may include an anxiety disorder that can develop after exposure to one or more terrifying events in which grave physical harm occurred or was threatened. An attentional disorder may include a persistent pattern of inattention and/or hyperactivity, as well as forgetfulness, poor impulse control or impulsivity, and distractibility, such as attention-deficit hyperactivity disorder (ADHD). A communication disorder may include a disease and/or a condition partially or totally preventing human communication. Some examples of a communication disorder may include autism, stuttering, and/or aphasia. A social disorder may include a condition characterized by a difficulty in human interaction and/or emotional discomfort in social situations. Some examples of a social disorder may include stage fright, social anxiety disorder, and/or shyness. A mood disorder may include a condition whereby the prevailing emotional mood is distorted or inappropriate to the circumstances and may include examples such as bipolar disorder and/or depression. In some instances, acceptor module 102 may include a computer processor.

Figure 14:
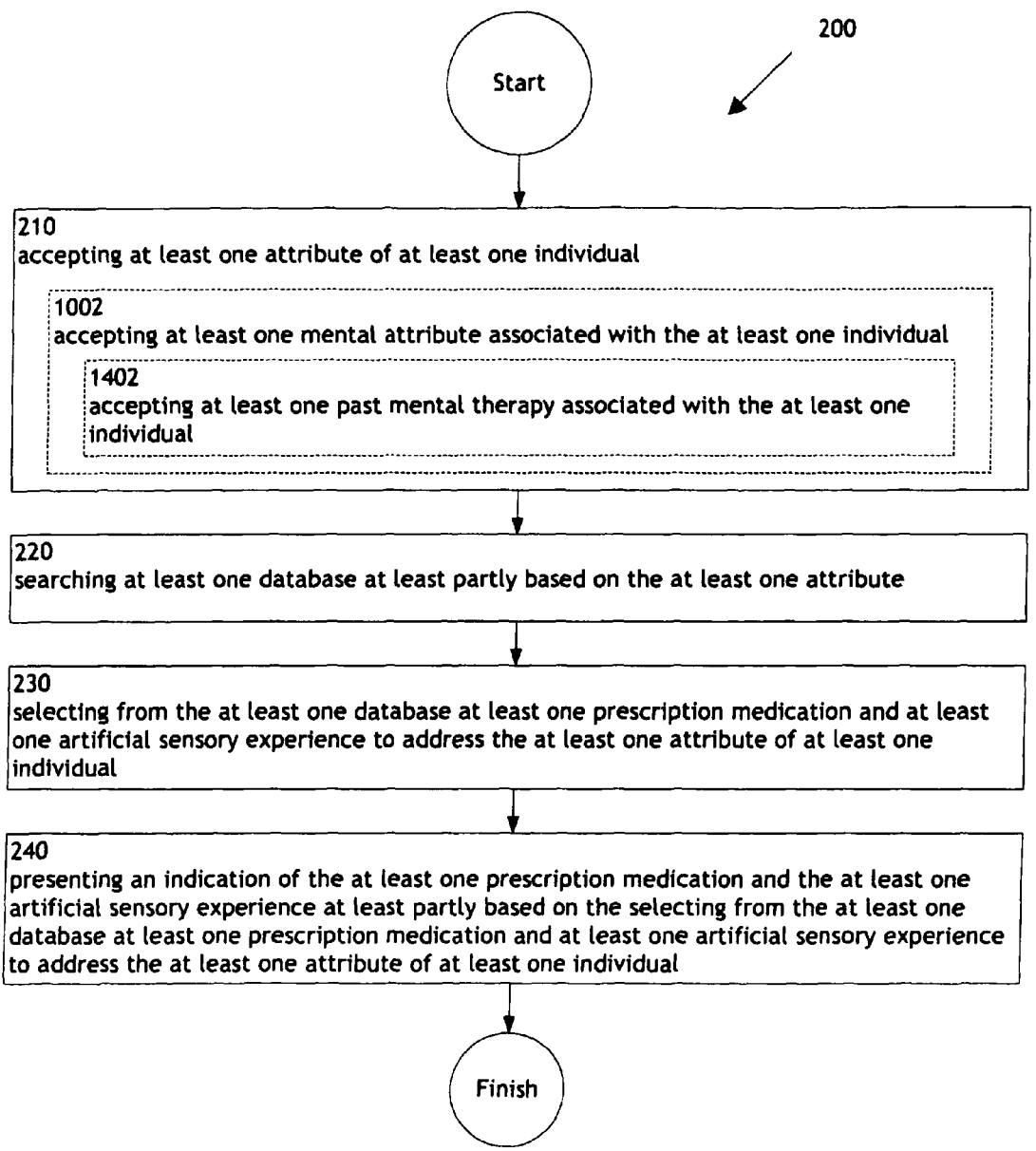
FIG. 14 illustrates an alternative embodiment of the operational flow of FIG. 2.

FIG. 14 illustrates alternative embodiments of the example operational flow 200 of FIG. 2. FIG. 14 illustrates example embodiments where operation 210 may include at least one additional operation. Additional operations may include an operation 1402. Further, operation 1402 illustrates accepting at least one past mental therapy associated with the at least one individual. For example, as shown in FIG. 1, acceptor module 102 may accept at least one past mental therapy associated with the at least one individual. In one instance, acceptor module 102 can accept from database entry 114 a past mental therapy associated with an individual named James Williams or an anonymous individual. A past mental therapy may include a list and/or a record of at least one mental therapy, such as an anti-depressant medication, administered to at least one individual. In some instances, acceptor module 102 may include a computer processor.

Figure 15:
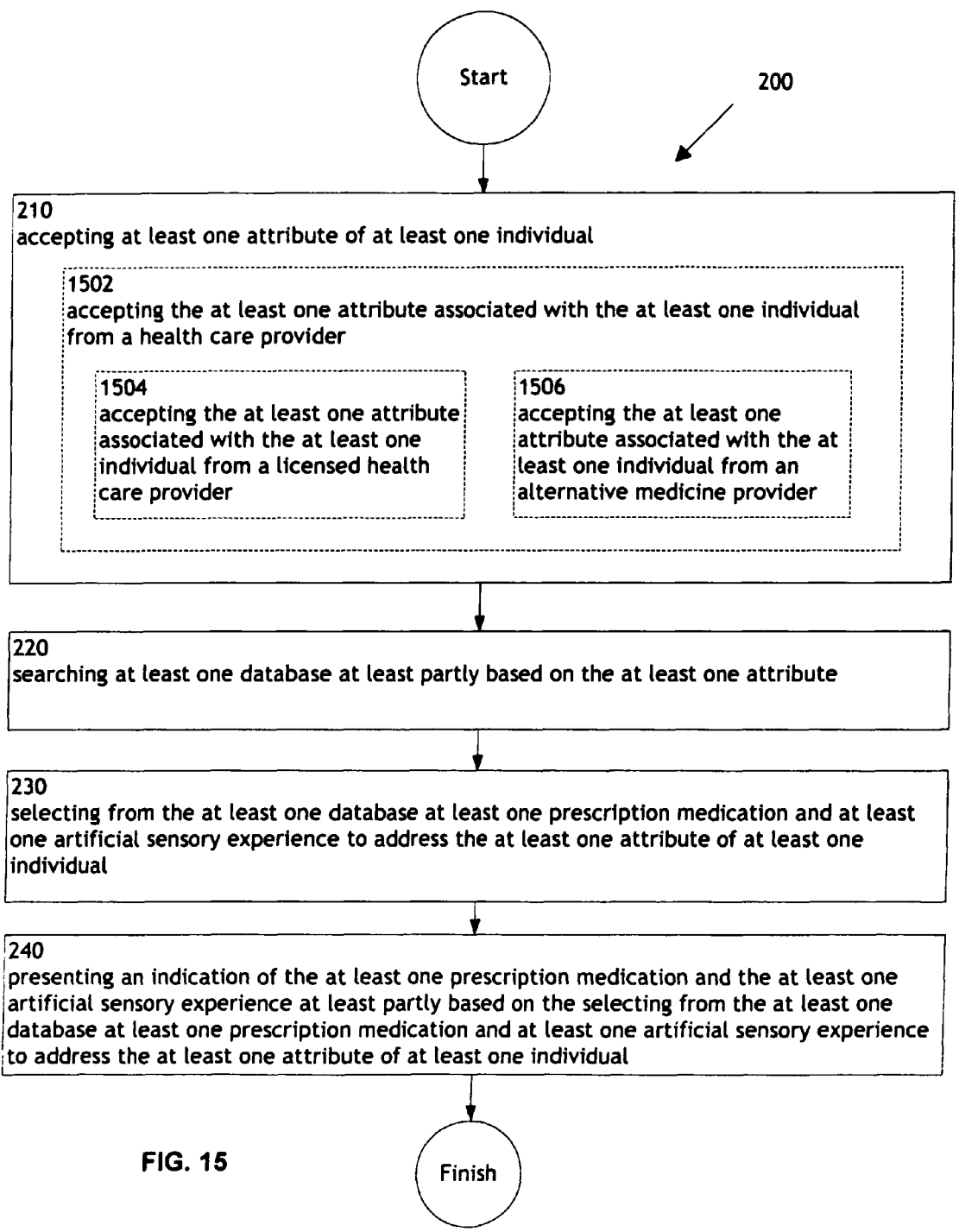
FIG. 15 illustrates an alternative embodiment of the operational flow of FIG. 2.

FIG. 15 illustrates alternative embodiments of the example operational flow 200 of FIG. 2. FIG. 15 illustrates example embodiments where operation 210 may include at least one additional operation. Additional operations may include an operation 1502, an operation 1504, and/or an operation 1506.

Operation 1502 illustrates accepting the at least one attribute associated with the at least one individual from a health care provider. For example, as shown in FIG. 1, acceptor module 102 may accept the at least one attribute associated with the at least one individual from a health care provider. In one example, acceptor module 102 can accept from user interface 116 and/or user 118 an attribute 120 including a medication history associated with a group of fifty individuals from a health care provider 136. A health care provider may include a hospital, a doctor, a nurse, a medical clinic, a dentist, and/or any provider of preventive, diagnostic, therapeutic, rehabilitative, maintenance, or palliative care and/or counseling. A healthcare provider may include a seller and/or dispenser of prescription drugs or medical devices. In some instances, acceptor module 102 may include a computer processor.

Operation 1504 illustrates accepting the at least one attribute associated with the at least one individual from a licensed health care provider. For example, as shown in FIG. 1, acceptor module 102 may accept the at least one attribute associated with the at least one individual from a licensed health care provider. In one instance, acceptor module 102 accepts from memory device 112 an attribute 120 including a symptom indication a phobia associated with an individual named Robert Clark from a licensed health care provider 136. A licensed health care provider may include a person licensed by a governing authority, such as a state, to provide medical and/or health care. Some examples of a licensed health care provider may include a licensed medical doctor or physician, a licensed physician's assistant, and/or a licensed nurse practitioner. In some instances, acceptor module 102 may include a computer processor.

Operation 1506 illustrates accepting the at least one attribute associated with the at least one individual from an alternative medicine provider. For example, as shown in FIG. 1, acceptor module 102 may accept the at least one attribute associated with the at least one individual from an alternative medicine provider. In one instance, acceptor module 102 can accept from network storage 110 an attribute 120 associated with an individual named Connie Martin from an alternative medicine provider. An alternative medicine provider may include a provider of folk medicine, herbal medicine, diet fads, homeopathy, faith healing, new age healing, chiropractic, acupuncture, aromatherapy, naturopathy, massage, reflexology, hypnotism, and/or music therapy. In some instances, acceptor module 102 may include a computer processor.

Figure 16:
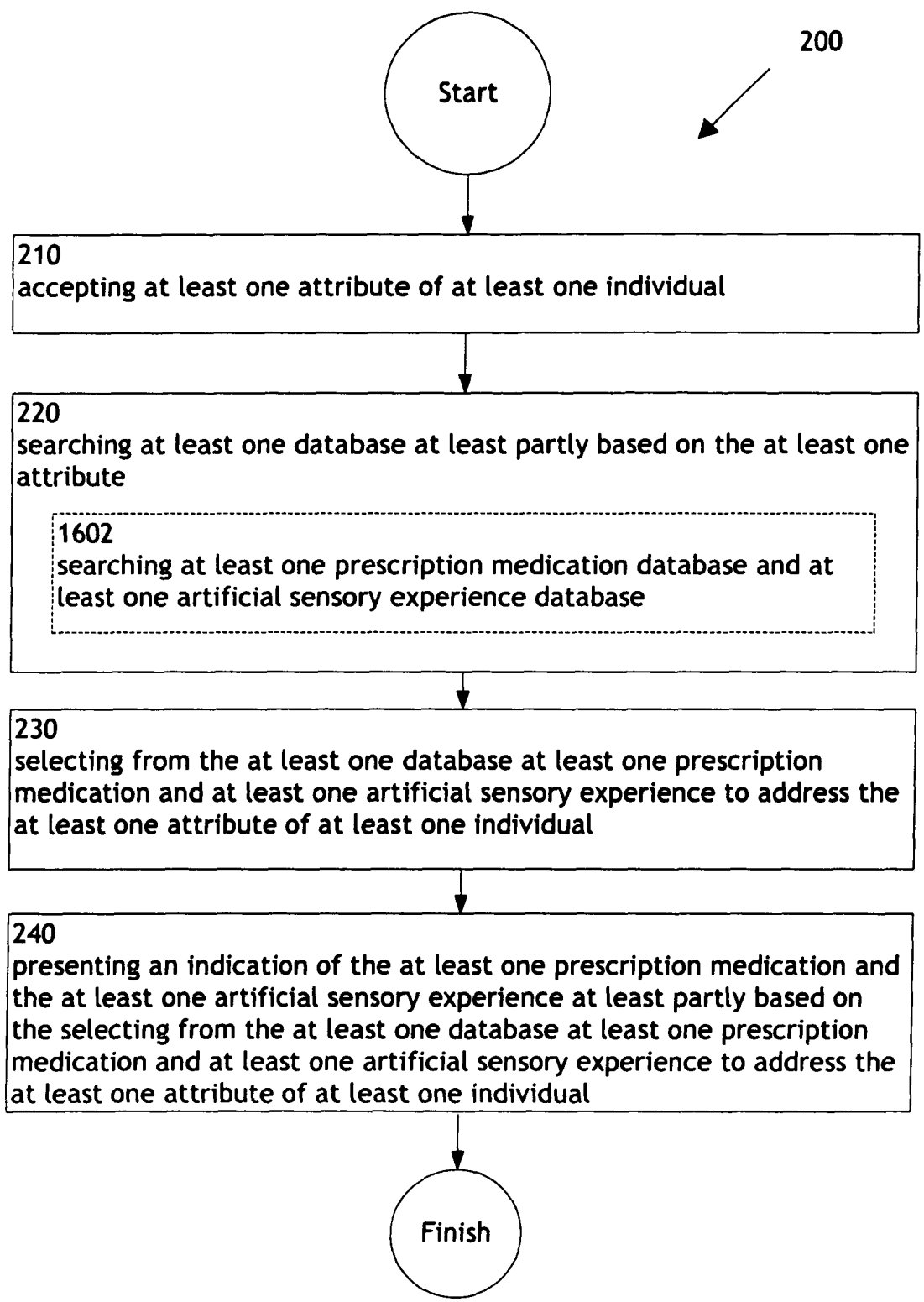
FIG. 16 illustrates an alternative embodiment of the operational flow of FIG. 2.

FIG. 16 illustrates alternative embodiments of the example operational flow 200 of FIG. 2. FIG. 16 illustrates example embodiments where operation 220 may include at least one additional operation. Additional operations may include an operation 1602.

Operation 1602 illustrates searching at least one prescription medication database and at least one artificial sensory experience database. For example, as shown in FIG. 1, querier module 104 may search at least one prescription medication database and at least one artificial sensory experience database. In one example, querier module 104 searches a medication database 124 and an artificial sensory experience database 126. A database may include a collection of data organized for convenient access. The database may include information digitally stored in a memory device 112, as at least a portion of at least one database entry 114, and/or in network storage 110. In some instances, the database may include information stored non-digitally such as at least a portion of a book, a paper file, and/or a non-computerized index and/or catalog. Non-computerized information may be received by acceptor module 102 by scanning or by manually entering the information into a digital format. A prescription database and/or medication database may include any database associated with at least one prescription medication and may be available to health care professionals and/or the public. An artificial sensory experience database may include any database associated with at least one artificial sensory experience and may include a database accessible by the public and/or a health care provider. In some instances, acceptor module 102 and/or querier module 104 may include one or more computer processors.

Figure 17:
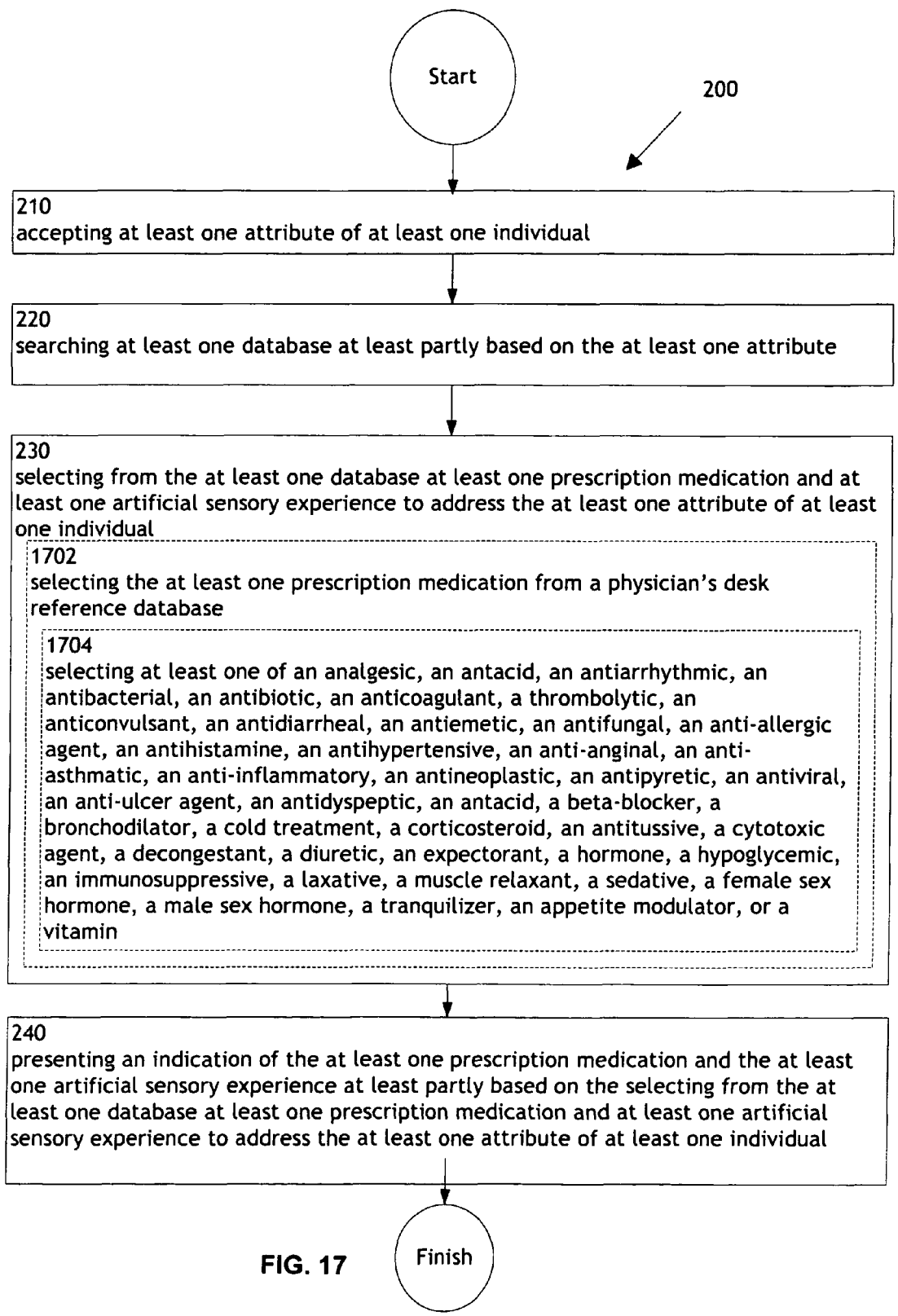
FIG. 17 illustrates an alternative embodiment of the operational flow of FIG. 2.

FIG. 17 illustrates alternative embodiments of the example operational flow 200 of FIG. 2. FIG. 17 illustrates example embodiments where operation 230 may include at least one additional operation. Additional operations may include an operation 1702, and/or an operation 1704.

Operation 1702 illustrates selecting the at least one prescription medication from a physician's desk reference database. For example, as shown in FIG. 1, selector module 106 may select the at least one prescription medication from a physician's desk reference database. In one example, selector module 106 selects the at least one prescription medication from a physician's desk reference database 122, such as a PDR psychiatry database. In some instances, selector module 106 may include a computer processor.

Operation 1704 illustrates selecting at least one of an analgesic, an antacid, an antiarrhythmic, an antibacterial, an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, an antipyretic, an antiviral, an anti-ulcer agent, an antidyspeptic, an antacid, a beta-blocker, a bronchodilator, a cold treatment, a corticosteroid, an antitussive, a cytotoxic agent, a decongestant, a diuretic, an expectorant, a hormone, a hypoglycemic, an immunosuppressive, a laxative, a muscle relaxant, a sedative, a female sex hormone, a male sex hormone, a tranquilizer, an appetite modulator, or a vitamin. For example, as shown in FIG. 1, selector module 106 may select at least one of an analgesic, an antacid, an antiarrhythmic, an antibacterial, an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, an antipyretic, an antiviral, an anti-ulcer agent, an antidyspeptic, an antacid, a beta-blocker, a bronchodilator, a cold treatment, a corticosteroid, a cough suppressant, an antitussive, a cytotoxic agent, a decongestant, a diuretic, an expectorant, a hormone, a hypoglycemic, an immunosuppressive, a laxative, a muscle relaxant, a sedative, a female sex hormone, a male sex hormone, a tranquilizer, an appetite modulator, or a vitamin. An analgesic may include a drug and/or other medication suitable for relieving pain. Additionally, an analgesic may be effective for relieving different degrees of pain. Some examples of an analgesic may include narcotics such as morphine or oxycodone, non-narcotics, an NSAID such as aspirin or naproxen or ibuprofen, and/or acetaminophen. An antacid may include a substance for neutralizing stomach acid, such as a proton pump inhibitor. Some examples of an antacid may include imeprazole and/or a pharmaceutical composition containing aluminum hydroxide, magnesium hydroxide, aluminum carbonate, calcium carbonate, sodium bicarbonate, hydrotalcite, bismuth subsalicylate, magaldrate, and/or simethicone.

An antiarrhythmic may include a drug for controlling a heartbeat irregularity. Some examples of an antiarrhythmic may include a beta blocker such as propanolol, and/or lidocaine, verapamil, and/or quinidine. An antibacterial may include a drug used to treat an infection. Some examples of an antibacterial may include amoxicillin and/or ciprofloxacin. An antibiotic may include a drug made from naturally occurring and/or synthetic substances for combating a bacterial infection. Some examples of an antibiotic may include penicillin, streptomycin, and/or sulfonamide-based drugs. An anticoagulant may include an agent for preventing blood clots. An example of an anticoagulant may include a vitamin K antagonist, such as warfarin, and/or aspirin. A thrombolytic may help dissolve and disperse a blood clot and may be prescribed for patients with recent arterial or venous thrombosis. A thrombolytic may be derived from *Streptomyces* spp. and/or recombinant DNA technology and may include streptokinase, urokinase, and/or a tissue plasminogen activator (TPA) such as alteplase.

An anticonvulsant may include a pharmaceutical administered for the prevention of seizures. Some examples of an anticonvulsant may include a barbiturate, a carbamate, a fatty acid derivative, and/or a sulfonamide. An antidiarrheal may include a drug utilized for the relief of diarrhea. Some examples of an antidiarrheal may include an antispasmodic such as diphenoxylate and loperamide, a bismuth compound, a bulking agent, and/or an absorbent. An antiemetic may include a drug used to treat nausea and vomiting. Some examples of an antiemetic may include a 5-HT3 receptor antagonist, a dopamine antagonist, and/or a histamine. An antifungal may include a drug used to treat fungal infections, the most common of which affect the hair, skin, nails, and/or mucous membranes. Some examples of antifungals may include polyene antifungals, imidazole and triazole antifungals, and/or allylamines. An anti-allergenic agent may include an agent characterized by preventing and/or reducing the effect of an allergen. Some examples of an anti-allergenic may include an antihistamine, cortisone, hydrocortisone, and/or epinephrine. An antihistamine may include an agent used for counteracting the effects of histamine. Some examples of an antihistamine may include a H1-receptor antagonist and/or a H2-receptor antagonist. An antihypertensive may include drugs utilized for lowering blood pressure. Some examples of an antihypertensive may include a diuretic, an adrenergic receptor antagonist, and/or an ACE inhibitor. An anti-anginal may include an agent used for preventing and/or reducing angina and/or chest pain. Some examples of an anti-anginal may include aspirin, ranolazine, and/or ivabradine. An anti-asthmatic may include an agent for preventing and/or reducing asthma and/or its effects. Some examples of an anti-asthmatic may include albuterol, an inhaled steroid, for example budesonide or fluticasone, and/or ipratropium bromide.

An anti-inflammatory may include an agent utilized to reduce inflammation and/or to treat redness, heat, swelling, and/or increased blood flow associated for example, that seen with an infection or injury, or in many chronic diseases such as rheumatoid arthritis and gout. Some anti-inflammatories may include steroids, and/or NSAIDs such as naproxen, ibuprofen, and/or aspirin. An antineoplastic may include drugs used to treat cancer and to inhibit and/or prevent the development of tumors. Some antineoplastics may include alkylating agents, antimetabolites, enzymes, enzyme inhibitors, immune modulators, and taxoids. An antipyretic may include a drug used to reduce a fever. Some examples of an antipyretic may include aspirin and/or acetaminophen. An antiviral may include a drug used to treat viral infections and/or to provide temporary protection against viral infections such as influenza. Some examples of an antiviral may include an interferon, acyclovir, ribavirin, and/or oseltamivir. An anti-ulcer agent may include an agent used for preventing and/or lessening the effect of an ulcer, including stomach ulcers, mouth ulcers, or other types of ulcers. Some examples of an anti-ulcer agent may include a bismuth compound, a prostaglandin analogue, and/or cimetidine. An antidyspeptic may include an agent used for treating and/or preventing dyspepsia. Some examples of an antidyspeptic may include simethicone and/or a proton pump inhibitor, such as esomeprazole. An antacid may include a substance, often a base, which may counteract stomach acidity. Some examples of an antacid may include magnesium hydroxide, aluminum hydroxide, calcium carbonate, and/or bismuth subsalicylate. A beta-blocker may include a beta-adrenergic blocking agent utilized for reducing the oxygen needs of the heart by reducing the heartbeat rate. Some examples of a beta-blocker may include propranolol, esmolol, bisoprolol, and/or timolol. A bronchodilator may include an agent utilized for opening the bronchial tubes within the lungs when the tubes have become narrowed, for example, by muscle spasm and may be used for treating asthma. Some examples of a bronchodilator may include albuterol and/or ipratropium bromide. A cold treatment may include an agent utilized for treating aches, pains, and/or fever accompanying a cold. Some cold treatments may include aspirin, acetaminophen, a decongestant, an antihistamine, and/or caffeine.

A corticosteroid may include a hormonal preparation used as an anti-inflammatory for arthritis or asthma and/or treating some malignancies or compensating for a deficiency of natural hormones. Some examples of a corticosteroid may include cortisol and/or aldosterone. A cough suppressant may include an agent used to soothe irritation caused by coughing and/or to prevent coughing. Some examples of a cough suppressant may include codeine, an antihistamine, and/or dextromethorphan. An antitussive may include a cough suppressant. A cytotoxic agent may include a drug used for killing and/or damaging cells. Some examples of a cytotoxic agent may include actinomycin-D, azathioprine, bleomycin, melphalan, busulphan, doxorubicin, etoposide, an antineoplastic agent, and/or an apoptotic agent. A decongestant may include an agent for reducing the swelling of the mucous membranes lining the nose and/or throat. Some examples of a decongestant may include pseudoephedrine and phenylephrine. A diuretic may include an agent for increasing the quantity of urine produced by the kidneys and passed out of the body. Some examples of a diuretic may include hydrochlorothiazide, spironolactone, mannitol, and/or glucose. An expectorant may include an agent for stimulating the flow of saliva, loosening and thinning mucus in airways, and/or promoting a more productive cough as to eliminate phlegm from the respiratory tract. An example of an expectorant may include guaifenesin. A hormone may include molecules produced naturally by the endocrine glands. Some examples of a hormone may include steroid hormones, amine-derived hormones, peptide hormones, and/or lipid and phospholipid-derived hormones. A hypoglycemic may include an agent for lowering the level of glucose in the blood. Some examples of a hypoglycemic may include a sulfonylurea, a meglitinide, a biguanide, a thiazolidinedione, and/or a alpha-glucosidase inhibitor. An immunosuppressive may include an agent for preventing or reducing the body's normal reaction to invasion by disease and/or foreign tissues. Some examples of an immunosuppressive may include a drug such as a corticosteroid, cyclosporine, rapamycin, which acts on immunophilins, and/or an antibody.

A laxative may include an agent for increasing the frequency and ease of bowel movements. Some examples of a laxative may include methylcellulose, docusate, mineral oil, and/or magnesium hydroxide. A muscle relaxant may include an agent utilized for relieving muscle spasms. Some examples of a muscle relaxant may include neuromuscular blocking drugs, carisoprodol, cyclobenzaprine, metaxalone, a benzodiazepine and/or a tranquilizer. A sedative may include a substance which depresses the central nervous system and may result in calmness, relaxation, reduction of anxiety, sleepiness, and/or slowed breathing. Some examples of a sedative may include zolpidem, and/or eszopiclone. A female sex hormone may include a hormone responsible for the development of female secondary sexual characteristics. Some examples of a female sex hormone may include estrogen and progesterone. A male sex hormone may include a hormone responsible for the development of secondary male sexual characteristics. One example of a male sex hormone may include testosterone. Sex hormone-related agents may include agents metabolically related to sex hormones. Examples of sex hormone-related agents may include sterols, androgens (testosterone), progestogens estrogens (estradiols, estrone), follicle-stimulating hormone, luteinizing hormone, inhibin B, anti-Mullerian hormone thyroid-related hormones. A tranquilizer may include any drug having a calming and/or sedative effect. Some examples of a tranquilizer may include an antidepressant, a barbiturate, and/or a benzodiazepine. An appetite modulator may include an agent used for regulating and/or adjusting appetite. Some examples of an appetite modulator may include recombinant PYY 3-36 and/or sibutramine. A vitamin may include chemicals essential in relatively small quantities for good health. Some examples of a vitamin may include Vitamin A, Vitamin C, Vitamin D, and/or Vitamin K.

In one instance, selector module 106 can select an analgesic and an antipsychotic for subsequent presentation, perhaps in response to accepting a pain symptom and a hallucination symptom as the at least one attribute. In some instances, selector module 106 may include a computer processor.

Figure 18:
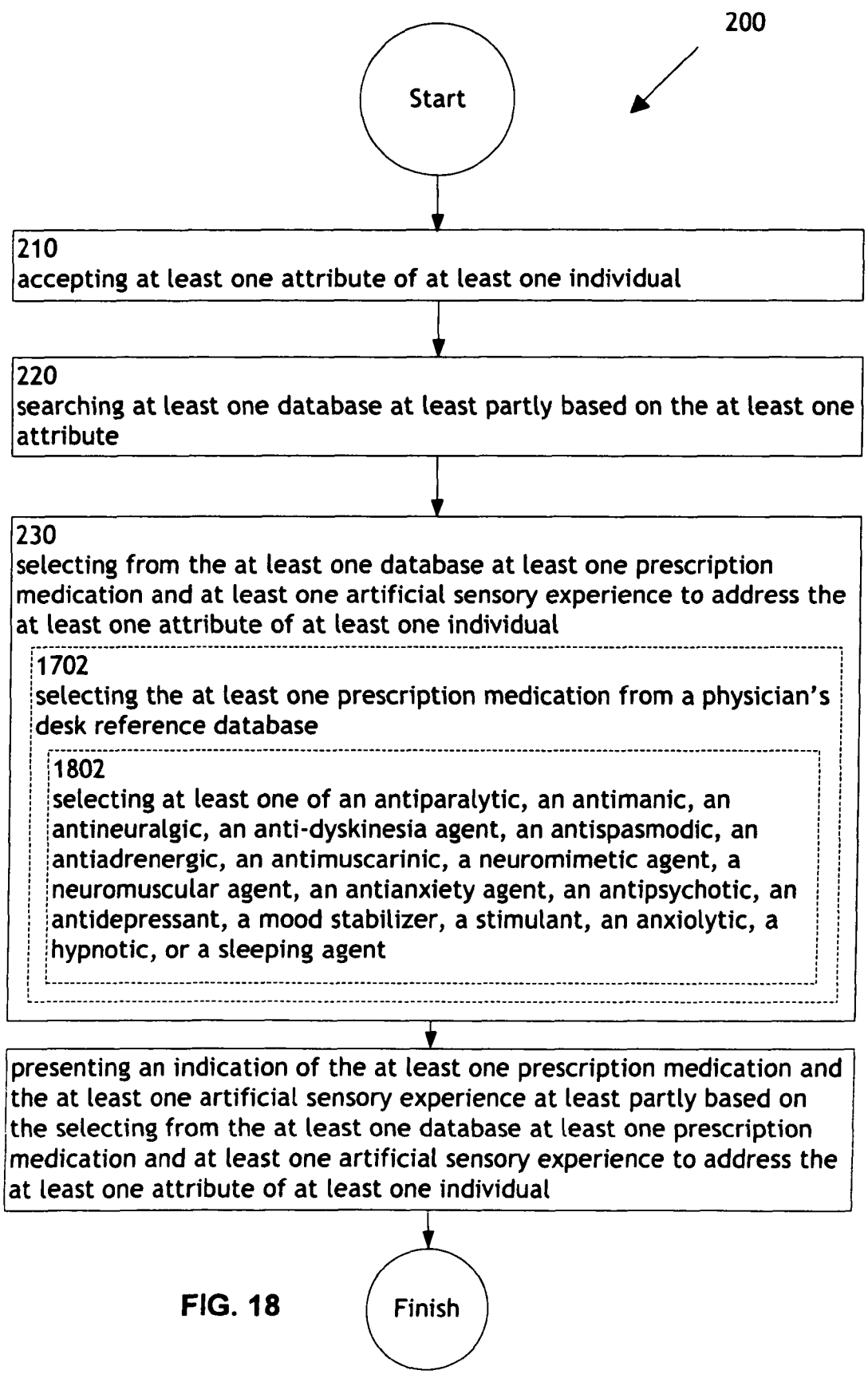
FIG. 18 illustrates an alternative embodiment of the operational flow of FIG. 2.

FIG. 18 illustrates alternative embodiments of the example operational flow 200 of FIG. 2. FIG. 18 illustrates example embodiments where operation 230 may include at least one additional operation. Additional operations may include an operation 1802. Further, operation 1802 illustrates selecting at least one of an antiparalytic, an antimanic, an antineuralgic, an anti-dyskinesia agent, an antispasmodic, an antiadrenergic, an antimuscarinic, a neuromimetic agent, a neuromuscular agent, an antianxiety agent, an antipsychotic, an antidepressant, a mood stabilizer, a stimulant, an anxiolytic, a hypnotic, or a sleeping agent. For example, as shown in FIG. 1, selector module 106 may select at least one of an antiparalytic, an antimanic, an antineuralgic, an anti-dyskinesia agent, an antispasmodic, an antiadrenergic, an antimuscarinic, a neuromimetic agent, a neuromuscular agent, an antianxiety drug, an antipsychotic, an antidepressant, a mood stabilizer, a stimulant, an anxiolytic, a hypnotic, and/or a sleeping agent such as a long-acting barbiturate. In one example, selector module 106 selects an antianxiety drug and a steeping agent. An antiparalytic may include an agent used for preventing the loss of and/or recovering muscle function. One example of an antiparalytic may include methylprednisolone. An antimanic may include an agent used for treating and/or suppressing mania. Some examples may include lamotrigine and/or carbamazepine. An antineuralgic may include an agent for relieving paroxysmal nerve pain. One example of an antineuralgic may include carbamazepine. An anti-dyskinesia agent may include an agent used for reducing and/or preventing dyskinesia, including involuntary muscle movement. One example of an anti-dyskinesia agent may include methylenedioxymethamphetamine. An antispasmodic may include a drug or an herb that suppresses smooth muscle contraction. Some examples of an antispasmodic may include dicyclomine and/or hyoscyamine. An antiadrenergic may include a medication for inhibiting the functioning of the sympathetic nervous system. Some examples of an antiadrenergic may include clonidine and/or mecamylamine. An antimuscarinic may include an agent for reducing the activity of the muscarinic acetylcholine receptor. Some examples of an antimuscarinic may include atropine and/or hyoscine. A neuromimetic agent may include an agent that mimics the response of an effector organ to nerve impulses. A neuromuscular agent may block neuromuscular transmission at the neuromuscular junction and cause paralysis of the affected skeletal muscles. Some examples of a neuromuscular agent may include atracurium and/or vecuronium. An antianxiety drug may include a drug for suppressing anxiety and relaxing the muscles. An antianxiety drug may include a sedative, a tranquilizer, an anxiolytic, such as a benzodiazepine, alprazolam and/or diazepam, an antidepressant, a short-acting barbiturate, and/or an herbal treatment, such as chamomile, kava extract, Kratom, and/or valerian. An antipsychotic may include a group of drugs commonly used to treat psychosis and may include phenothiazines, thioxanthenes, butyrophenones, risperidone, amisulpride, and/or other suitable drugs. An antidepressant may include a psychiatric medication or other substance, such as a nutrient or herb, used for alleviating depression or dysthymia. Some examples of an antidepressant may include a selective serotonin reuptake inhibitor, such as Prozac and/or Zoloft, and/or a serotonin-norepinephrine reuptake inhibitor, such as Cymbalta. A mood stabilizer may include a psychiatric medication used to treat mood disorders characterized by intense and sustained mood shifts. Some examples of a mood stabilizer may include lithium carbonate and/or lamotrigine. A stimulant may include substances that may temporarily increase alertness and awareness, such as caffeine, ephedrine, and/or nicotine. An anxiolytic may include a substance used for the treatment of anxiety, such as a benzodiazepine and/or a barbiturate. A hypnotic may include substances that induce sleep, such as a barbiturate and/or an antihistamine (diphenhydramine). A sleeping agent may include any number of medications for helping a person sleep and/or stay asleep and may include benzodiazepines, antidepressants, melatonin, and/or antihistamines as well as other suitable substances. In some instances, selector module 106 may include a computer processor.

Figure 19:
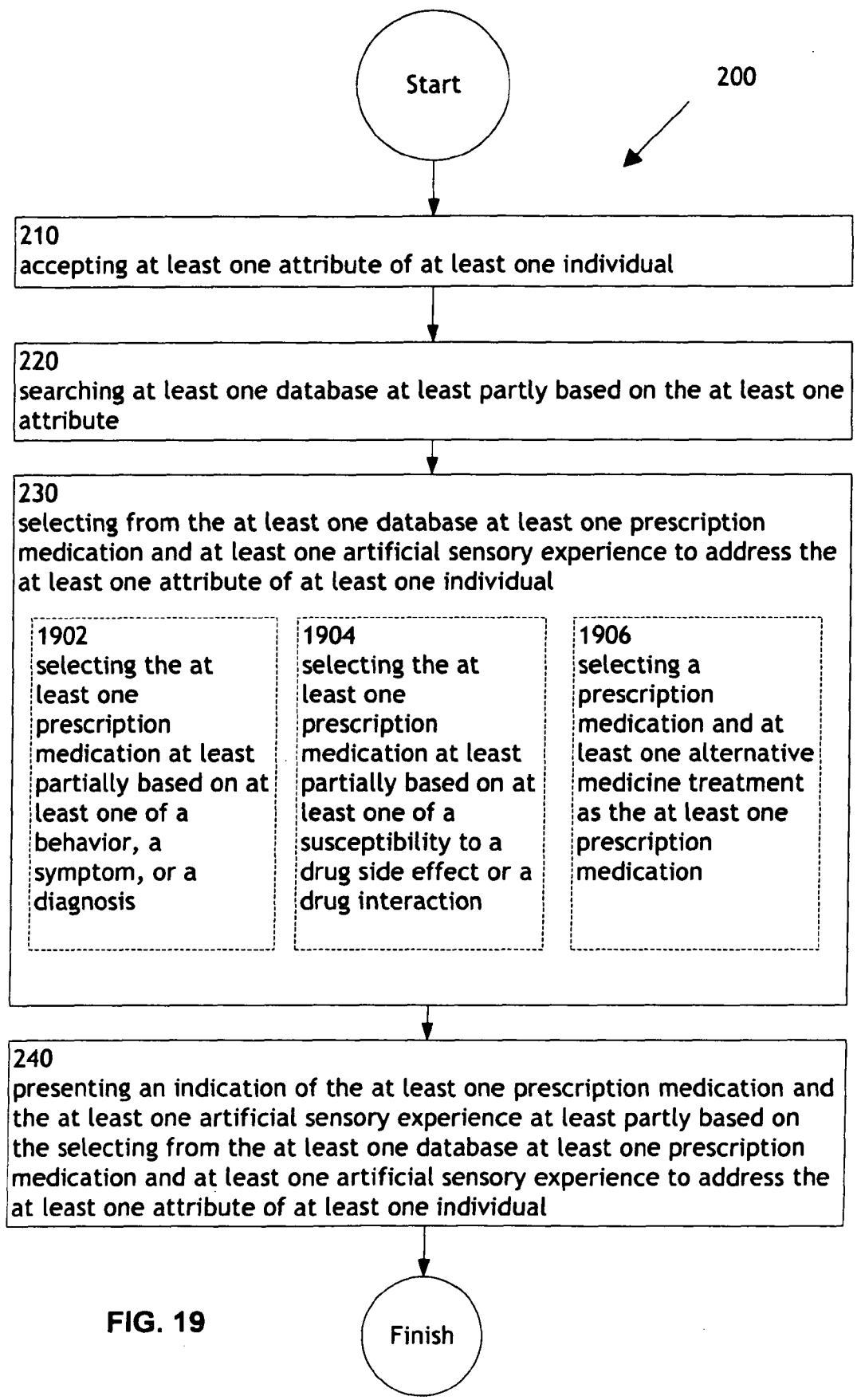
FIG. 19 illustrates an alternative embodiment of the operational flow of FIG. 2.

FIG. 19 illustrates alternative embodiments of the example operational flow 200 of FIG. 2. FIG. 19 illustrates example embodiments where operation 230 may include at least one additional operation. Additional operations may include an operation 1902, an operation 1904, and/or an operation 1906.

Operation 1902 illustrates selecting the at least one prescription medication at least partially based on at least one of a behavior, a symptom, or a diagnosis. For example, as shown in FIG. 1, selector module 106 may select the at least one prescription medication at least partially based on at least one of a behavior, a symptom, or a diagnosis. In one instance, selector module 106 can select a prescription medication based on a diagnosis. A behavior may include the manner a person behaves toward other people and/or a certain circumstance. A symptom may include a subjective indicator of a health problem reported by an individual, or a sign of a health problem noticed by another, perhaps a doctor. A symptom may be evidence of a disease, a disability, an impairment, and/or a condition. A diagnosis may include an identification of a disease, a disability, an impairment, and/or a condition. In some instances, selector module 106 may include a computer processor.

Operation 1904 illustrates selecting the at least one prescription medication at least partially based on at least one of a susceptibility to a drug side effect or a drug interaction. For example, as shown in FIG. 1, selector module 106 may select the at least one prescription medication at least partially based on at least one of a susceptibility to a drug side effect or a drug interaction. In one instance, selector module 106 can select a prescription medication based on a susceptibility to a drug side effect including an allergy. A susceptibility to a drug side effect may include a probability a certain person may be vulnerable to a side effect associated with a specific drug and/or medication. A susceptibility to a drug side effect may include predisposition to a particular drug side effect or class of drug side effects, such as upset stomach associated with aspirin formulations. A drug reaction may include a possible response a person may exhibit resulting from at least one drug and/or medication administered to the person. A drug reaction may include an allergy and/or a drug and/or medication interaction with a separate drug and/or medication. In some instances, selector module 106 may include a computer processor.

Operation 1906 illustrates selecting a prescription medication and at least one alternative medicine treatment as the at least one prescription medication. For example, as shown in FIG. 1, selector module 106 may select a prescription medication and at least one alternative medicine treatment as the at least one prescription medication. In one instance, selector module 106 can select a prescription medication and at least one alternative medicine treatment as the at least one prescription medication. A prescription medication may include a medication, drug, and/or treatment available only with written instructions from a doctor, dentist, and/or other licensed professional. An alternative medicine treatment may include medical and/or nutraceutical treatments and/or practices utilized instead of standard medical treatments. Some examples of alternative medicine treatments may include chiropractic, herbal medicine, acupuncture, homeopathy, naturopathy, and/or spiritual devotions. In some instances, selector module 106 may include a computer processor.

Figure 20:
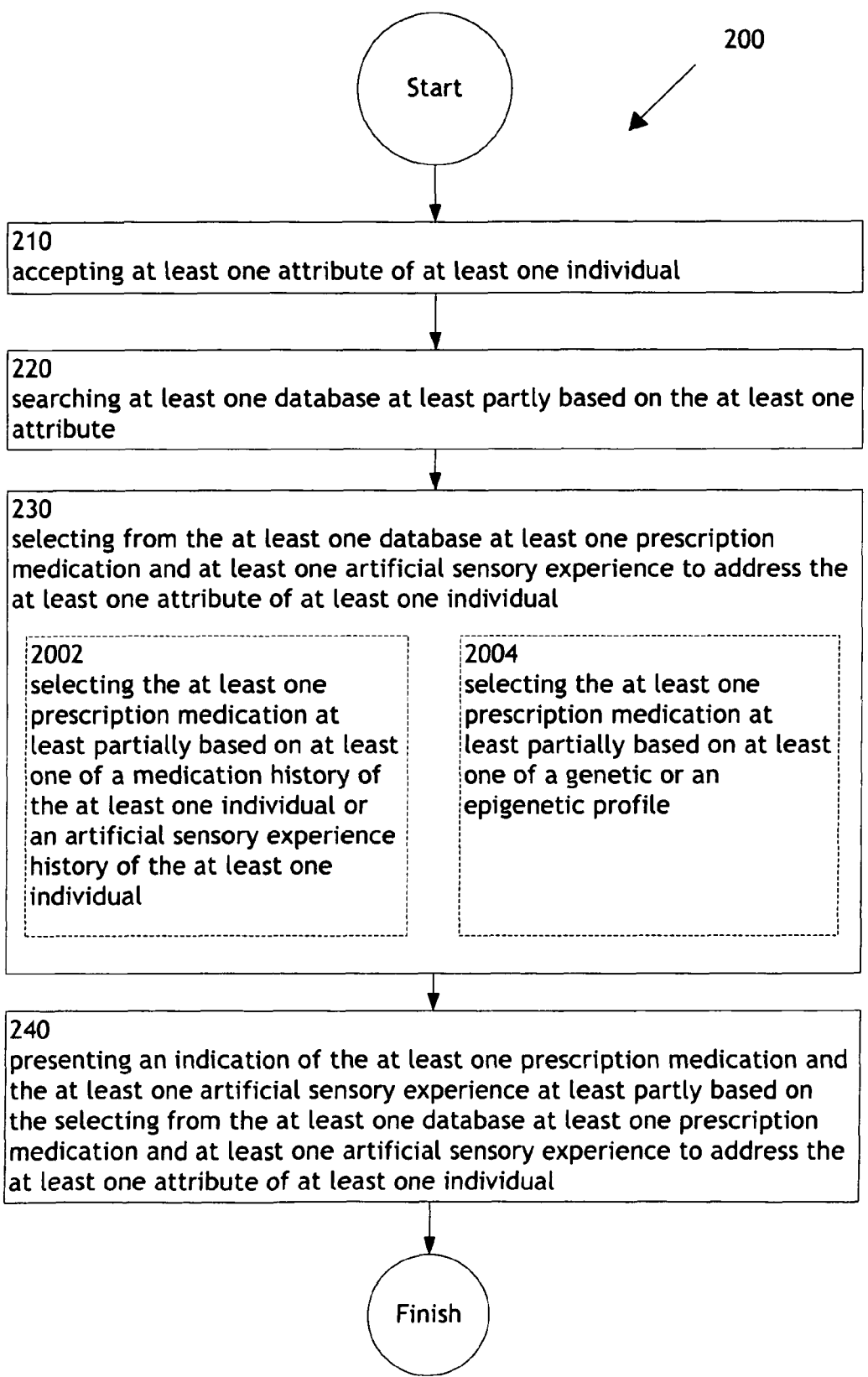
FIG. 20 illustrates an alternative embodiment of the operational flow of FIG. 2.

FIG. 20 illustrates alternative embodiments of the example operational flow 200 of FIG. 2. FIG. 20 illustrates example embodiments where operation 230 may include at least one additional operation. Additional operations may include an operation 2002, and/or an operation 2004.

Operation 2002 illustrates selecting the at least one prescription medication at least partially based on at least one of a medication history of the at least one individual or an artificial sensory experience history of the at least one individual. For example, as shown in FIG. 1, selector module 106 may select the at least one prescription medication at least partially based on at least one of a medication history of the at least one individual or an artificial sensory experience history of the at least one individual. In one example, selector module 106 can select a prescription medication based on a medication history of an individual named Jennifer Harris or an anonymous individual. A medication history may include any record of administered medications and/or drugs that may exist for an individual. An artificial sensory experience history may include any record of an artificial sensory experience associated with an individual. In some instances, selector module 106 may include a computer processor.

Operation 2004 illustrates selecting the at least one prescription medication at least partially based on at least one of a genetic or an epigenetic profile. For example, as shown in FIG. 1, selector module 106 may select the at least one prescription medication at least partially based on at least one of a genetic or an epigenetic profile. In one instance, selector module 106 can select a prescription medication based on a genetic profile. A genetic profile may include hereditary information encoded in the genetic sequence of an individual. An epigenetic profile may include information regarding chromatin and/or DNA modifications that are stable over rounds of cell division but do not involve changes in the underlying DNA sequence of the organism, such as histone acetylation and/or DNA methylation. Other epigenetic information may be found in higher-order chromatin structure. In some instances, selector module 106 may include a computer processor.

Figure 21:
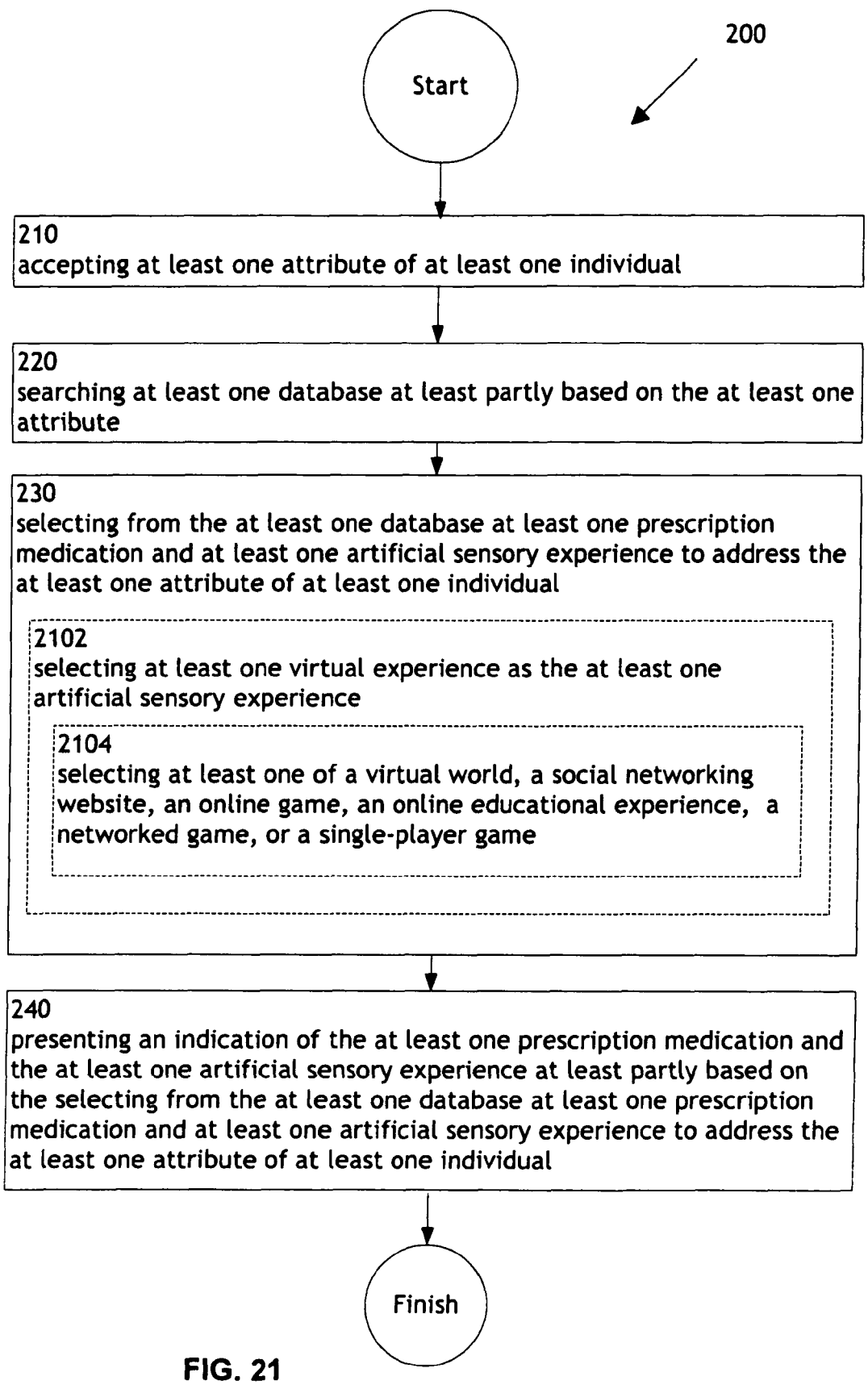
FIG. 21 illustrates an alternative embodiment of the operational flow of FIG. 2.

FIG. 21 illustrates alternative embodiments of the example operational flow 200 of FIG. 2. FIG. 21 illustrates example embodiments where operation 230 may include at least one additional operation. Additional operations may include an operation 2102, and/or an operation 2104.

Operation 2102 illustrates selecting at least one virtual experience as the at least one artificial sensory experience. For example, as shown in FIG. 1, selector module 106 may select at least one virtual experience as the at least one artificial sensory experience. In one example, selector module 106 can select a virtual experience as the artificial sensory experience. A virtual experience may include an experience with a computer-simulated environment. Such a virtual experience may be interactive or non-interactive. Some examples of a virtual experience may include an experience with a virtual world, a simulated reality, a computer game, and/or a virtual tour, and may involve input devices such as a keyboard, a mouse, an accelerometer-containing input device, and/or a wired glove. A virtual experience may also involve a visual and/or auditory monitoring device such as a video monitor, goggles, loudspeakers, or the like. Examples of a virtual experience include second life, snow world, or the like. In some instances, selector module 106 may include a computer processor.

Operation 2104 illustrates selecting at least one of a virtual world, a social networking website, an online game, an online educational experience, a networked game, or a single-player game. For example, as shown in FIG. 1, selector module 106 may select at least one of a virtual world, a social networking website, an online game, an online educational experience, a networked game, or a single-player game. In one instance, selector module 106 can select a virtual world. A virtual world may include a computer-based simulated environment intended for its users to inhabit and interact via avatars, such as second life. A social networking website may include a website for observing and/or interacting with one or more personal and/or professional relationships between individuals. Some examples of a social networking website may include MySpace, GeoCities, Facebook, and/or LinkedIn. In one instance, selector module 106 may select Facebook as the social networking website and may include directions to Facebook to implement a color scheme including bright colors, such as yellow and light blue, for preventing the onset of depression in a depression prone viewer. An online game may include a game played over a network, such as hardwired terminals, a wireless network, a modem network, a video console, and/or the internet. Some online games may include virtual worlds and/or virtual communities. Examples of online games may include World of Warcraft (WoW), Final Fantasy XI, Lineage II, Guild Wars, and/or RuneScape. An online educational experience may include a tutorial, a lesson, and/or an online class. Some examples of an online educational experience may include a HTML tutorial, an online piano lesson, and/or an online degree program from the University of Phoenix. A networked game may include any game played by more than one player and may be played on a computer. An example of a networked game may include World of Warcraft (WoW). A single-player game may include any game that can be played by one player and that may or may not be played on a computer. Examples of a single-player game include solitaire, puzzle games such as Tetris, Call of Duty, and Guitar Hero. In some instances, selector module 106 may include a computer processor.

Figure 22:
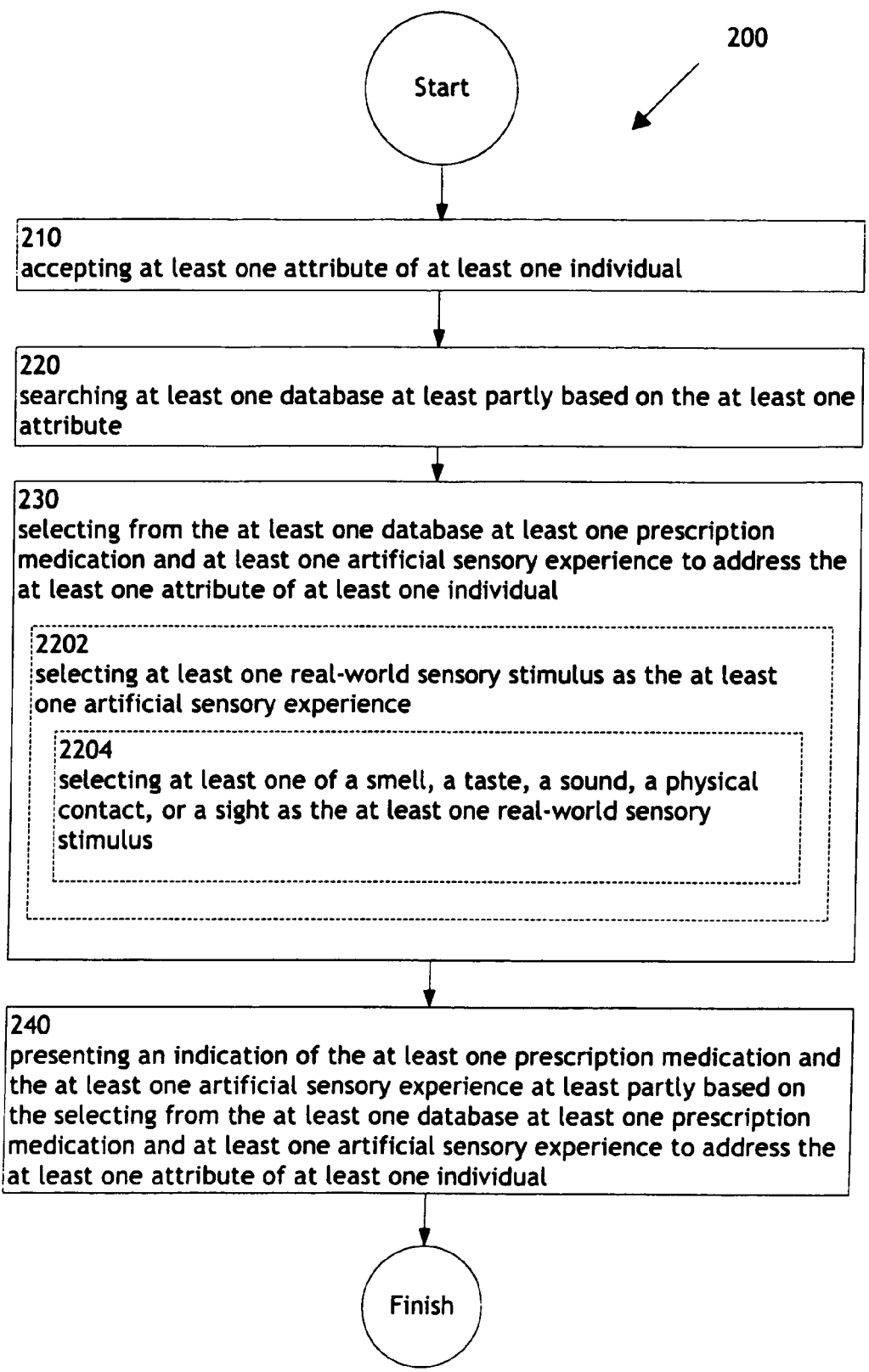
FIG. 22 illustrates an alternative embodiment of the operational flow of FIG. 2.

FIG. 22 illustrates alternative embodiments of the example operational flow 200 of FIG. 2. FIG. 22 illustrates example embodiments where operation 230 may include at least one additional operation. Additional operations may include an operation 2202, and/or an operation 2204.

Operation 2202 illustrates selecting at least one real-world sensory stimulus as the at least one artificial sensory experience. For example, as shown in FIG. 1, selector module 106 may select at least one real-world sensory stimulus as the at least one artificial sensory experience. In one instance, selector module 106 can select a real-world sensory stimulus including an aroma as an artificial sensory experience. Some examples of a real-world sensory stimulus may include aromas and/or smells, sounds, sights, touch, pressure, temperature and/or heat, and/or vibration. In some instances, selector module 106 may include a computer processor. Further, operation 2204 illustrates selecting at least one of a smell, a taste, a sound, a physical contact, or a sight as the at least one real-world sensory stimulus. For example, as shown in FIG. 1, selector module 106 may select at least one of a smell, a taste, a sound, a physical contact, or a sight as the at least one real-world sensory stimulus. In one example, selector module 106 selects a smell and a taste as a real-world sensory stimulus. A smell may include any property detected by the nose and/or olfactory system. A taste may include any flavor and/or property detected by the tongue and/or taste buds. A sound may include any sound wave that may be detected by the eardrum. A physical contact may include anything related to touch, feel, and/or detection by the skin and/or body, and/or physical activity including exercise. In one instance, selector module 106 may select a physical contact including physical exercise associated with participating in playing a tennis game on a Nintendo Wii video game console, for example. A sight may include any image, and/or light detected by the eyes. In some instances, selector module 106 may include a computer processor.

Figure 23:
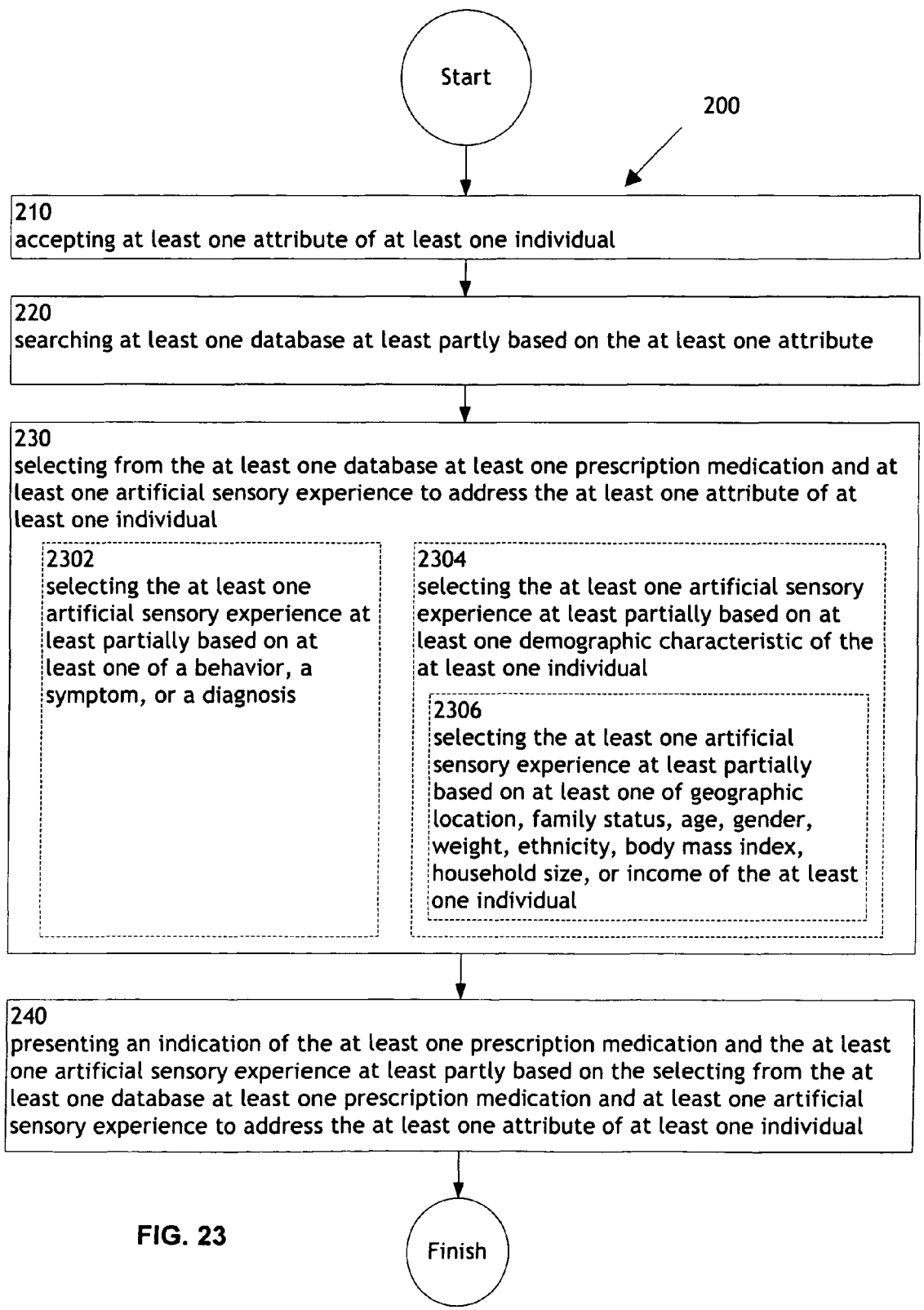
FIG. 23 illustrates an alternative embodiment of the operational flow of FIG. 2.

FIG. 23 illustrates alternative embodiments of the example operational flow 200 of FIG. 2. FIG. 23 illustrates example embodiments where operation 230 may include at least one additional operation. Additional operations may include an operation 2302, an operation 2304, and/or an operation 2306.

Operation 2302 illustrates selecting the at least one artificial sensory experience at least partially based on at least one of a behavior, a symptom, or a diagnosis. For example, as shown in FIG. 1, selector module 106 may select the at least one artificial sensory experience at least partially based on at least one of a behavior, a symptom, or a diagnosis. In one example, selector module 106 can select an artificial sensory experience based on behavior entered by a user 118 via a user interface 116. A behavior may include the manner in which a person and/or thing acts and/or reacts. A symptom may include a manifestation, sign, and/or an indication of the presence of a disease and/or some other disorder and/or abnormality. A diagnosis may include identifying a disease and/or condition by its signs and/or symptoms. For example, selector module 106 and/or system 100 may select an immersive virtual reality experience as the at least one artificial sensory experience at least partially based on a pain symptom and/or a third-degree burn diagnosis. In some instances, selector module 106 may include a computer processor.

Operation 2304 illustrates selecting the at least one artificial sensory experience at least partially based on at least one demographic characteristic of the at least one individual. For example, as shown in FIG. 1, selector module 106 may select the at least one artificial sensory experience at least partially based on at least one demographic characteristic of the at least one individual. In one example, selector module 106 can select an artificial sensory experience based on a demographic characteristic the at least one individual. A demographic characteristic may include a socioeconomic, age, gender, and/or other similar factor defining a certain population. For example, selector module 106 and/or system 100 may select a virtual reality experience such as a Sesame Street or Disney-themed experience as the at least one artificial sensory experience at least partially based on an indication that the individual is aged 6-10 years old. In some instances, selector module 106 may include a computer processor.

Further, operation 2306 illustrates selecting the at least one artificial sensory experience at least partially based on at least one of geographic location, family status, age, gender, weight, ethnicity, body mass index, household size, or income of the at least one individual. For example, as shown in FIG. 1, selector module 106 may select the at least one artificial sensory experience at least partially based on at least one of geographic location, family status, age, gender, weight, ethnicity, body mass index, household size, or income of the at least one individual. In one example, selector module 106 can select the artificial sensory experience based on an age and a weight associated with the at least one individual. A geographic location may include a location where an individual currently resides, has resided in the past, and/or has visited. A family status may include marital status, status and/or presence of children, and/or the status and/or health of extended family. In some instances, selector module 106 may include a computer processor.

Figure 24:
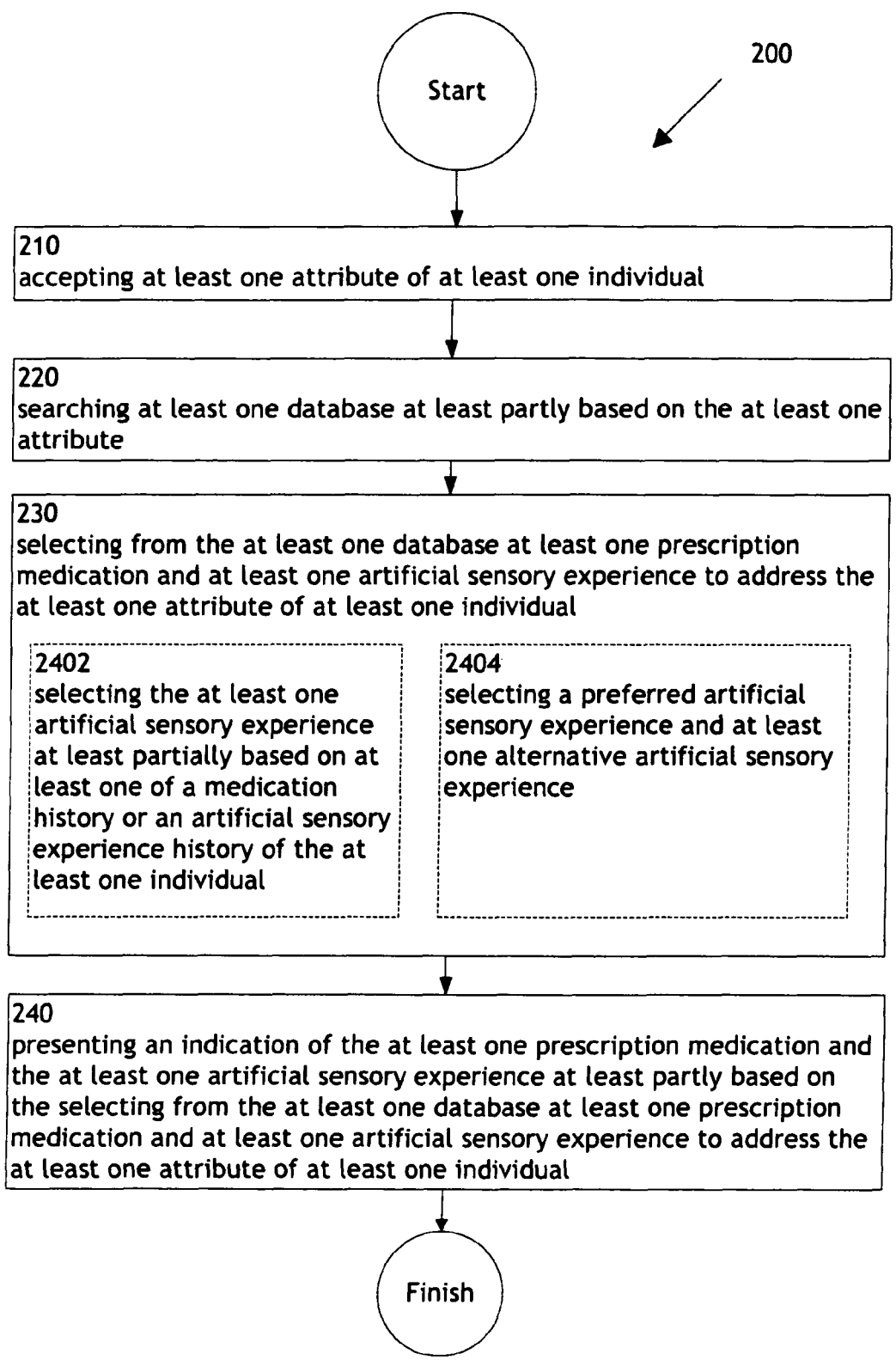
FIG. 24 illustrates an alternative embodiment of the operational flow of FIG. 2.

FIG. 24 illustrates alternative embodiments of the example operational flow 200 of FIG. 2. FIG. 24 illustrates example embodiments where operation 230 may include at least one additional operation. Additional operations may include an operation 2402, and/or an operation 2404.

Operation 2402 illustrates selecting the at least one artificial sensory experience at least partially based on at least one of a medication history or an artificial sensory experience history of the at least one individual. For example, as shown in FIG. 1, selector module 106 may select the at least one artificial sensory experience at least partially based on at least one of a medication history or an artificial sensory experience history of the at least one individual. In one instance, selector module 106 can select an artificial sensory experience based on an artificial sensory experience history of the at least one individual. An artificial sensory experience history may include any record of at least one administered artificial sensory experience history. For example, system 100 and/or selector module 106 may select a modified facebook webpage having a cheerful color scheme at least partly based on a facebook usage history for an individual with signs of depression. In some instances, selector module 106 may include a computer processor.

Operation 2404 illustrates selecting a preferred artificial sensory experience and at least one alternative artificial sensory experience. For example, as shown in FIG. 1, selector module 106 may select a preferred artificial sensory experience and at least one alternative artificial sensory experience. In one example, selector module 106 can select a preferred artificial sensory experience and at least one alternative artificial sensory experience. A preferred artificial sensory experience may include a more desirable artificial sensory experience due to a lack of and/or a reduced level of side effects, reduced impact upon the individual, and/or increased compatibility with another medications and/or treatment. An alternative artificial sensory experience may include any artificial sensory experience in addition to the preferred artificial sensory experience and may be less desirable than the preferred artificial sensory experience due to side effects and/or increased impact upon the individual. In some instances, selector module 106 may include a computer processor.

Figure 25:
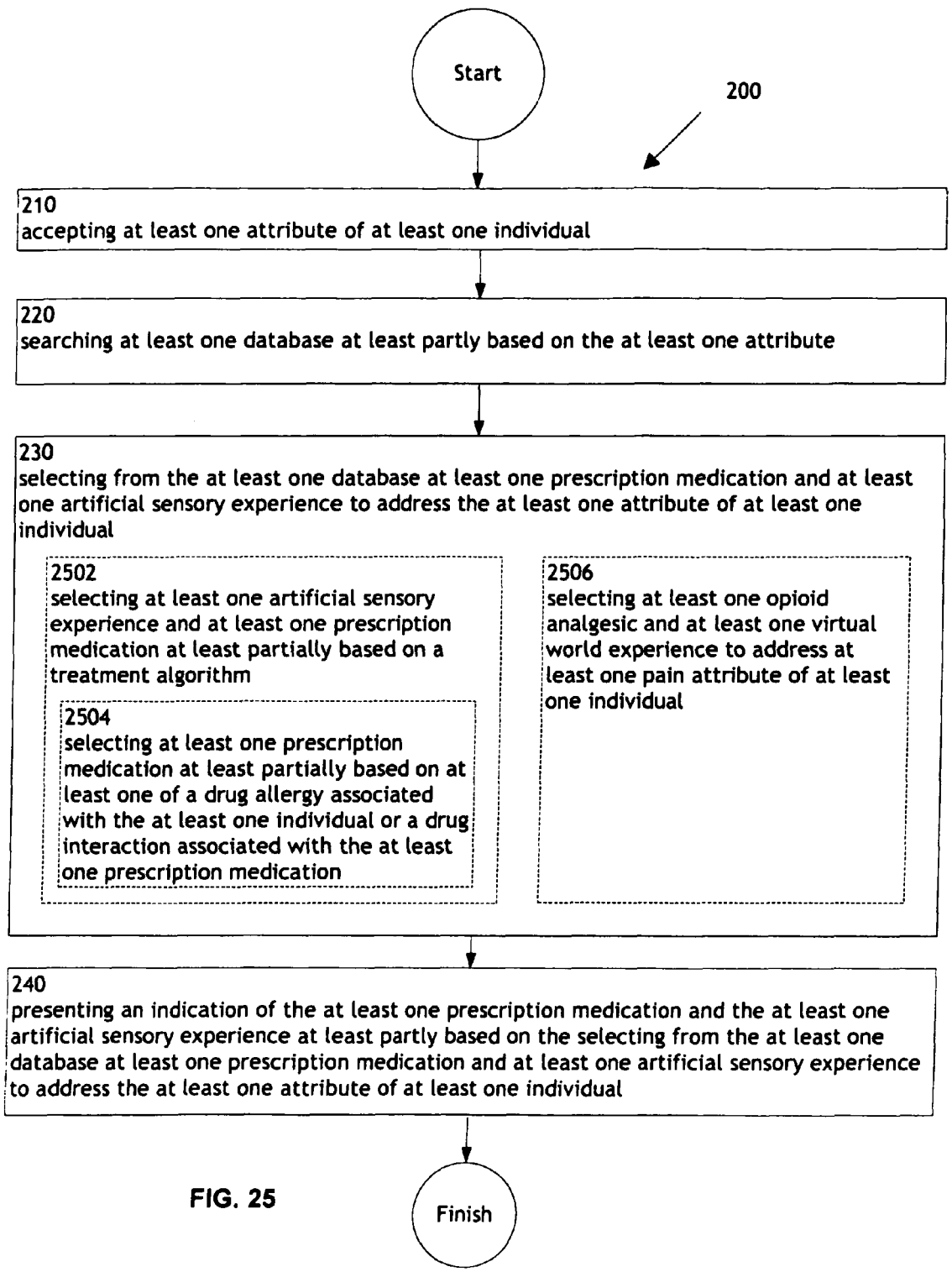
FIG. 25 illustrates an alternative embodiment of the operational flow of FIG. 2.

FIG. 25 illustrates alternative embodiments of the example operational flow 200 of FIG. 2. FIG. 25 illustrates example embodiments where operation 230 may include at least one additional operation. Additional operations may include an operation 2502, an operation 2504, and/or an operation 2506.

Operation 2502 illustrates selecting at least one artificial sensory experience and at least one prescription medication at least partially based on a treatment algorithm. For example, as shown in FIG. 1, selector module 106 may select at least one artificial sensory experience and at least one prescription medication at least partially based on a treatment algorithm. In one instance, selector module 106 can select an artificial sensory experience and a prescription medication based on a computer software treatment algorithm. A treatment algorithm may include any computation, formula, statistical survey, and/or look-up table for determining and/or selecting a suitable artificial sensory experience and prescription medication combination. Some examples may include a computer software algorithm, a calculator, a flowchart, and/or a decision tree. For example, system 100 and/or selector module 106 may, based on an accepted pain symptom of an individual, access a lookup chart that matches the pain symptom with a pain medication, such as naproxen, and a virtual experience, such as World of Warcraft. Such a combination therapy may be particularly effective in ameliorating the pain symptom in the individual. In some instances, selector module 106 may include a computer processor.

Further, operation 2504 illustrates selecting at least one prescription medication at least partially based on at least one of a drug allergy associated with the at least one individual or a drug interaction associated with the at least one prescription medication. For example, as shown in FIG. 1, selector module 106 may select at least one prescription medication at least partially based on at least one of a drug allergy associated with the at least one individual or a drug interaction associated with the at least one prescription medication. In one example, selector module 106 can select a prescription medication based on a drug allergy associated with the at least one individual. A drug allergy may include any allergy to a drug and/or drug intolerance. Some examples of a drug allergy may include penicillin allergies, codeine allergies, and/or allergies to a dye in a drug. A drug interaction may include an undesirable and/or unwanted reaction between two or more drugs and/or medications. For example, the system 100 and/or selector module 106 can select a prescription medication other than those that might cause a side effect in an individual, perhaps because of a known predisposition to the side effect (e.g., an allergy) or because of a known drug-drug interaction relevant to the individual based on the individual's medication regimen. In this way, risk of side effects can be lessened. In some instances, selector module 106 may include a computer processor.

Operation 2506 illustrates selecting at least one opioid analgesic and at least one virtual world experience to address at least one pain attribute of at least one individual. For example, as shown in FIG. 1, selector module 106 may select from a prescription medication database at least one opioid analgesic and at least one virtual world experience to address at least one pain attribute of at least one individual. In one example, selector module 106 can select an opioid analgesic including morphine and a virtual world experience including an online game to address a pain attribute of at least one individual named Mary Andersen. In some instances, selector module 106 may include a computer processor.

Figure 26:
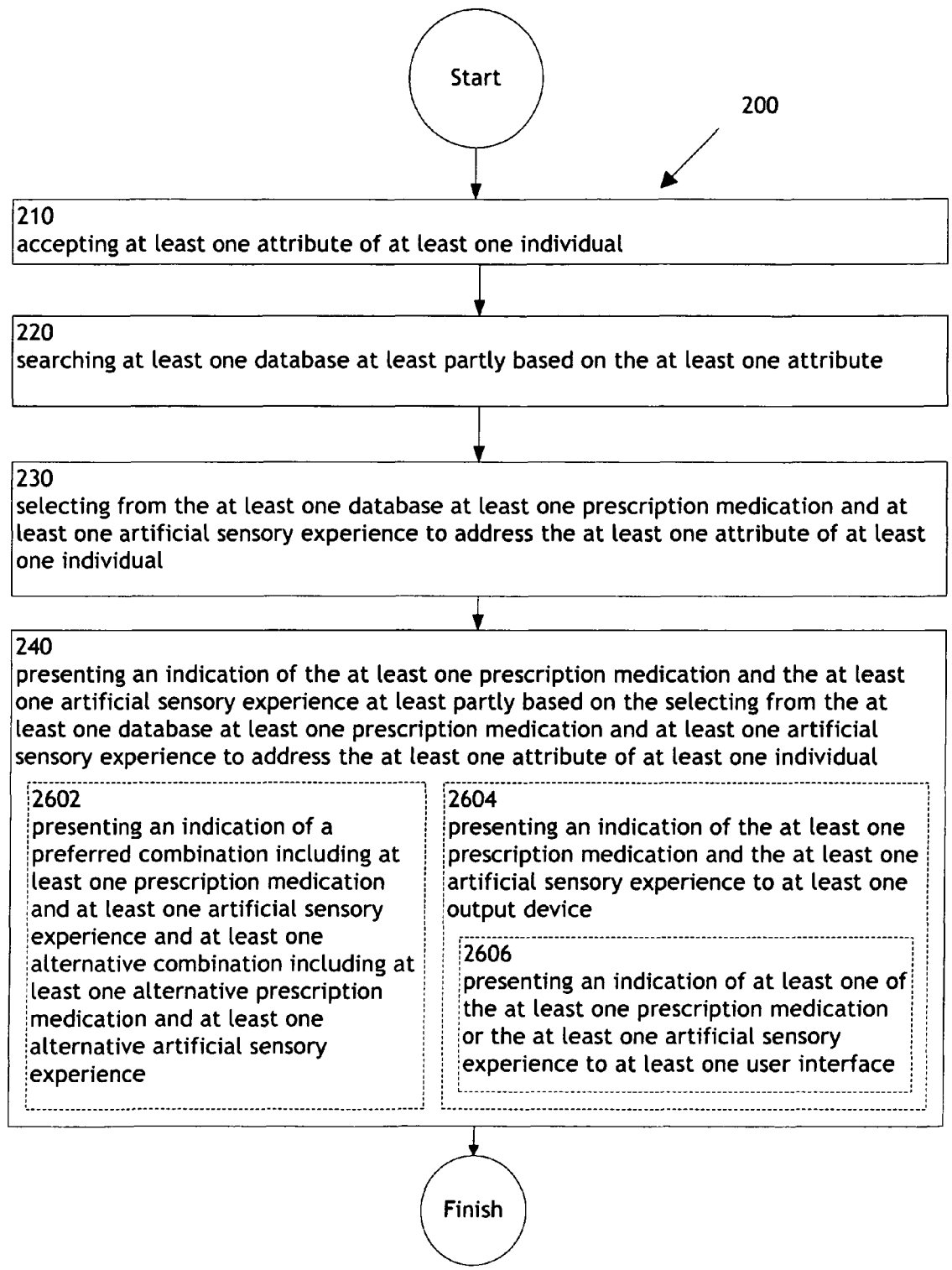
FIG. 26 illustrates an alternative embodiment of the operational flow of FIG. 2.

FIG. 26 illustrates alternative embodiments of the example operational flow 200 of FIG. 2. FIG. 26 illustrates example embodiments where operation 240 may include at least one additional operation. Additional operations may include an operation 2602, an operation 2604, and/or an operation 2606.

Operation 2602 illustrates presenting an indication of a preferred combination including at least one prescription medication and at least one artificial sensory experience and at least one alternative combination including at least one alternative prescription medication and at least one alternative artificial sensory experience. For example, as shown in FIG. 1, presenter module 108 may present an indication of a preferred combination including at least one prescription medication and at least one artificial sensory experience and at least one alternative combination including at least one alternative prescription medication and at least one alternative artificial sensory experience. In one instance, presenter module 108 can present an indication of a preferred combination to an individual 134 including a prescription medication and an artificial sensory experience along with an alternative combination including an alternative prescription medication and an alternative artificial sensory experience. Individual 134 may include a single individual, multiple individuals, and/or an entity. A preferred combination may include a more desirable combination due to a lack of and/or a reduced number of and/or level of side effects, reduced impact upon the administered individual, and/or increased compatibility with another medications and/or treatment. An alternative combination may include any combination in addition to the preferred combination and may be ostensibly less desirable than the preferred artificial sensory experience because of a potential side effect and/or impact upon the administered individual. Presentation of alternative combinations may provide benefits to the individual in terms of accessibility, affordability, and/or personal preference of medication and/or artificial sensory experience. In some instances, presenter module 108 may include a computer processor.

Operation 2604 illustrates presenting an indication of the at least one prescription medication and the at least one artificial sensory experience to at least one output device. For example, as shown in FIG. 1, presenter module 108 may present an indication of the at least one prescription medication and the at least one artificial sensory experience to at least one output device. In one example, presenter module 108 can present an indication of a prescription medication and an artificial sensory experience to an output device 130 including a printer at a health clinic. An output device may include any hardware device configured for receiving computer output. Some examples of an output device may include a printer, a monitor, a mobile phone, a speaker, and/or a visual display unit. The output device may be used by individual 134. In some instances, presenter module 108 may include a computer processor.

Further, operation 2606 illustrates presenting an indication of at least one of the at least one prescription medication or the at least one artificial sensory experience to at least one user interface. For example, as shown in FIG. 1, presenter module 108 may present an indication of at least one of the at least one prescription medication or the at least one artificial sensory experience to at least one user interface. In one instance, presenter module 108 can present an indication of a prescription medication and an artificial sensory experience to a user interface. A user interface may include means by which an individual may interact with a system. Some examples of a user interface may include a touchscreen, a graphical user interface, a tactile interface, and/or a live user interface. In some instances, presenter module 108 may include a computer processor.

Figure 27:
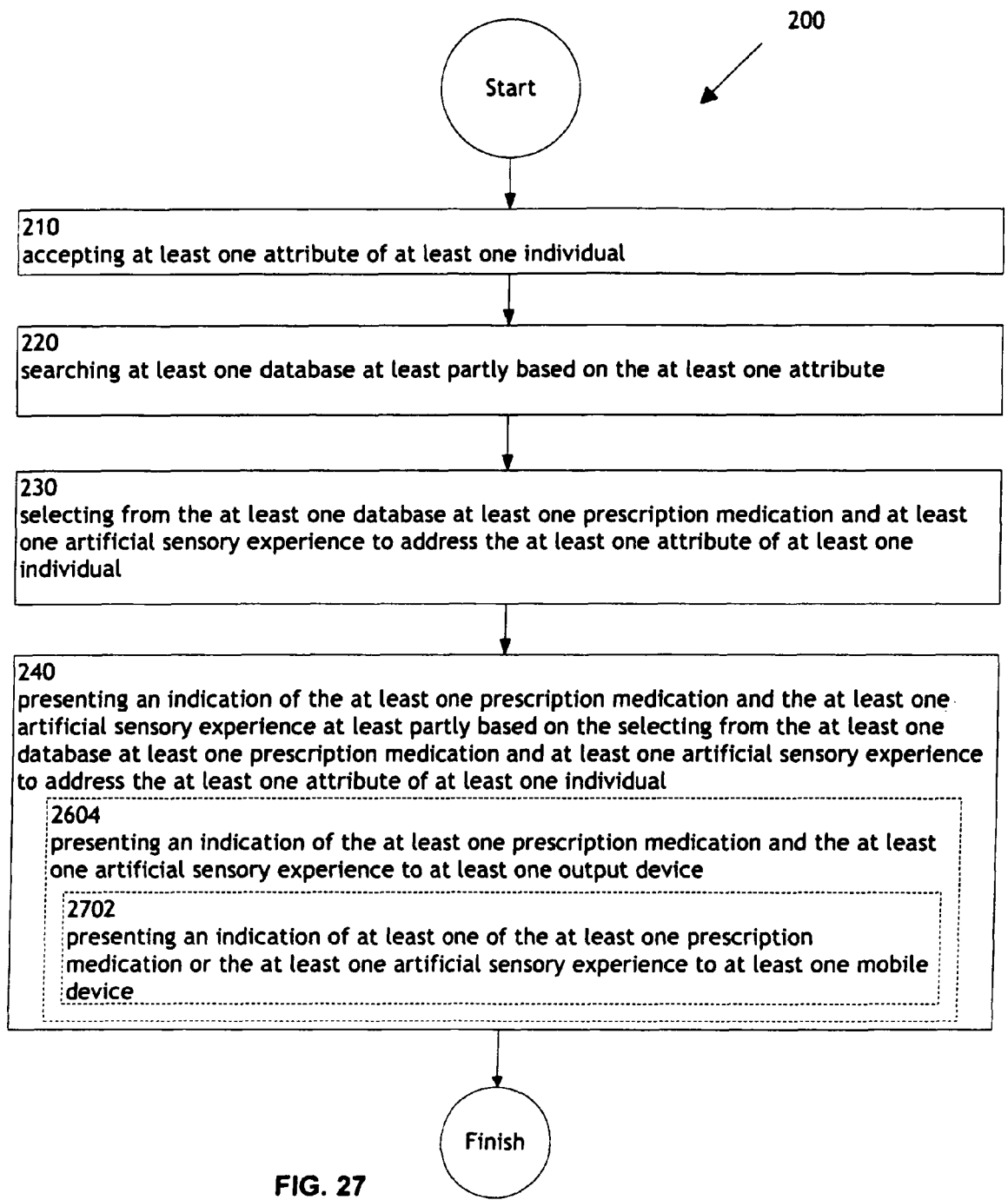
FIG. 27 illustrates an alternative embodiment of the operational flow of FIG. 2.

FIG. 27 illustrates alternative embodiments of the example operational flow 200 of FIG. 2. FIG. 27 illustrates example embodiments where operation 240 may include at least one additional operation. Additional operations may include an operation 2702. Further, operation 2702 illustrates presenting an indication of at least one of the at least one prescription medication or the at least one artificial sensory experience to at least one mobile device. For example, as shown in FIG. 1, presenter module 108 may present an indication of at least one of the at least one prescription medication or the at least one artificial sensory experience to at least one mobile device. In one instance, presenter module 108 can present an indication of a prescription medication to a mobile device 132. A mobile device may include a portable computing device and may have wireless connection capability. Some examples of a mobile device may include a laptop or notebook computer, a personal digital assistant (PDA), an ipod, a smartphone, an Enterprise digital assistant (EDA), and/or a pager. In some instances, presenter module 108 may include a computer processor.

Figure 28:
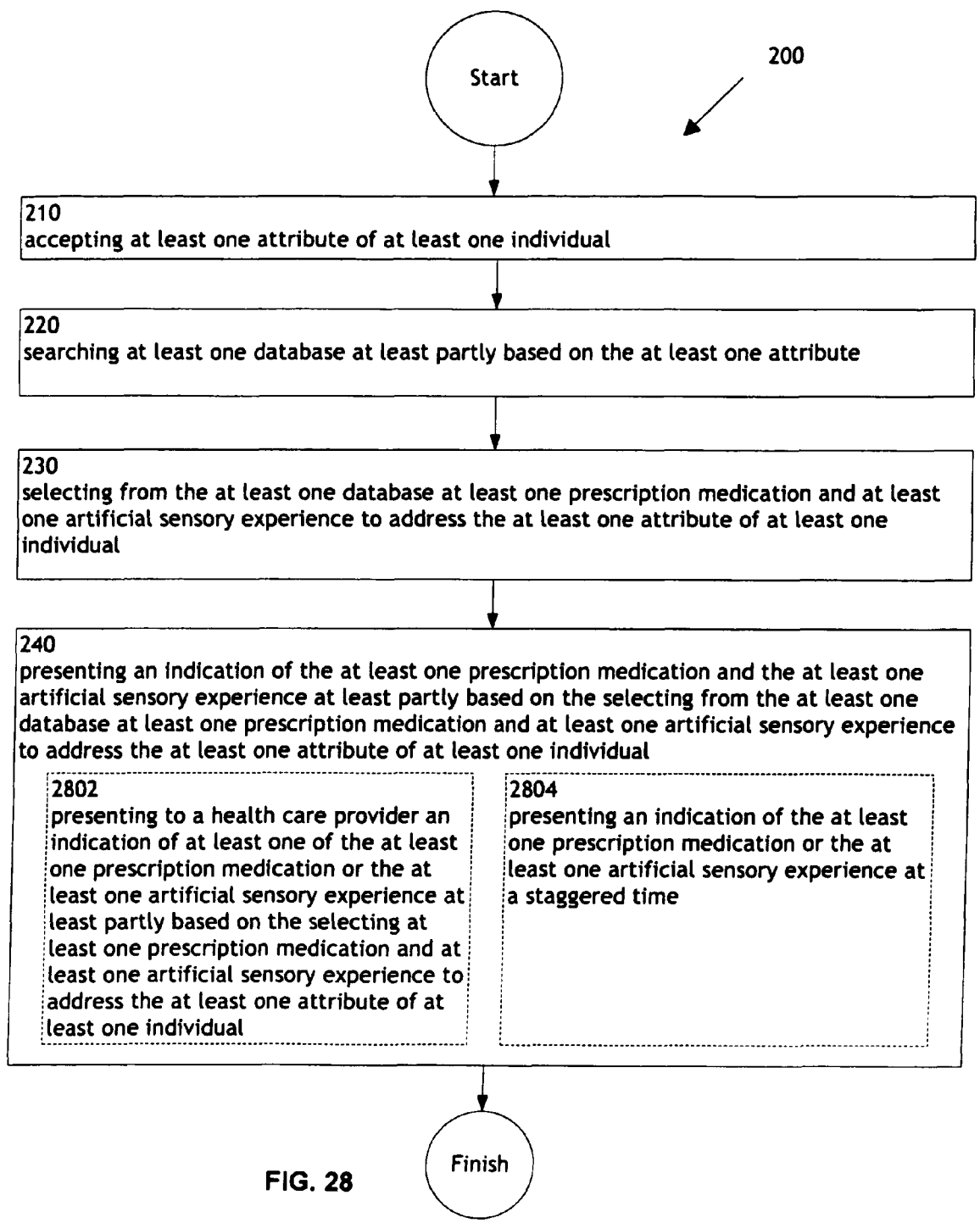
FIG. 28 illustrates an alternative embodiment of the operational flow of FIG. 2.

FIG. 28 illustrates alternative embodiments of the example operational flow 200 of FIG. 2. FIG. 28 illustrates example embodiments where operation 240 may include at least one additional operation. Additional operations may include an operation 2802, and/or an operation 2804.

Operation 2802 illustrates presenting to a health care provider an indication of at least one of the at least one prescription medication or the at least one artificial sensory experience at least partly based on the selecting at least one prescription medication and at least one artificial sensory experience to address the at least one attribute of at least one individual. For example, as shown in FIG. 1, presenter module 108 may present to a health care provider an indication of at least one of the at least one prescription medication or the at least one artificial sensory experience at least partly based on the selecting at least one prescription medication and at least one artificial sensory experience to address an attribute of an individual. In one example, presenter module 108 can present to a health care provider 128 an indication of a prescription medication based on the selecting at least one prescription medication and at least one artificial sensory experience to address the at least one attribute 120 of at least one individual. A health care provider may include a pharmacy, a pharmaceutical company, a medical device company, a research institution, a computer software and/or computer hardware company, a website, a nurse and/or a physician. In some instances, presenter module 108 may include a computer processor.

Operation 2804 illustrates presenting an indication of the at least one prescription medication or the at least one artificial sensory experience at a staggered time. For example, as shown in FIG. 1, presenter module 108 may present an indication of at least one of the at least one prescription medication or the at least one artificial sensory experience at a staggered time. In one example, presenter module 108 can present an indication of a series of prescription medications and an artificial sensory experience at staggered times. A staggered time may include presenting an indication of the at least one drug and/or artificial sensory experience at overlapping times and/or at different times, including alternating times. For example, at least one drug and an artificial sensory experience may be administered at an initial time and the same or a different drug may be administered when the first-administered at least one drug is at its peak effect. In another example, at least one drug and an artificial sensory experience may be administered at an initial time and the same or a different drug may be administered when the first administered at least one drug is at its lowest effect. In another example, an artificial sensory experience may be administered at an initial time and at least one prescription medication at a later time. The at least one artificial sensory experience and/or the at least one prescription medication may be administered at any number of times either concurrently, partially concurrently, or not concurrently. In some instances, presenter module 108 may include a computer processor.

Figure 29:
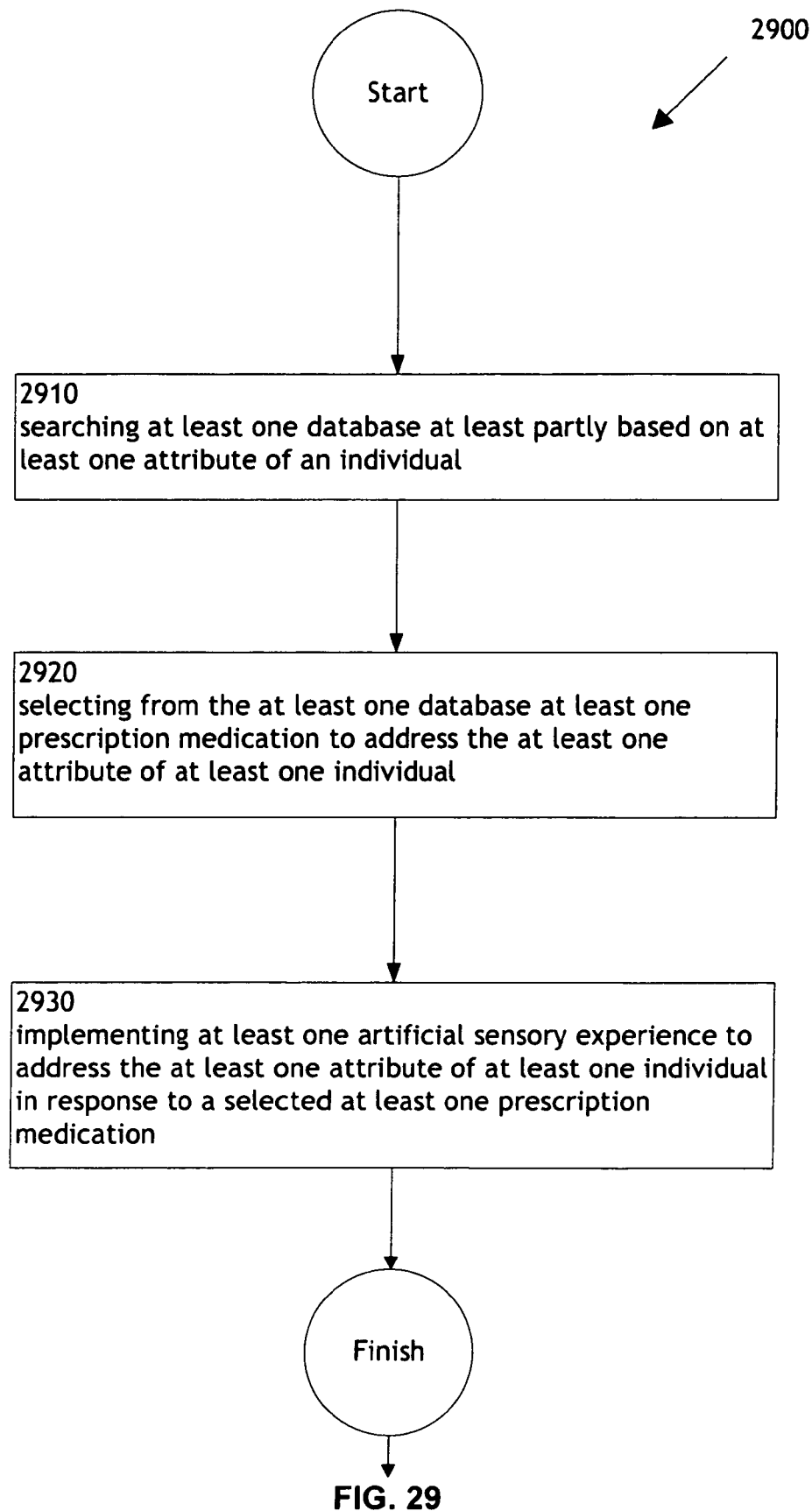
FIG. 29 illustrates an operational flow representing example operations related to selecting a combination of at least one prescription medication and at least one artificial sensory experience.

FIG. 29 illustrates an operational flow 2900 representing example operations related to querying at least one database at least partly based on at least one attribute of an individual, selecting from the at least one database at least one prescription medication to address the at least one attribute of at least one individual, and/or implementing at least one artificial sensory experience to address the at least one attribute of at least one individual in response to a selected at least one prescription medication. In FIG. 29, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 2900 moves to an operation 2910. Operation 2910 depicts querying at least one database at least partly based on at least one attribute of an individual. For example, as shown in FIG. 1, querier module 104 may search at least one database at least partly based on at least one attribute of an individual. In one instance, querier module 104 may search medication database 124 and artificial sensory experience database 126 based on an attribute 120 including an indication of hypertension associated with an individual named John Smith. In some instances, querier module 104 may include a computer processor.

Then, operation 2920 depicts selecting from the at least one database at least one prescription medication to address the at least one attribute of at least one individual. For example, as shown in FIG. 1, selector module 106 may select from the at least one database at least one prescription medication to address the at least one attribute of at least one individual. In one example and continuing with the previous example, selector module 106 may select from medication database 124 and artificial sensory experience database 126 a prescription medicine for addressing the attribute 120 including an indication of hypertension associated with an individual named John Smith. In some instances, selector module 106 may include a computer processor.

Then, operation 2930 depicts implementing at least one artificial sensory experience to address the at least one attribute of at least one individual in response to a selected at least one prescription medication. For example, as shown in FIG. 1, implementer module 138 may implement at least one artificial sensory experience to address the at least one attribute of at least one individual in response to a selected at least one prescription medication. In one instance and continuing with the previous example, implementer module 106 may implement an artificial sensory experience including a virtual world for addressing the attribute 120 including an indication of hypertension associated with an individual named John Smith in response to a selected prescription medication from a medication database 124. In some instances, selector module 106 may include a computer processor.

Figure 30:
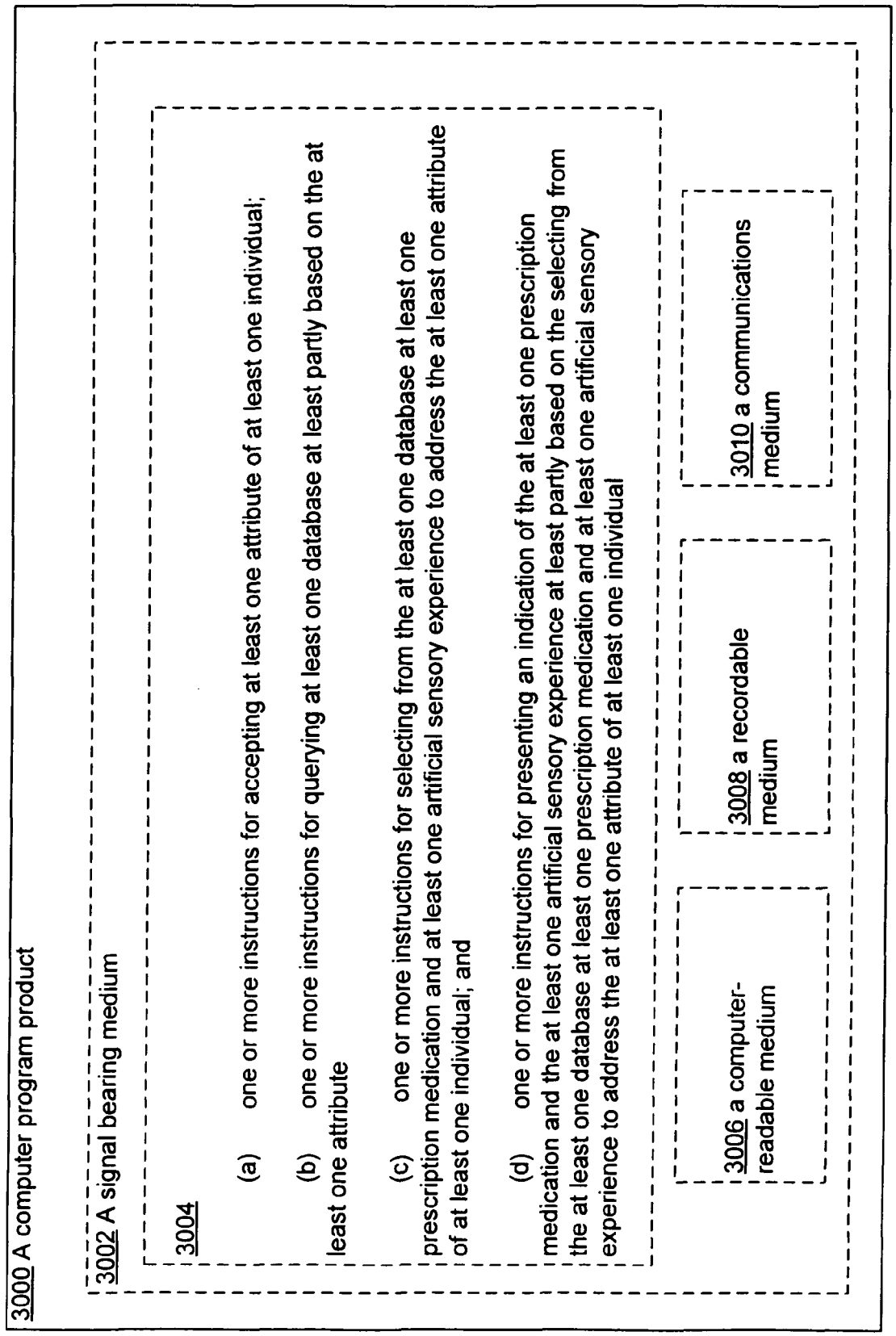
FIG. 30 illustrates a computer program product related to selecting a combination of at least one prescription medication and at least one artificial sensory experience.

FIG. 30 illustrates a partial view of an example computer program product 3000 that includes a computer program 3004 for executing a computer process on a computing device. An embodiment of the example computer program product 3000 is provided using a signal-bearing medium 3002, and may include one or more instructions for accepting at least one attribute of at least one individual; one or more instructions for querying at least one database at least partly based on the at least one attribute; one or more instructions for selecting from the at least one database at least one prescription medication and at least one artificial sensory experience to address the at least one attribute of at least one individual; and one or more instructions for presenting an indication of the at least one prescription medication and the at least one artificial sensory experience at least partly based on the selecting from the at least one database at least one prescription medication and at least one artificial sensory experience to address the at least one attribute of at least one individual. The one or more instructions may be, for example, computer executable and/or logic-implemented instructions. In one implementation, the signal-bearing medium 3002 may include a computer-readable medium 3006. In one implementation, the signal bearing medium 3002 may include a recordable medium 3008. In one implementation, the signal bearing medium 3002 may include a communications medium 3010.

Figure 31:
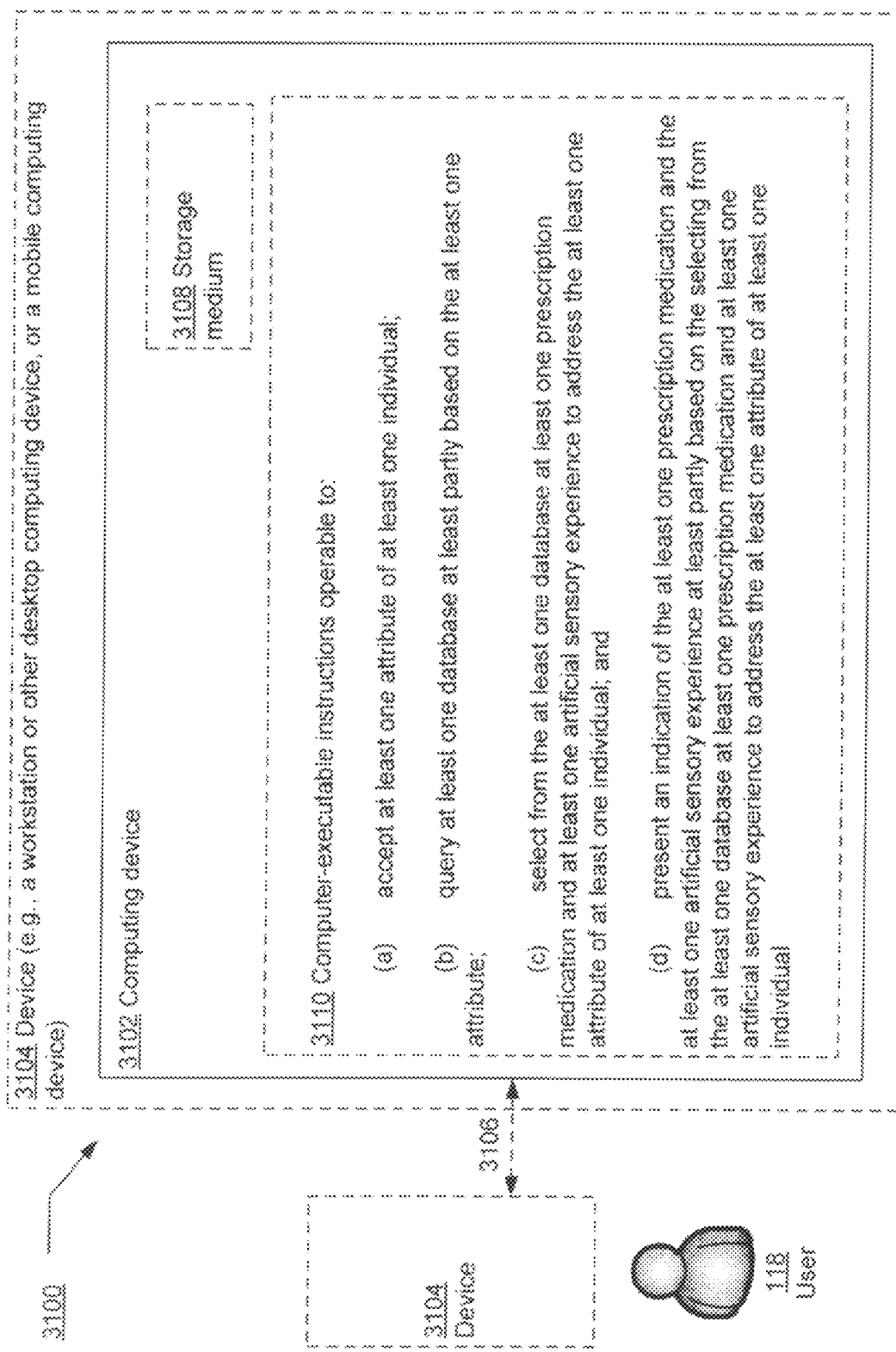
FIG. 31 illustrates a system related to selecting a combination of at least one prescription medication and at least one artificial sensory experience.

FIG. 31 illustrates an example system 3100 in which embodiments may be implemented. The system 3100 includes a computing system environment. The system 3100 also illustrates the user 118 using a device 3104, which is optionally shown as being in communication with a computing device 3102 by way of an optional coupling 3106. The optional coupling 3106 may represent a local, wide-area, or peer-to-peer network, or may represent a bus that is internal to a computing device (e.g., in example embodiments in which the computing device 3102 is contained in whole or in part within the device 3104). A storage medium 3108 may be any computer storage media.

The computing device 3102 includes computer-executable instructions 3110 that when executed on the computing device 3102 cause the computing device 3102 to accept at least one attribute of at least one individual; query at least one database at least partly based on the at least one attribute; select from the at least one database at least one prescription medication and at least one artificial sensory experience to address the at least one attribute of at least one individual; and present an indication of the at least one prescription medication and the at least one artificial sensory experience at least partly based on the selecting from the at least one database at least one prescription medication and at least one artificial sensory experience to address the at least one attribute of at least one individual. As referenced above and as shown in FIG. 31, in some examples, the computing device 3102 may optionally be contained in whole or in part within the device 3104.

In FIG. 31, then, the system 3100 includes at least one computing device (e.g., 3102 and/or 3104). The computer-executable instructions 3110 may be executed on one or more of the at least one computing device. For example, the computing device 3102 may implement the computer-executable instructions 3110 and output a result to (and/or receive data from) the computing device 3104. Since the computing device 3102 may be wholly or partially contained within the computing device 3104, the device 3104 also may be said to execute some or all of the computer-executable instructions 3110, in order to be caused to perform or implement, for example, various ones of the techniques described herein, or other techniques.

The device 3104 may include, for example, a portable computing device, workstation, or desktop computing device. In another example embodiment, the computing device 3102 is operable to communicate with the device 3104 associated with the user 118 to receive information about the input from the user 118 for performing data access and data processing and presenting an output of the user-health test function at least partly based on the user data.

Although a user 118 is shown/described herein as a single illustrated figure, those skilled in the art will appreciate that a user 118 may be representative of a human user, a robotic user (e.g., computational entity), and/or substantially any combination thereof (e.g., a user may be assisted by one or more robotic agents). In addition, a user 118, as set forth herein, although shown as a single entity may in fact be composed of two or more entities. Those skilled in the art will appreciate that, in general, the same may be said of "sender" and/or other entity-oriented terms as such terms are used herein.

Figure 32A:
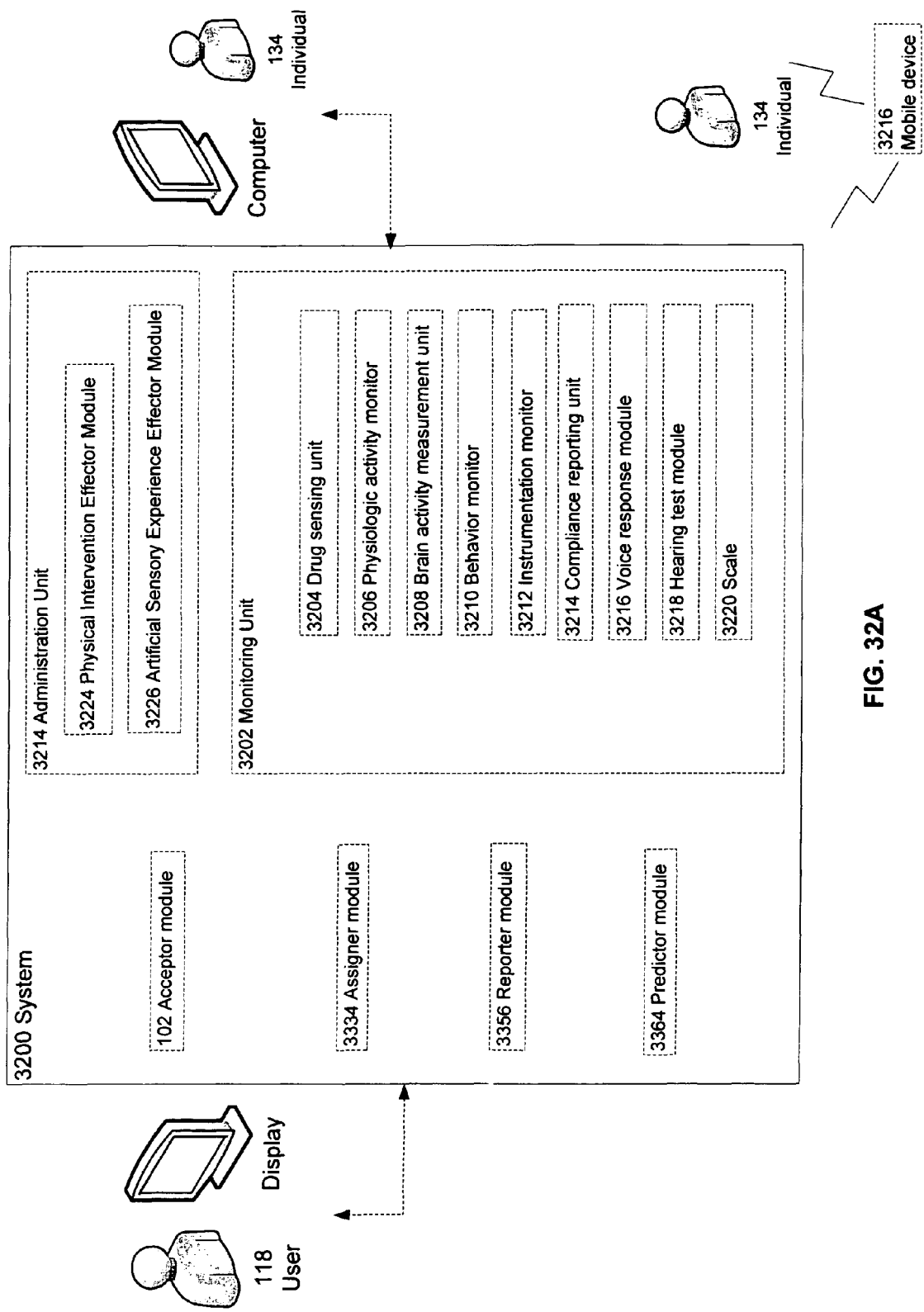
FIG. 32A illustrates an exemplary environment in which one or more technologies may be implemented.

FIG. 32A illustrates system 3200 for accepting at least one indication of a bioactive agent use by an individual, assigning an artificial sensory experience to monitor at least one desired effect of the bioactive agent on the individual, reporting at least one monitored effect, and/or predicting at least one effect of the bioactive agent when combined with the artificial sensory experience. The system 3200 may include acceptor module 102, assigner module 3334, monitoring unit 3202, reporter module 3356, predictor module 3364, and/or administration unit 3222.

Figure 32B:
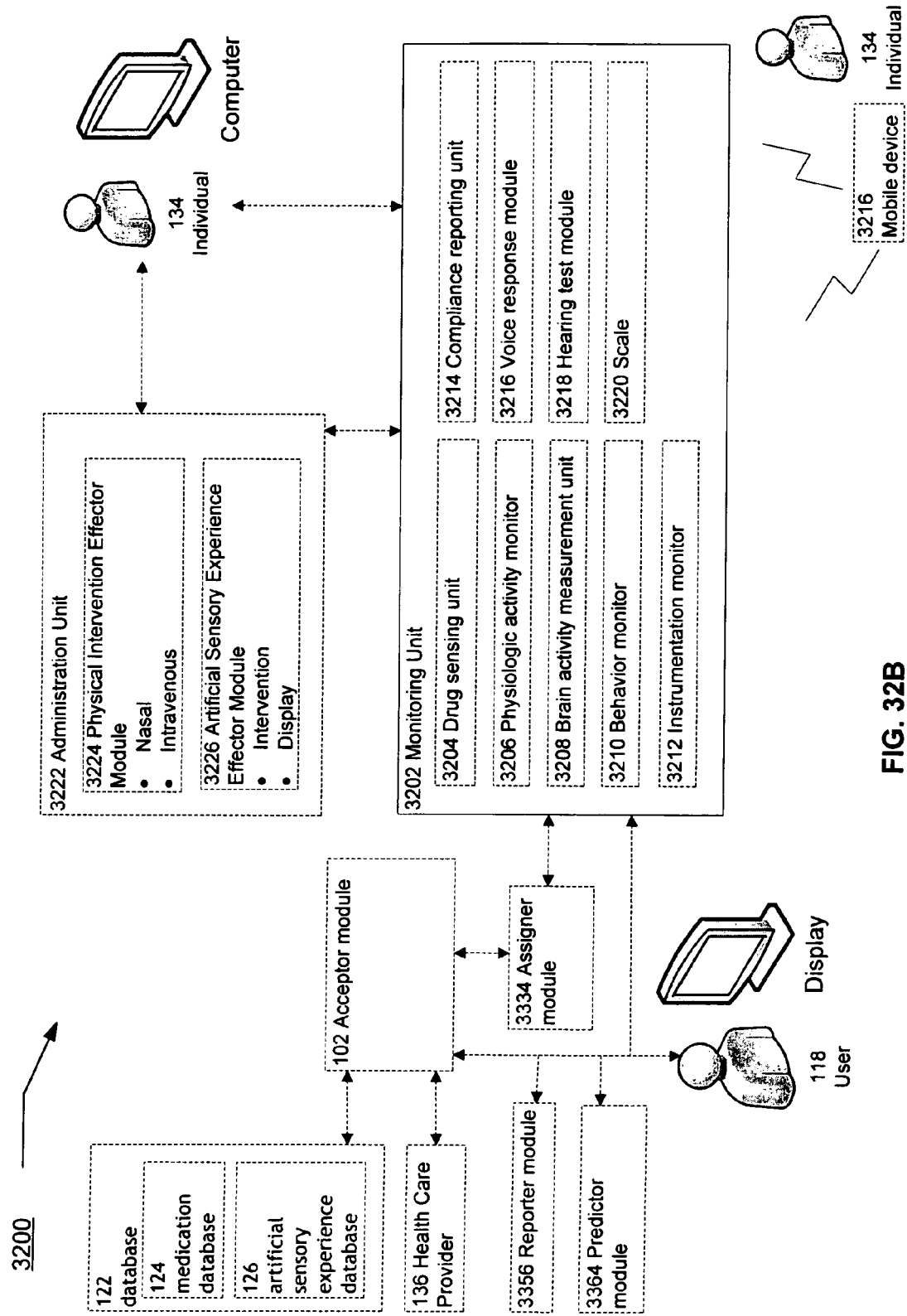
FIG. 32B illustrates an exemplary environment in which one or more technologies may be implemented.

FIG. 32B illustrates system 3200 for accepting at least one indication of a bioactive agent use by an individual, assigning an artificial sensory experience to monitor at least one desired effect of the bioactive agent on the individual, reporting at least one monitored effect, and/or predicting at least one effect of the bioactive agent when combined with the artificial sensory experience. The system 3200 may include acceptor module 102, assigner module 3334, monitoring unit 3202, reporter module 3356, predictor module 3364, and/or administration unit 3222. Accepter module 102 may receive information and/or data from user 118, database 122, and/or health care provider 136. Database 122 may include medication database 124 and/or artificial sensory experience database 126. Monitoring unit 3202 may monitor individual 134 and may include drug sensing unit 3204, physiologic activity monitor 3206, brain activity measurement unit 3208, behavior monitor 3210, instrumentation monitor 3212, compliance reporting unit 3214, voice response module 3216, hearing test module 3218, and/or scale 3220. Administration unit 3222 may include physical intervention effector module 3224 and/or artificial sensory experience effector module 3226.

Figure 33:
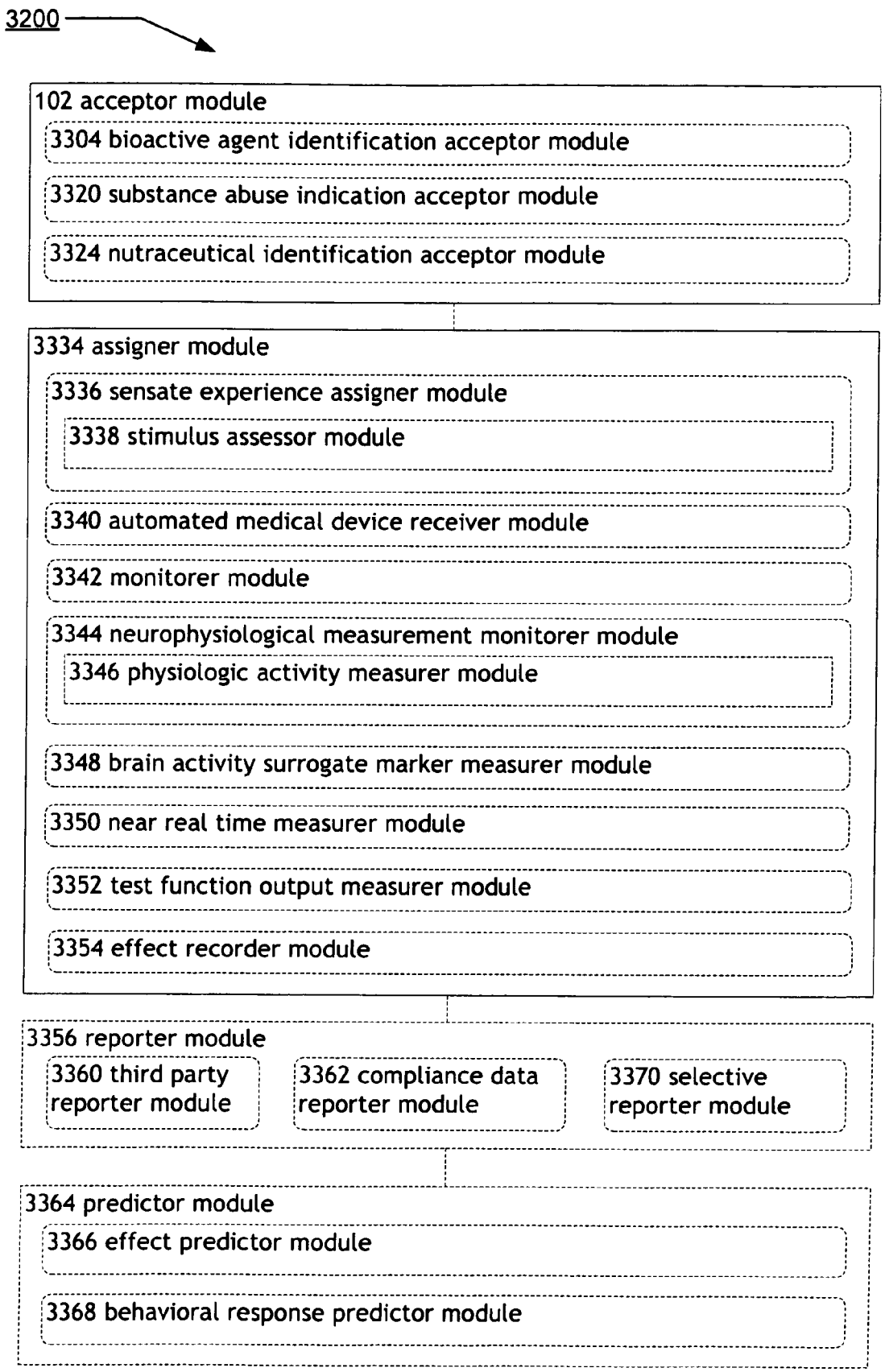
FIG. 33 illustrates an exemplary environment in which one or more technologies may be implemented.

FIG. 33 further illustrates system 3200 including acceptor module 102, assigner module 3334, reporter module 3356, and/or predictor module 3364. Acceptor module 102 may include bioactive agent identification accepter module 3304, substance abuse indication accepter module 3320, and/or nutraceutical identification accepter module 3324. Assigner module 3334 may include sensate experience assigner module 3336, automated medical device receiver module 3340, monitorer module 3342, neurophysiological measurement monitorer module 3344, brain activity surrogate marker measurer module 3348, near real time measurer module 3350, test function output measurer module 3352, and/or effect recorder module 3354. Sensate experience assigner module 3336 may include stimulus assigner module 3338. Neurophysiological measurement monitorer module 3344 may include physiologic activity measurer module 3346. Reporter module 3356 may include third party reporter module 3360, compliance data reporter module 3362, and/or selective reporter module 3370. Predictor module 3364 may include effect predictor module 3366 and/or behavioral response predictor module 3368.

System 3200 generally represents instrumentality for accepting at least one indication of a bioactive agent use by an individual, assigning an artificial sensory experience to monitor at least one desired effect of the bioactive agent on the individual, reporting at least one monitored effect, and/or predicting at least one effect of the bioactive agent when combined with the artificial sensory experience. The operations of accepting at least one indication of a bioactive agent use by an individual, assigning an artificial sensory experience to monitor at least one desired effect of the bioactive agent on the individual, reporting at least one monitored effect, and/or predicting at least one effect of the bioactive agent when combined with the artificial sensory experience may be accomplished electronically, such as with a set of interconnected electrical components, an integrated circuit, and/or a computer processor.

Figure 34:
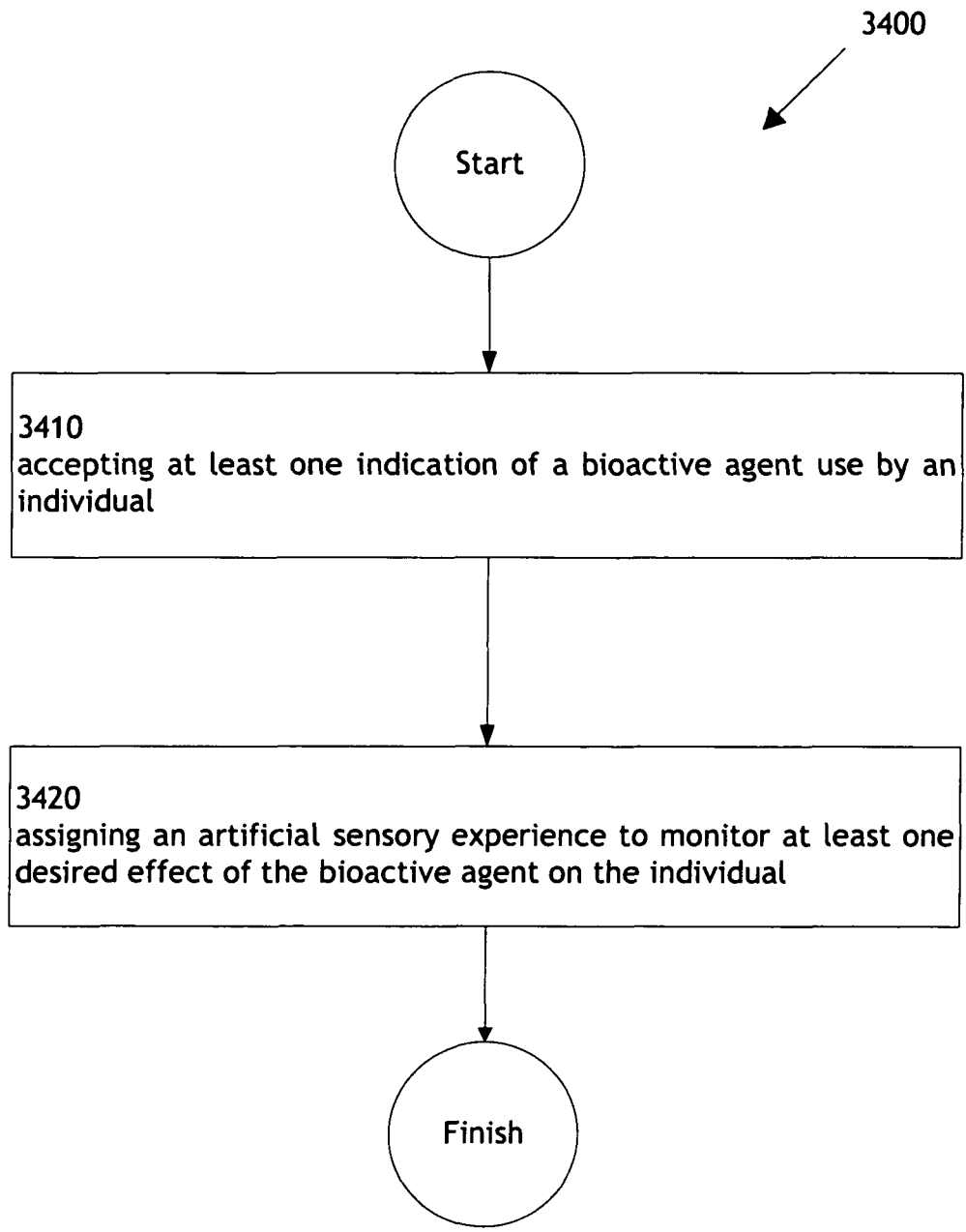
FIG. 34 illustrates an operational flow representing example operations related to monitoring at least one artificial sensory experience.

FIG. 34 illustrates an operational flow 3400 representing example operations related to accepting at least one indication of a bioactive agent use by an individual and assigning an artificial sensory experience to monitor at least one desired effect of the bioactive agent on the individual. In FIG. 34 and in following figures that include various examples of operational flows, discussion and explanation may be provided with respect to the above-described examples of FIGS. 32A through 33, and/or with respect to other examples and contexts. However, it should be understood that the operational flows may be executed in a number of other environments and contexts, and/or in modified versions of FIGS. 32A through 33. Also, although the various operational flows are presented in the sequence(s) illustrated, it should be understood that the various operations may be performed in other orders than those which are illustrated, or may be performed concurrently.

After a start operation, the operational flow 3400 moves to operation 3410. Operation 3410 depicts accepting at least one indication of a bioactive agent use by an individual. For example, as shown in FIGS. 32A through 33, acceptor module 102 may accept at least one indication of bioactive agent use by an individual 134. In one instance, acceptor module 102 may accept an indication of bioactive agent use including opioid use by a specific individual. A bioactive agent may include an agent that may have a biochemical and/or biological effect on any part of the human body. An indication of bioactive agent use may include a showing of bioactive agent use, such as the results of testing and/or input of at least one specific bioactive agent from a user 118, such as a health care provider 136. One example of a bioactive agent may include a pharmaceutical agent, such as codeine and/or acetaminophen. Another example of a bioactive agent may include a substance subject to abuse such as an illegal, controlled, and/or addictive substance, such as methamphetamine, nicotine, and/or alcohol. Additionally, an indication of a bioactive agent use may include a noticeable and/or detected effect associated with the bioactive agent, such as a side effect, an adverse drug reaction, a desired effect, and/or an unintended therapeutic effect. Accepting an indication of a bioactive agent use, for example, may include using a nanowire sensor for detecting the presence of a bioactive agent as discussed in Patolsky, F. et al., *Nanowire sensors for medicine and the life sciences*, NANOMEDICINE, 1(1):51-65 (2006), or using a wireless monitoring system as described in Xueliang, H. et al., *A Wireless Pharmaceutical Compliance Monitoring System Based on Magneto-Inductive Sensors*, SENSORS JOURNAL, IEEE, 7(12):1711-19 (2007), each of which is incorporated herein by reference. In some instances, acceptor module 102 may include a computer processor.

Then, operation 3420 depicts assigning an artificial sensory experience to monitor at least one desired effect of the bioactive agent on the individual. For example, as shown in FIGS. 32A through 33, assigner module 3334 may assign an artificial sensory experience to monitor at least one desired effect of the bioactive agent on the individual. Assigning an artificial sensory experience may include designating and/or specifying an artificial sensory experience tailored to the need of an individual 134 such as a patient in a doctor's care. Some examples of an artificial sensory experience may include a virtual experience, such as an online game or a social networking site, and/or a real-world sensory stimulus, such as a smell, a sound, and/or a sight. In one example, assigner module 3334 may assign a virtual world or a modification to a virtual world, such as a modification to an online game such as World of Warcraft, to monitor an effect of a specific medication administered, such as an antianxiety medication. In the same example, the medication effect may be monitored based on a pattern of activity, such as aggression by the player in the virtual world and/or individual 134 in eliminating trolls and/or advancement by the player's avatar. Assigning may include searching a database 122 and matching a bioactive agent with an appropriate artificial sensory experience taking into account characteristics of the individual 134, such as age, gender, susceptibility to adverse effects, and/or medication or therapeutic history. The assigning operation may entail merely the selection of a monitoring function to be carried out locally at the location of, for example, individual 134. In one embodiment, the selection of a monitoring function may be reported to a third party and/or to the individual 134. In other embodiments, the assigning operation may entail implementation of a monitoring function directly, either remotely or locally. For each artificial sensory experience, in addition to therapeutic functions, monitoring functions may be implemented, for example, as a modification to a virtual experience computer program and/or through a separate monitoring function. In some embodiments, one or more stimuli in an artificial sensory experience may elicit one or more reactions in an individual that may relate to an effect of a bioactive agent. For example, assignment of a Wii fitness virtual experience to provide physical therapy may serve to monitor the effectiveness of a coincident pain medication in the individual by measuring frequency of use, duration of use, range of motion, facial expression, or the like. Such monitoring capabilities may be added as a software module to the Wii itself, or the monitoring may be carried out by a different device. In some instances, assigner module 3334 may include a computer processor.

Figure 35:
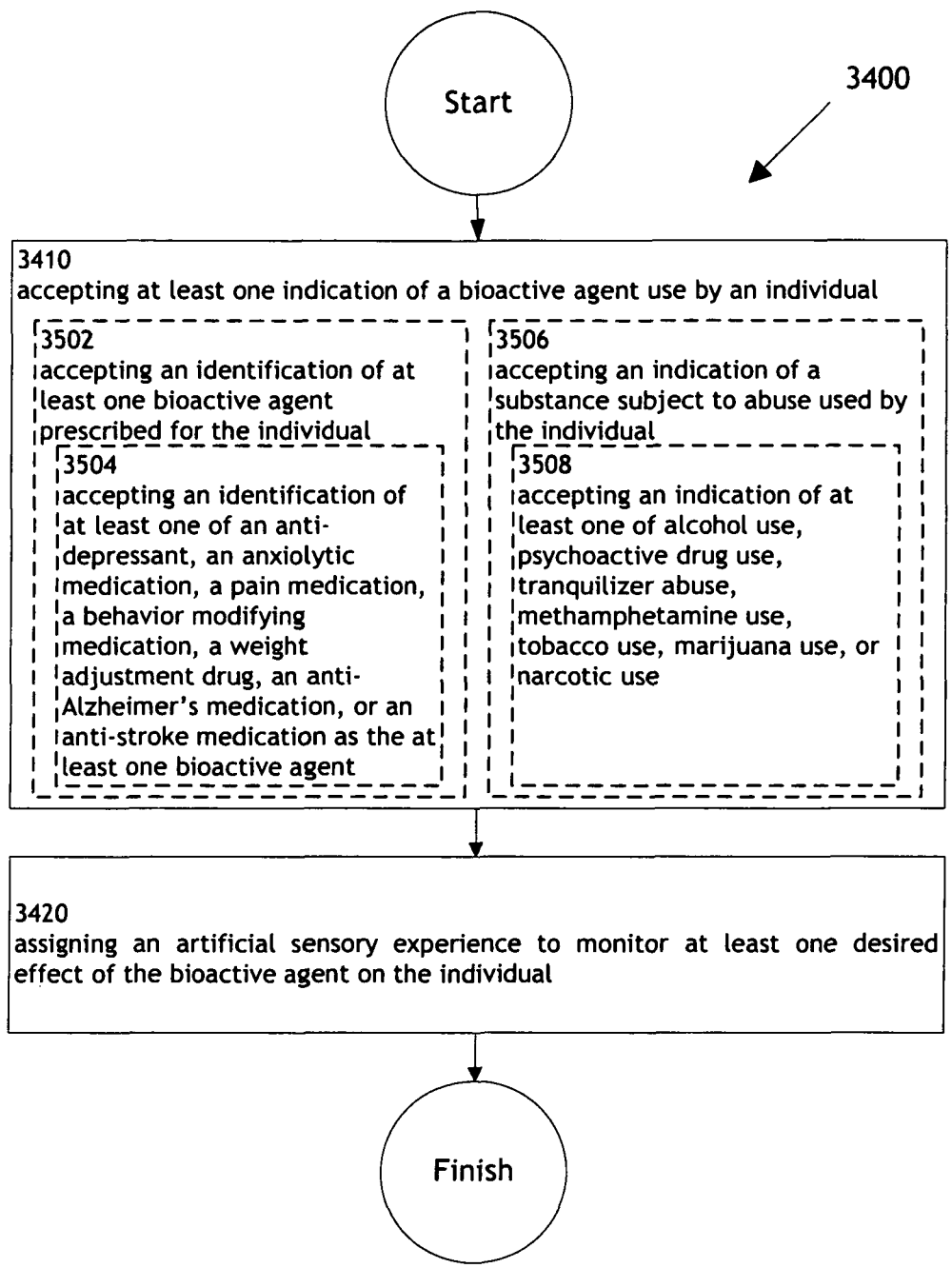
FIG. 35 illustrates an alternative embodiment of the operational flow of FIG. 34.

FIG. 35 illustrates alternative embodiments of the example operational flow 3400 of FIG. 34. FIG. 35 illustrates example embodiments where the operation 3410 may include at least one additional operation. Additional operations may include an operation 3502, an operation 3504, an operation 3506, and/or an operation 3508.

Operation 3502 illustrates accepting an identification of at least one bioactive agent prescribed for the individual. For example, as shown in FIGS. 32A through 33, bioactive agent identification acceptor module 3304 may accept an identification of a bioactive agent, such as codeine, prescribed for the individual 134 from user 118 and user interface 116. User 118 may, for example, include a medical professional. A prescribed medication may include a medicine that requires a physician's order for its use. Some examples of a prescribed medication may include Xanax®, Lipitor®, hydrocodone, and/or diazepam. In some instances, bioactive agent identification acceptor module 3304 may include a computer processor.

Further, operation 3504 illustrates accepting an identification of at least one of an anti-depressant, an anxiolytic medication, a pain medication, a behavior modifying medication, a weight adjustment drug, an anti-Alzheimer's medication, or an anti-stroke medication as the at least one bioactive agent. For example, as shown in FIGS. 32A through 33, bioactive agent identification acceptor module 3304 may accept an identification of at least one of an anti-depressant, an anxiolytic medication, a pain medication, a behavior modifying medication, a weight adjustment drug, an anti-Alzheimer's medication, or an anti-stroke medication as the at least one medication. In one example, bioactive agent identification acceptor module 3304 may accept an identification of a pain medication from user 118 and memory device 112. Accepting an identification of at least one bioactive agent may include using a drug sensor, such as those described above. An anti-depressant may include a psychiatric medication or other substance, such as a nutrient or herb, used for alleviating depression or dysthymia. Some examples of an anti-depressant may include fluoxetine and/or sertraline. An anxiolytic medication may include a substance used for the treatment of anxiety, such as a benzodiazepine and/or a barbiturate. A pain medication may include any substance and/or drug used to relieve pain. Some examples of an analgesic may include narcotics such as morphine or oxycodone, non-narcotics, an NSAID such as aspirin or naproxen or ibuprofen, and/or acetaminophen. A behavior modifying medication may include a substance used for preventing or reducing behavior associated with attention-deficit disorder (ADD) and/or attention-deficit hyperactivity disorder (ADHD). Additional behavior modifying medications may include medications used to treat attention deficiency, hyperactivity, attachment disorders, associative disorders, oppositional defiant disorder, aggression, and/or autistic spectrum disorders. Some examples of a behavior modifying medication may include methylphenidate, dextroamphetamine, and/or mixed amphetamine salts. A weight adjustment drug may include a drug and/or supplement used for decreasing appetite, increasing appetite and/or muscle mass, blocking fat absorption, and/or decreasing stomach volume. Some examples of a weight adjustment drug may include anabolic steroids, Megastrol (e.g., often used for patients with cancer that lose too much weight), DHEA, pregnenolone, orlistat, sibutramine, and/or melatonin. An anti-Alzheimer's medication may include medication used for the prevention and/or management of Alzheimer's disease. Some examples of an anti-Alzheimer's medication may include memantine, donepezil, galantamine, and/or rivastigmine. An anti-stroke medication may include medication used for preventing and/or treating stroke and/or symptoms of stroke. Some examples of anti-stroke medication may include aspirin, clopidogrel, and/or ticlopidine. In some instances, bioactive agent identification acceptor module 3304 may include a computer processor.

Operation 3506 illustrates accepting an indication of a substance subject to abuse used by the individual. For example, as shown in FIGS. 32A through 33, substance abuse indication acceptor module 3320 may accept an identification of a substance subject to abuse used by the individual. Some examples of a substance subject to abuse may include a controlled substance, such as substances included in the Controlled Substances Act (e.g., cannabis, heroin, cocaine, and/or hydrocodone), and/or other substances subject to abuse, such as alcohol, tobacco, glue, cough medicine, and/or solvents. In one instance, substance abuse indication acceptor module 3320 may accept from user 118 and network storage 110 an identification of a controlled substance including cocaine used by an anonymous individual. A controlled substance may include a psychoactive drug or performance enhancing drug used for a non-therapeutic or non-medical effect. Some other examples of a controlled substance may include amphetamines, barbiturates, benzodiazepines, methaqualone, and/or opium alkaloids. In some instances, substance abuse indication acceptor module 3320 may include a computer processor.

Further, operation 3508 illustrates accepting an indication of at least one of alcohol use, psychoactive drug use, tranquilizer abuse, methamphetamine use, tobacco use, marijuana use, or narcotic use. For example, as shown in FIGS. 1 through 2, substance abuse indication acceptor module 3320 may accept an indication of at least one of alcohol use, psychoactive drug use, tranquilizer use, methamphetamine use, tobacco use, marijuana use, or narcotic use. In one embodiment, substance abuse indication acceptor module 3320 may accept an identification of alcohol use and methamphetamine use from health care provider 136 and user interface 116. In another embodiment, substance abuse indication acceptor module 3320 may accept an indication of alcohol use and/or methamphetamine use from a transdermal alcohol sensing instrument. Accepting an indication of alcohol use may include, for example, using a transdermal alcohol sensing instrument, further described in Bellehumeur, U.S. Pat. No. 6,886,653, which is incorporated herein by reference. Other methods of alcohol use detection may also be used, such as breathalyzer analysis, infrared spectroscopy, ethyl glucuronide analysis, speech analysis, body coordination analysis, or the like. Alcohol use may include alcohol abuse, alcohol dependence, alcoholism, and/or recreational alcohol consumption. Tobacco use may include the use of and/or the addiction to tobacco products, such as cigarette use and/or chewing tobacco use. Psychoactive drug use, tranquilizer use, methamphetamine use, marijuana use, and/or narcotic use may include recreational drug and/or substance use and/or drug abuse. In some instances, substance abuse indication acceptor module 3320 may include a computer processor.

Figure 36:
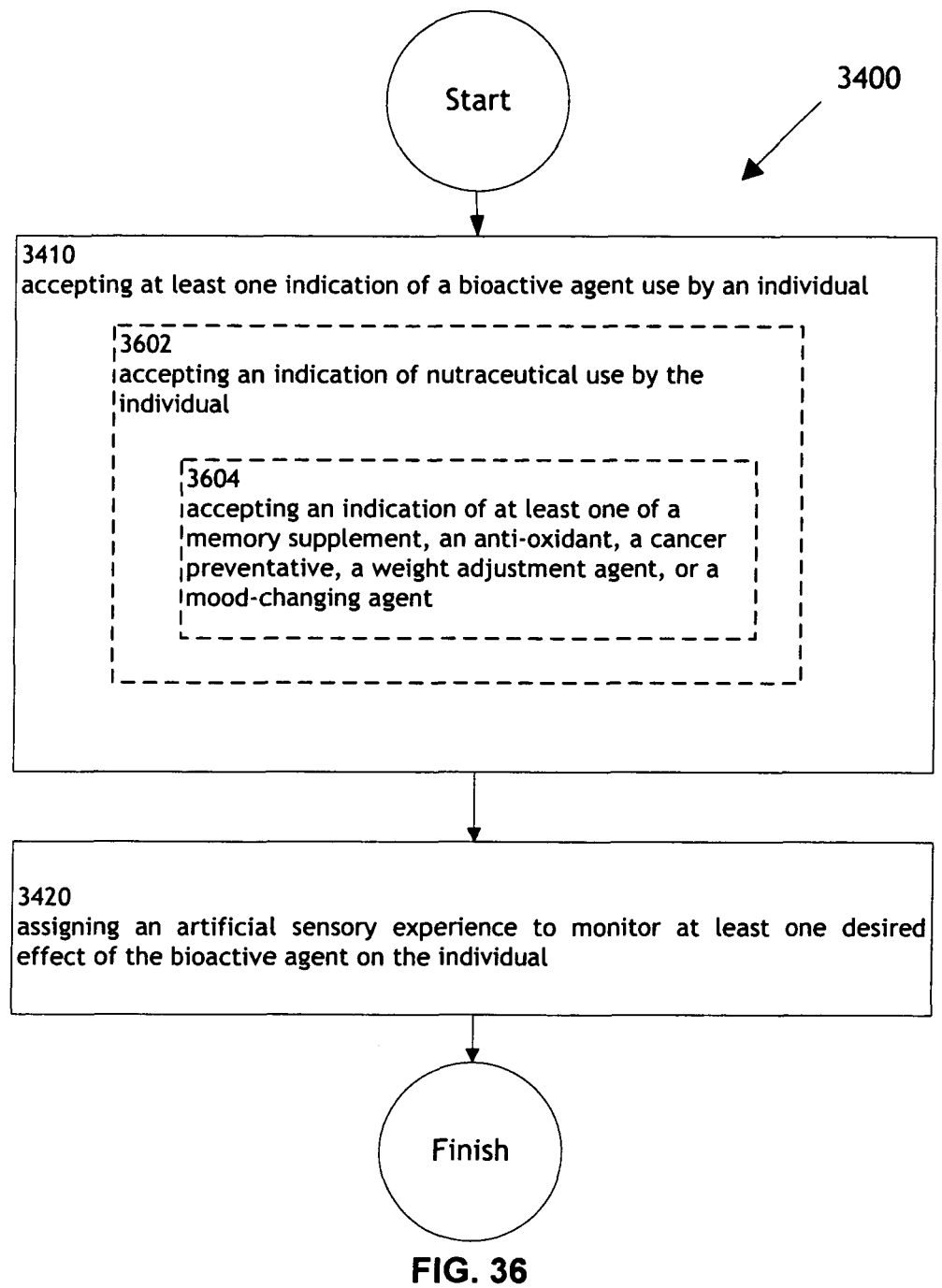
FIG. 36 illustrates an alternative embodiment of the operational flow of FIG. 34.

FIG. 36 illustrates alternative embodiments of the example operational flow 3400 of FIG. 34. FIG. 36 illustrates example embodiments where the operation 3410 may include at least one additional operation. Additional operations may include an operation 3602, and/or an operation 3604.

Operation 3602 illustrates accepting an indication of nutraceutical use by the individual. For example, as shown in FIGS. 32A through 33, nutraceutical identification acceptor module 3324 may accept an identification of a nutraceutical used by the individual 134. In one instance, nutraceutical identification acceptor module 3324 may accept an identification of a soy-based isoflavonoid nutraceutical used by the individual. A nutraceutical may refer to a food extract having and/or claimed to have a medicinal effect on human health. Some examples of a nutraceutical may include flavonoid antioxidants, alpha-linolenic acid from flax seeds, beta-carotene from marigold petals, anthocyanins from berries, ginseng, and/or garlic oil. In some instances, nutraceutical identification acceptor module 3324 may include a computer processor and/or other sensor instrumentation, such as the nanowire discussed above.

Further, operation 3604 illustrates accepting an indication of at least one of a memory supplement, an anti-oxidant, a cancer preventative, a weight adjustment agent, or a mood-changing agent. For example, as shown in FIGS. 32A through 33, nutraceutical identification acceptor module 3324 may accept an identification of at least one of a memory supplement, an anti-oxidant, a cancer preventative, a weight adjustment agent, or a mood-changing agent from health care provider 136 and user interface 116. In one instance, nutraceutical identification acceptor module 3324 may accept an identification of an herbal memory supplement including *ginkgo biloba*. A memory supplement may include a substance obtained from an animal and/or a plant source for maintaining and/or improving memory, such as *salvia lavandulaefolia* and/or *ginkgo biloba*. An anti-oxidant may include a substance capable of slowing or preventing the oxidation of other molecules and is purported to neutralize hazardous free-radicals within the body. Some examples of an antioxidant may include ascorbic acid, glutathione, melatonin, and/or tocopherol. A cancer preventative may include a drug, a treatment, and/or substance utilized for preventing the occurrence of and/or the progression of cancer. Some examples of a cancer preventative may include acupuncture, all-trans retinoic acid, mistletoe derivatives, and/or lycopene. A weight adjustment agent may include a drug and/or supplement used for decreasing appetite, increasing appetite, increasing muscle mass, blocking fat absorption, and/or decreasing stomach volume. Some examples of a weight adjustment agent may include DHEA, anabolic steroids, pregnenolone, orlistat, sibutramine, and/or melatonin. A mood-changing agent may include a psychiatric medication used to treat mood disorders characterized by intense and sustained mood shifts. Some examples of a mood-changing agent may include lithium carbonate and/or lamotrigine. In some instances, nutraceutical identification acceptor module 3324 may include a computer processor and/or other sensor instrumentation, such as the nanowire discussed above.

Figure 37:
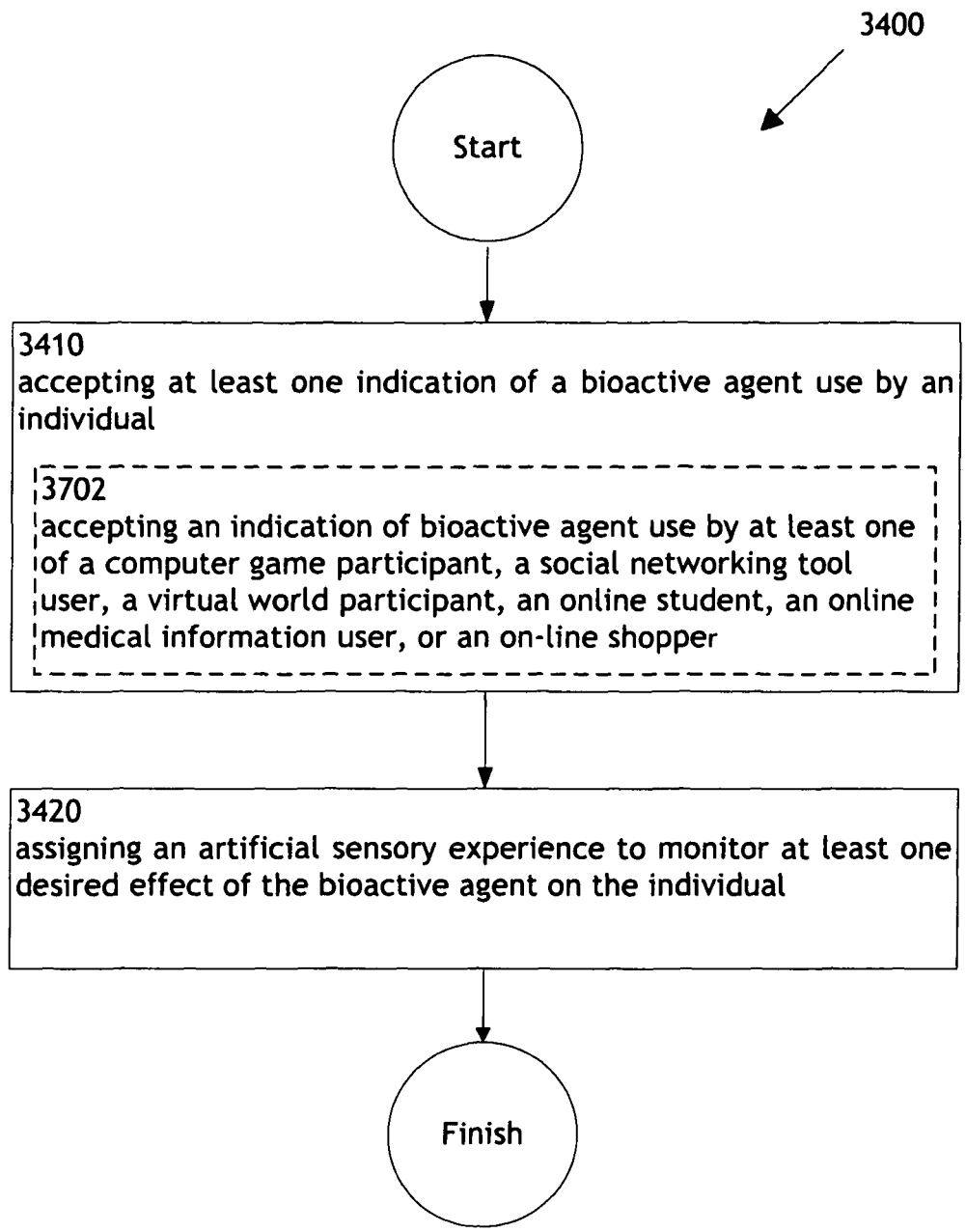
FIG. 37 illustrates an alternative embodiment of the operational flow of FIG. 34.

FIG. 37 illustrates alternative embodiments of the example operational flow 3400 of FIG. 34. FIG. 37 illustrates example embodiments where the operation 3410 may include at least one additional operation. Additional operations may include an operation 3702.

Operation 3702 illustrates accepting an indication of bioactive agent use by at least one of a computer game participant, a social networking tool user, a virtual world participant, an online student, an online medical information user, or an on-line shopper. For example, as shown in FIGS. 32A through 33, bioactive agent identification acceptor module 3304 may accept at (east one indication of bioactive agent use by at least one of a computer game participant, a social networking tool user, a virtual world participant, an online student, an online medical information user, or an on-line shopper.

In one embodiment, bioactive agent identification acceptor module 3304 may accept an indication of bioactive agent use by a virtual world participant. In another instance, bioactive agent identification acceptor module 3304 may accept an indication of bioactive agent use by an online student enrolled in an online college course through a community college. In another instance, bioactive agent identification acceptor module 3304 may accept an indication of bioactive agent use by an online medical information user using a secure connection. Online communications may include private and/or confidential communications using a secure method, such as a secure web browser and/or a secure internet connection, for ensuring the privacy of a user and/or participant. A computer game may include an online game, an online educational experience, a networked game, and/or a single-player game. Some examples of computer games may include World of Warcraft (WoW), solitaire, and/or RuneScape.

A social networking tool may include a website for observing and/or interacting with one or more personal and/or professional relationships between individuals. Some examples of a social networking website may include MySpace, GeoCities, Facebook, and/or LinkedIn. Some other examples of a social networking tool may include picture chat, a gaming device, and/or instant messaging (IM). Additionally, a social networking tool user may include a social networking website user and/or users of the social networking tools mentioned herein. A virtual world may include a computer-based simulated environment intended for its users to inhabit and interact via avatars, such as Second Life. An online student may be enrolled in and/or learn from an online educational experience such as a tutorial, a lesson, and/or an online class. Some examples of an online educational experience may include a HTML tutorial, an online piano lesson, and/or an online degree program from the University of Phoenix. Online medical information may include a website and/or a database, such as http://www.ncbi.nlm.gov/pubmed/, MEDLINE, MEDLARS, and/or http://www.webmd.com. An online shopper may shop at an internet marketplace, such as eBay.com, Amazon.com, and/or Froogle.com. In some instances, bioactive agent identification acceptor module 3304 may include a computer processor and/or other sensor instrumentation, such as the nanowire discussed above.

Figure 38:
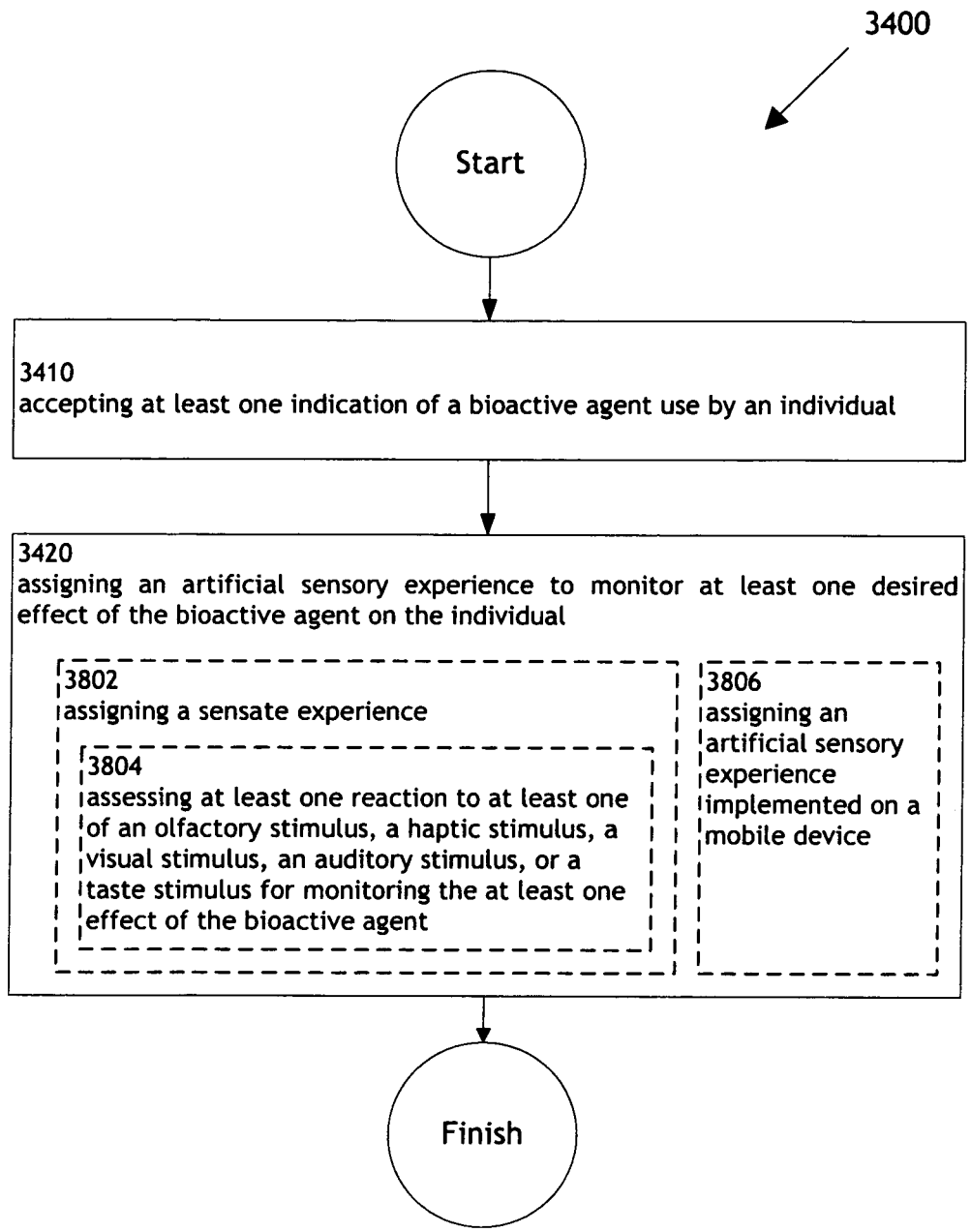
FIG. 38 illustrates an alternative embodiment of the operational flow of FIG. 34.

FIG. 38 illustrates alternative embodiments of the example operational flow 3400 of FIG. 34. FIG. 38 illustrates example embodiments where the operation 3420 may include at least one additional operation. Additional operations may include an operation 3802, an operation 3804, and/or an operation 3806.

Operation 3802 illustrates assigning a sensate experience. For example, as shown in FIGS. 32A through 33, sensate experience assigner module 3336 may assign a sensate experience as at least a portion of an artificial sensory experience, such as an aroma. A sensate experience may include a thing perceived by the senses, such as an aroma, a sound, a feel, a taste, and/or a sight. In some instances, sensate experience assigner module 3336 may include a computer processor. Further, operation 3804 illustrates assessing at least one reaction to at least one of an olfactory stimulus, a haptic stimulus, a visual stimulus, an auditory stimulus, or a taste stimulus for monitoring the at least one effect of the bioactive agent. For example, as shown in FIGS. 32A through 33, stimulus assessor module 3338 may assess at least one reaction to an auditory stimulus, such as music with an upbeat tempo, to monitor an effect of the bioactive agent, such as an antidepressant. In this example, an assessment of an individual's reaction to the auditory stimulus, such as attention, alertness, and/or receptivity to the upbeat tempo music, may indicate a decrease in depression and may serve to monitor the antidepressant. Further discussion regarding an olfactory stimulus may be found in Shaw, D. et al., *Anxiolytic effects of lavender oil inhalation on open-field behaviour in rats*, PHYTOMEDICINE, 14(9):613-20 (2007); Marlier, L. et al., *Olfactory Stimulation Precents Apnea in Premature Newborns*, PEDIATRICS, 115(1):83-88 (2005); and Murayama et al., U.S. Pat. No. 6,282,458; each incorporated by reference. In one embodiment, stimulus assessor module 3338 may assess a reaction to a haptic stimulus, such as touching and detecting a rough friction-causing surface, in an individual with a sensory deficit, such that detection of and/or reaction to the rough friction-causing surface indicates improvement of the sensory deficit. Detection of a rough surface combined with administration of a bioactive agent, such as a growth factor protein used for stimulating nerve regeneration, may serve to monitor an effect and/or efficacy of the bioactive agent in reducing and/or eliminating the sensory deficit. Further discussion regarding human perception of friction and growth factor proteins may be found respectively in Lawrence, D. A. et al., Human Perception of Friction in Haptic Interfaces, *Human Perceptual Thresholds of Friction in Haptic Interfaces*, PROC. ASME DYNAMIC SYSTEMS AND CONTROL DIVISION, DSC-Vol. 64, pp. 287-294, ASME INT. MECH. ENGR. CONG. & EXPO., Anaheim, Calif., November 1998; and Washington University In St. Louis (2002, Jul. 26), *New Horizons Of Nerve Repair: Biomedical Engineer Trips Up Proteins In Nerve Regeneration System*, SCIENCEDAILY. Retrieved Jul. 2, 2008, from http://www.sciencedaily.com/releases/2002/07/020725082253.htm.; both incorporated herein by reference. Further discussion regarding a haptic stimulus and/or an auditory stimulus may be found in Cañadas-Quesada, F. J. et al., *Improvement of Perceived Stiffness Using Auditory Stimuli in Haptic Virtual Reality*, IEEE MELECON, May 16-19, Benalmádena (Málaga) Spain; and Rizzo, A. et al., *Virtual Therapeutic Environments with Haptics: An Interdisciplinary Approach for Developing Post-Stroke Rehabilitation Systems*, Proceedings of The 2005 International Conference on Computers for People with Special Needs, 70-76, CPSN 2005, Las Vegas, Nev., Jun. 20-23, 2005, both incorporated herein by reference. Assessing stimuli and/or a reaction to stimuli, such as an olfactory stimulus, a haptic stimulus, a visual stimulus, an auditory stimulus, or a taste stimulus, may elicit reactions in the individual 134 that indicate at least one effect of the bioactive agent and may serve to monitor the at least one effect of the bioactive agent. In some instances, stimulus assessor module 3338 may include a computer processor.

Operation 3806 illustrates assigning an artificial sensory experience implemented on a mobile device. For example, as shown in FIGS. 1 through 2, assigner module 3334 may assign a bright background color theme in a virtual world implemented on a mobile device, such as a web browser on a laptop computer having wireless capability and a battery. In this example, assigning a bright background color theme on a mobile device combined with a bioactive agent, for example an antidepressant, may elicit a reaction by individual 134, such as increased activity and less depressive behavior (e.g., more message posting and less reclusive behavior while interacting with others on a social networking website, such as MySpace.com) indicating an effect of the bioactive agent and serving to monitor an effect of the bioactive agent. Some examples of a mobile device may include a laptop or notebook computer, a personal digital assistant (PDA), an ipod, a smartphone, an Enterprise digital assistant (EDA), and/or a pager. One example of a mobile device for use in a virtual environment may include multiple access terminals and a removable memory card, further discussed in Viktorsson et al., U.S. Pat. No. 6,397,080, which is incorporated herein by reference. In some instances, assigner module 3334 may include a computer processor.

Figure 39:
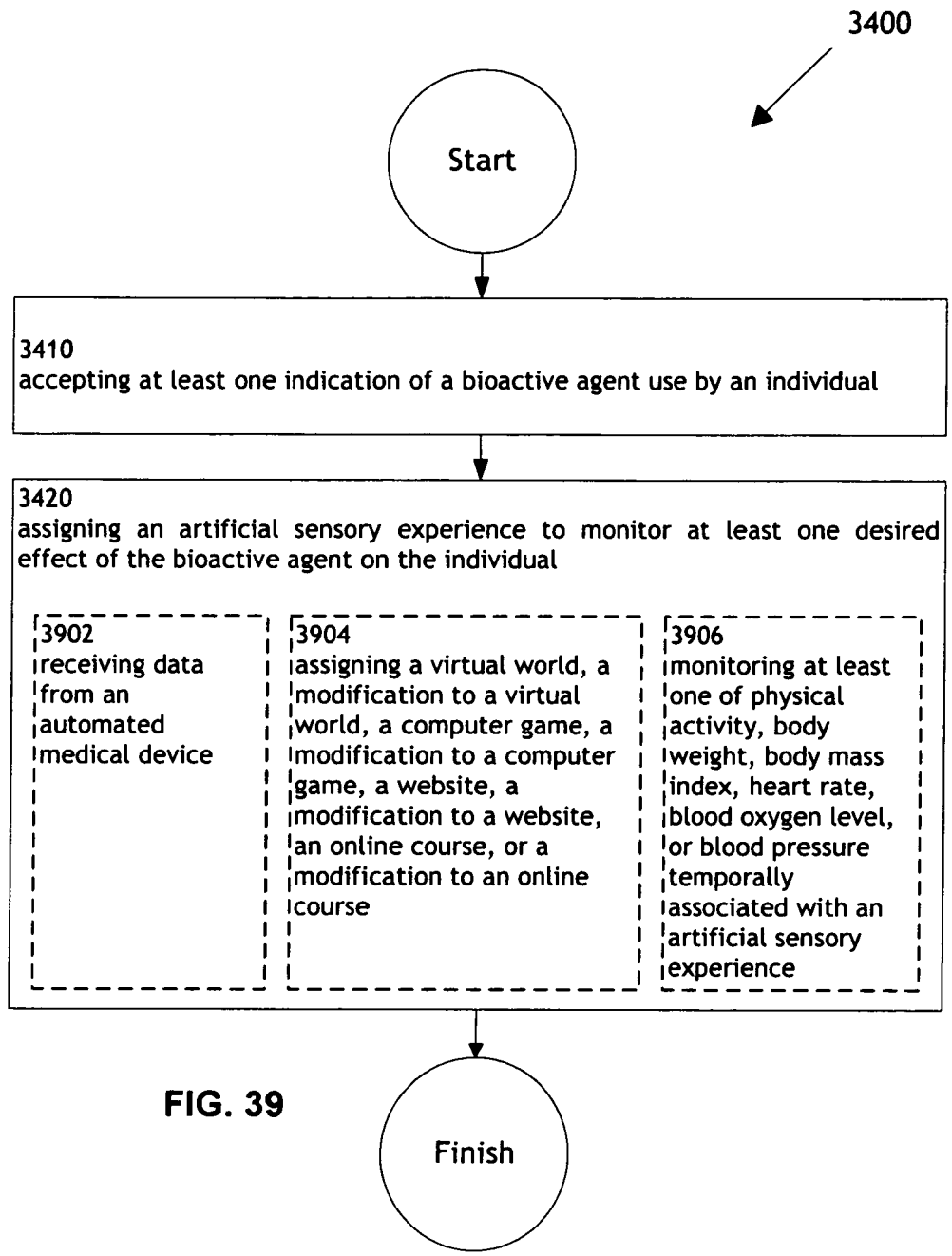
FIG. 39 illustrates an alternative embodiment of the operational flow of FIG. 34.

FIG. 39 illustrates alternative embodiments of the example operational flow 3400 of FIG. 34. FIG. 39 illustrates example embodiments where the operation 3420 may include at least one additional operation. Additional operations may include an operation 3902, an operation 3904, and/or an operation 3906.

Operation 3902 illustrates receiving data from an automated medical device. For example, as shown in FIGS. 32A through 33, automated medical device receiver module 3340 may receive data from an automated medical device, such as an electrocardiograph. An automated medical device may include a medical monitor, or a device that senses a patient's vital signs and communicates the results to a monitor and/or a user 118. Some examples of an automated medical device may include an electrocardiograph, such as a Holter monitor, medical imaging machines, such as an ultrasound machine and/or a magnetic resonance imaging machine, analysis instrumentation, such as a blood glucose meter, and/or a pulse oximeter. Other examples of an automated medical device may include a pedometer, a heart rate monitor, a blood pressure monitor, a body-fat analyzer, and/or a neurophysiological monitor. Additionally, a multi-parameter automated medical device may simultaneously measure and/or track multiple vital signs. One example of an automated device may include a tele-medicine application, further described in Jeanpierre, L. et al., *Automated medical diagnosis with fuzzy stochastic models: monitoring chronic diseases*, ACTA BIOTHERETICA, 52(4):291-311 (2004), which is incorporated herein by reference. In some instances, automated medical device receiver module 3340 may include a computer processor and/or a monitor coupled to a computer processor.

Operation 3904 illustrates assigning a virtual world, a modification to a virtual world, a computer game, a modification to a computer game, a website, a modification to a website, an online course, or a modification to an online course. For example, as shown in FIGS. 32A through 33, assigner module 3334 may assign a virtual world. A virtual world may include a computer-based simulated environment intended for its users to inhabit and interact via avatars. Some examples of a virtual world may include a massively multiplayer online role-playing game (MMORPG), such as World of Warcraft, a snow world, and/or simple virtual geocaching, such as on Google Earth. In one embodiment, assigner module 3334 may assign World of Warcraft as a virtual world. A computer game may include a video game and/or other software-based game executed on a personal computer, an arcade machine, and/or other video game console. Some examples of a computer game may include Super Mario 64, World of Warcraft, and/or Guild Wars. A website may include a collection of webpages, images, videos, and/or other digital assets hosted on at least one webserver and may be accessible via the Internet. Some examples of a website may include yahoo.com and/or MySpace.com. In one embodiment, assigner module 3334 may assign the use of a website including Facebook.com. An online course may include an online educational experience such as a tutorial, a lesson, and/or an online class. Some examples of an online course may include a HTML tutorial, an online piano lesson, and/or an online degree program from the University of Phoenix. In another embodiment, assigner module 3334 may assign an online social skills tutorial to help an individual 134 overcome a social phobia where the tutorial is coupled with a bioactive agent, such as an antianxiety medication. Examples of a modification to a virtual world, a computer game, a website, and/or an online course may include restricting access, granting access, altering a visual object, altering a color scheme, modifying text, and/or altering a sound, music, a voice, and/or ambient noise. In some instances, assigner module 3334 may include a computer processor configured to match an artificial sensory experience with a bioactive agent based on the individual.

Operation 3906 illustrates monitoring at least one of physical activity, body weight, body mass index, heart rate, blood oxygen level, or blood pressure temporally associated with an artificial sensory experience. For example, as shown in FIGS. 32A through 33, monitorer module 3342 may monitor an individual's heart rate. Physical activity may include any form of exercise, movement, and/or bodily activity. Some examples of a physical activity may include exercise, body movement, walking, running, and/or muscle stretching. Monitoring physical activity may include using a pedometer, an accelerometer, for example, available from New-Lifestyles, Inc., Lee's Summit, Mo., and/or other devices, such as actometers, further discussed in Zhang et al., *Measurement of Human Daily Physical Activity*, OBESITY RESEARCH, 11 (1): 33-40 (2003), which is incorporated herein by reference. Monitoring a body weight and/or a body mass index may include using a scale and/or a computing device. In one embodiment, monitorer module 3342 may monitor a body mass index of an individual experiencing a Wii Fitness game while being administered a weight loss medication by using a scale 3220 coupled with a computer processor. In the same embodiment, scale 3220 and computer processor may constantly monitor the body mass index of the individual 134. Monitoring a heart rate may include measuring work done by the heart, such as measuring beats per unit time and/or a pulse. Monitoring a blood oxygen level may include utilizing a pulse oximeter and/or measuring oxygen saturation directly through a blood sample. Monitoring blood pressure may include utilizing a sphygmomanometer, which may be coupled to a computer processor or other monitoring device. Monitoring physical activity, a heart rate, a blood oxygen level, and/or blood pressure when an individual is experiencing an artificial sensory experience may serve to determine the efficacy of a bioactive agent. For example, when an antianxiety medication is administered to an individual prior to and/or during an artificial sensory experience, such as a spider world designed to overcome a spider phobia, monitorer module 3342 may monitor a heart rate in order to determine whether the antianxiety medication is effective. In the above example, the individual's heart rate may decrease due to a decrease in anxiety as the antianxiety medication takes effect indicating drug efficacy. Additionally, monitorer module 3342 may monitor before, during, and/or after experiencing an artificial sensory experience. In some instances, monitorer module 3342 may include a computer processor and/or medical instrumentation.

Figure 40:
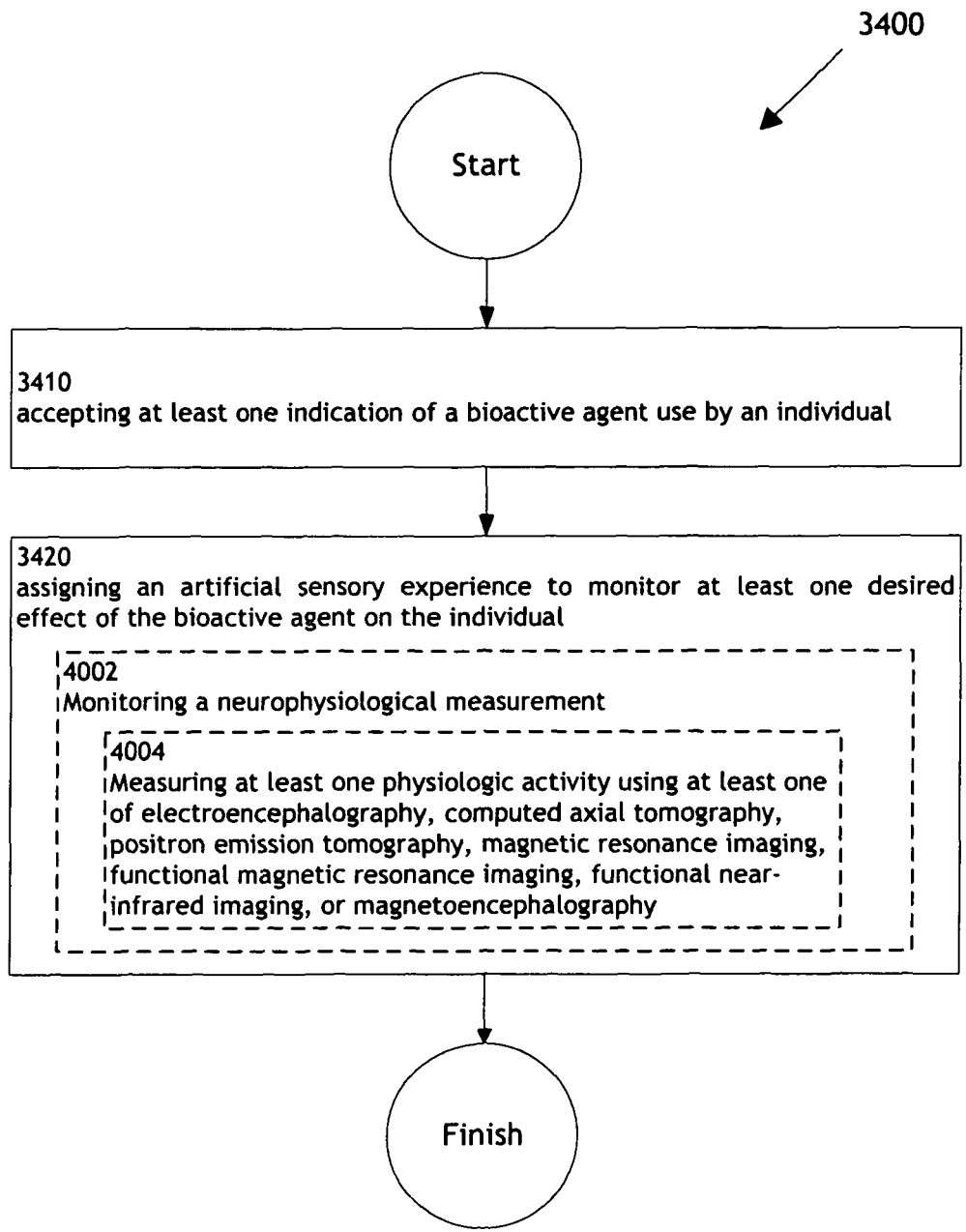
FIG. 40 illustrates an alternative embodiment of the operational flow of FIG. 34.

FIG. 40 illustrates alternative embodiments of the example operational flow 3400 of FIG. 34. FIG. 40 illustrates example embodiments where the operation 3420 may include at least one additional operation. Additional operations may include an operation 4002, and/or an operation 4004.

Operation 4002 illustrates monitoring a neurophysiological measurement. For example, as shown in FIGS. 32A through 33, neurophysiological measurement monitorer module 3344 may monitor a neurophysiological measurement, such as a measurement of the activation signal of muscles (electromyography) and/or the measurement of transcranial magnetic stimulation. A neurophysiological measurement may include a measurement of the brain, nervous system, and/or neuromonitoring. In some instances, neurophysiological measurement monitorer module 3344 may include a computer processor and/or a medical device, such as device configured to measure somatosensory evoked potentials (SSEPs), auditory brainstem response (ABR), and/or scalp sensors used in electroencephalography (EEG). Operation 4004 illustrates measuring at least one physiologic activity using at least one of electroencephalography, computed axial tomography, positron emission tomography, magnetic resonance imaging, functional magnetic resonance imaging, functional near-infrared imaging, or magnetoencephalography. For example, as shown in FIGS. 32A through 33, physiologic activity measurer module 3346 may measure at least one physiologic activity using at least one of electroencephalography, computed axial tomography, positron emission tomography, magnetic resonance imaging, functional magnetic resonance imaging, functional near-infrared imaging, or magnetoencephalography. In some instances, physiologic activity measurer module 3346 may include a computer processor, and/or a medical device, such as an apparatus configured to perform a computed axial tomography scan.

Electroencephalography may include measuring the electrical activity of the brain by recording from electrodes placed on the scalp or, in special cases, subdurally, or in the cerebral cortex. The resulting traces are known as an electroencephalogram (EEG) and represent a summation of post-synaptic potentials from a large number of neurons. EEG is most sensitive to a particular set of post-synaptic potentials: those which are generated in superficial layers of the cortex, on the crests of gyri directly abutting the skull and radial to the skull. Dendrites that are deeper in the cortex, inside sulci, are in midline or deep structures (such as the cingulate gyrus or hippocampus) or that produce currents that are tangential to the skull make a smaller contribution to the EEG signal.

One application of EEG is event-related potential (ERP) analysis. An ERP is any measured brain response that is directly the result of a thought or perception. ERPs can be reliably measured using electroencephalography (EEG), a procedure that measures electrical activity of the brain, typically through the skull and scalp. As the EEG reflects thousands of simultaneously ongoing brain processes, the brain response to a certain stimulus or event of interest is usually not visible in the EEG. One of the most robust features of the ERP response is a response to unpredictable stimuli. This response is known as the P300 (P3) and manifests as a positive deflection in voltage approximately 300 milliseconds after the stimulus is presented.

A two-channel wireless brain wave monitoring system powered by a thermo-electric generator has been developed by IMEC (Interuniversity Microelectronics Centre, Leuven, Belgium). This device uses the body heat dissipated naturally from the forehead as a means to generate its electrical power. The wearable EEG system operates autonomously with no need to change or recharge batteries. The EEG monitor prototype is wearable and integrated into a headband where it consumes 0.8 milliwatts. A digital signal processing block encodes extracted EEG data, which is sent to a PC via a 2.4-GHz wireless radio link. The thermoelectric generator is mounted on the forehead and converts the heat flow between the skin and air into electrical power. The generator is composed of 10 thermoelectric units interconnected in a flexible way. At room temperature, the generated power is about 2 to 2.5-mW or 0.03-mW per square centimeter, which is the theoretical limit of power generation from the human skin. Such a device is proposed to associate emotion with EEG signals. See Clarke, "IMEC has a brain wave: feed EEG emotion back into games," EE Times online, http://www.eetimes.eu/design/202801063 (Nov. 1, 2007).

Computed axial tomography may include medical imaging employing tomography and digital geometry processing for generating a three-dimensional image of the inside of an object from a large series of two-dimensional X-ray images taken around a single axis of rotation. Positron emission tomography may include a nuclear medicine imaging technique, which produces a three-dimensional image and/or map of at least one functional process in the body. The system detects pairs of gamma rays emitted indirectly by a positron-emitting radionuclide (a tracer), which is introduced into the body on a biologically active molecule. Images of tracer concentration in 3-dimensional space within the body may then be reconstructed by computer analysis. Magnetic resonance imaging may include a medical imaging technique using a magnetic field to align the nuclear magnetization of hydrogen atoms in water in the body, resulting in an image of the body. Functional magnetic resonance imaging may include and imaging method for measuring haemodynamic response related to neural activity in the brain or spinal cord. Functional near-infrared imaging (fNIR) may include a spectroscopic neuro-imaging method for measuring the level of neuronal activity in the brain. Functional near-infrared imaging (fNIR) is based on neuro-vascular coupling, or the relationship between metabolic activity and oxygen level (oxygenated hemoglobin) in feeding blood vessels.

Magnetoencephalography includes measuring the magnetic fields produced by electrical activity in the brain using magnetometers such as superconducting quantum interference devices (SQUIDs) or other devices. Smaller magnetometers are in development, including a mini-magnetometer that uses a single milliwatt infrared laser to excite rubidium in the context of an applied perpendicular magnetic field. The amount of laser light absorbed by the rubidium atoms varies predictably with the magnetic field, providing a reference scale for measuring the field. The stronger the magnetic field, the more light is absorbed. Such a system is currently sensitive to the 70 fT range, and is expected to increase in sensitivity to the 10 fT range. See Physorg.com, "New mini-sensor may have biomedical and security applications," Nov. 1, 2007, http://www.physorg.com/news113151078.html, which is incorporated herein by reference.

Figure 41:
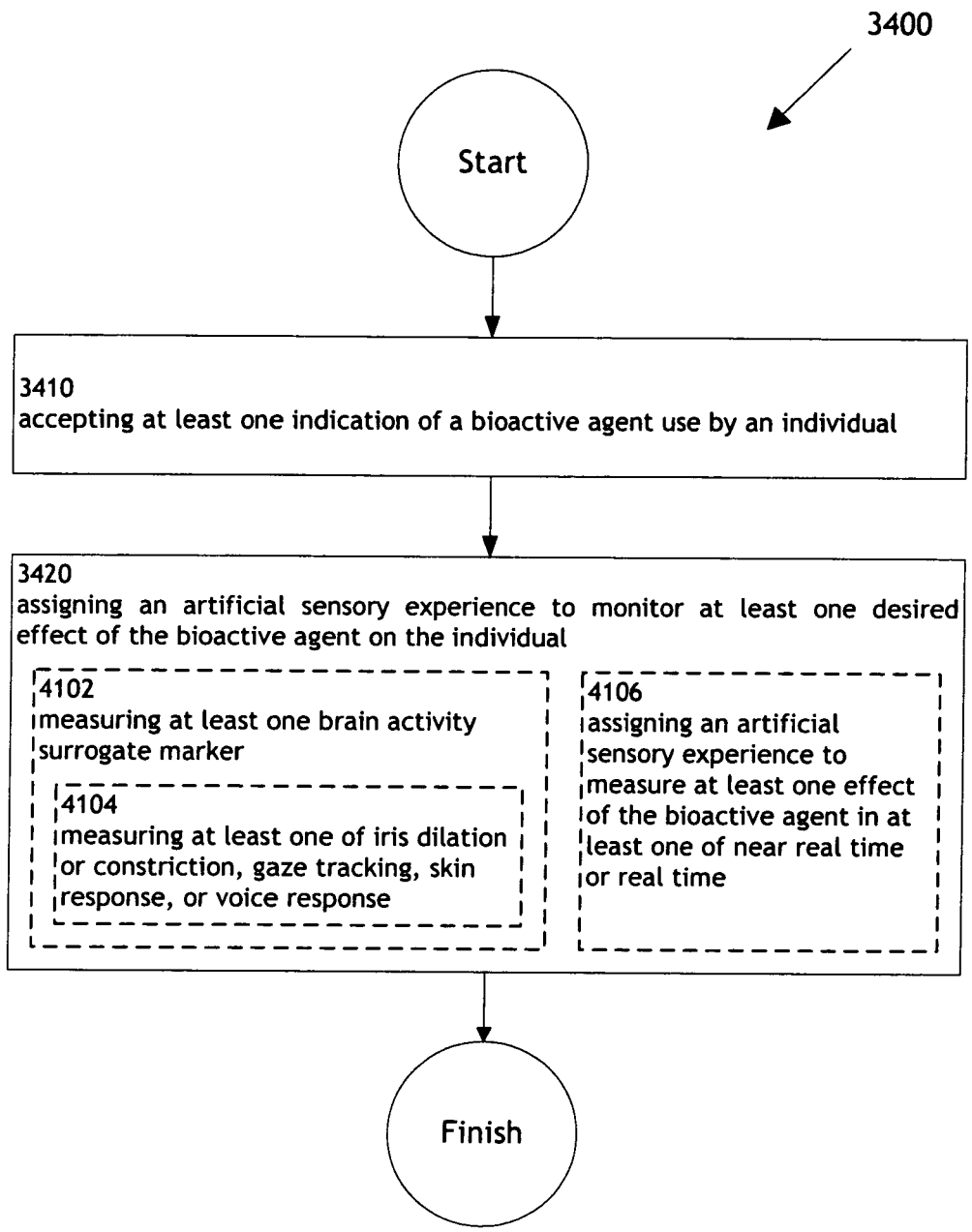
FIG. 41 illustrates an alternative embodiment of the operational flow of FIG. 34.

FIG. 41 illustrates alternative embodiments of the example operational flow 3400 of FIG. 34. FIG. 41 illustrates example embodiments where the operation 3420 may include at least one additional operation. Additional operations may include an operation 4102, an operation 4104, and/or an operation 4106.

Operation 4102 illustrates measuring at least one brain activity surrogate marker. For example, as shown in FIGS. 32A through 33, brain activity surrogate marker measurer module 3348 may measure a brain activity surrogate marker. In some instances, brain activity surrogate marker measurer module 3348 may include a computer processor and/or medical instrumentality configured to measure a surrogate marker, such as a stethoscope, a face recognition system, and/or a sphygmomanometer. Brain activity surrogate markers may include indicators of attention, approval, disapproval, recognition, cognition, memory, trust, or the like in response to a stimulus, other than measurement of brain activity associated with the stimulus. Some examples of surrogate markers may include a skin response to a stimulus; a face pattern indicative of approval, disapproval, or emotional state; eye movements or pupil movements indicating visual attention to an object; voice stress patterns indicative of a mental state, or the like. Surrogate markers may be used in conjunction with brain activity measurements for higher confidence in a predictive or interpretational outcome. For example, brain activation of the caudate nucleus in combination with calm voice patterns may increase confidence in a predictor of trust between a subject and a stimulus. Additional discussion regarding surrogate markers may be found in Cohn, J. N., *Introduction to Surrogate Markers*, CIRCULATION 109: IV20-21, American Heart Association, (2004), which is incorporated herein by reference.

For example, emotion links to cognition, motivation, memory, consciousness, and learning and developmental systems. Affective communication depends on complex, rule-based systems with multiple channels and redundancy built into the exchange system, in order to compensate if one channel fails. Channels can include all five senses: for example, increased heart-rate or sweating may show tension or agitation and can be heard, seen, touched, smelt or tasted. Emotional exchanges may be visible displays of body tension or movement, gestures, posture, facial expressions or use of personal space; or audible displays such as tone of voice, choice of pitch contour, choice of words, speech rate, etc. Humans also use touch, smell, adornment, fashion, architecture, mass media, and consumer products to communicate our emotional state. Universals of emotion that cross cultural boundaries have been identified, and cultural differences have also been identified. For example 'love' is generally categorized as a positive emotion in Western societies, but in certain Eastern cultures there is also a concept for 'sad love.' Accordingly, universal emotional triggers may be used to transcend cultural barriers.

When communicating with computers, people often treat new media as if they were dealing with real people. They often follow complex social rules for interaction and modify their communication to suit their perceived conversation partner. Much research has focused on the use of facial actions and ways of coding them. Speech recognition systems have also attracted attention as they grow in capability and reliability, and can recognize both verbal messages conveyed by spoken words, and non verbal messages, such as those conveyed by pitch contours.

System responses and means of expressing emotions also vary. Innovative prototypes are emerging designed to respond indirectly, so the user is relatively unaware of the response: for example by adaptation of material, such as changing pace or simplifying or expanding content. Other systems use text, voice technology, visual agents, or avatars to communicate. See Axelrod et al., "Smoke and Mirrors: Gathering User Requirements for Emerging Affective Systems," 26th Int. Conf. Information Technology Interfaces/TI 2004, Jun. 7-10, 2004, Cavtat, Croatia, pp. 323-328, which is incorporated herein by reference.

Operation 4104 illustrates measuring at least one of iris dilation or constriction, gaze tracking, skin response, or voice response. For example, as shown in FIGS. 32A through 33, brain activity surrogate marker measurer module 3348 may measure voice response of individual 134. In some instances, brain activity surrogate marker measurer module 3348 may include a computer processor and/or medical instrumentality, such as a stethoscope and/or a sphygmomanometer. In one embodiment, brain activity surrogate marker measurer module 3348 may record changes in the movement of an individual's iris (with corresponding changes in the size of the pupil) before, during, and/or after administration of a bioactive agent and/or an artificial sensory experience. Such measurements of physiologic activity that indicate brain activity and/or mental state may be carried out at a time that is proximate to administration of a bioactive agent and/or an artificial sensory experience.

In one embodiment, brain activity surrogate marker measurer module 3348 may measure and/or record gaze tracking. In some instances, brain activity surrogate marker measurer module 3348 may include a camera that can monitor a subject's eye movements in order to determine whether the subject looks at a presented characteristic, for example, during a certain time period. For example, a camera may include a smart camera that can capture images, process them and issue control commands within a millisecond time frame. Such smart cameras are commercially available (e.g., Hamamatsu's Intelligent Vision System; http://jp.hamamatsu.com/en/product_info/index.html). Such image capture systems may include dedicated processing elements for each pixel image sensor. Other camera systems may include, for example, a pair of infrared charge coupled device cameras to continuously monitor pupil size and position as a user watches a visual target moving forward and backward. This can provide real-time data relating to pupil accommodation relative to objects on, for example, a user interface 116 including a display. (e.g., http://jp.hamamatsu.com/en/rd/publication/scientific_american/common/pdf/scientific_0608.pdf).

Eye movement and/or iris movement may also be measured by video-based eye trackers. In these systems, a camera focuses on one or both eyes and records eye movement as the viewer looks at a stimulus. Contrast may be used to locate the center of the pupil, and infrared and near-infrared non-collumnated light may be used to create a corneal reflection. The vector between these two features can be used to compute gaze intersection with a surface after a calibration for an individual 134.

In one embodiment, brain activity surrogate marker measurer module 3348 may measure and/or record skin response. Brain activity may be determined by detection of a skin response associated with a stimulus. One skin response that may correlate with mental state and/or brain activity is galvanic skin response (GSR), also known as electrodermal response (EDR), psychogalvanic reflex (PGR), or skin conductance response (SCR). This is a change in the electrical resistance of the skin. There is a relationship between sympathetic nerve activity and emotional arousal, although one may not be able to identify the specific emotion being elicited. The GSR is highly sensitive to emotions in some people. Fear, anger, startle response, orienting response, and sexual feelings are all among the emotions which may produce similar GSR responses. GSR is typically measured using electrodes to measure skin electrical signals.

For example, an Ultimate Game study measured skin-conductance responses as a surrogate marker or autonomic index for affective state, and found higher skin conductance activity for unfair offers, and as with insular activation in the brain, this measure discriminated between acceptances and rejections of these offers. See Sanfey, "Social Decision-Making: Insights from Game Theory and Neuroscience," Science, vol. 318, pp. 598-601 (26 Oct. 2007), which is incorporated herein by reference. Other skin responses may include flushing, blushing, goose bumps, sweating, or the like.

In one embodiment, brain activity surrogate marker measurer module 3348 may measure and/or record voice response. Voice response may include speech captured by a microphone during presentation of a characteristic. Speech or voice can be measured, for example, by examining voice, song, and/or other vocal utterances of a subject before, during, and/or after administration of a bioactive agent and/or an artificial sensory experience to an individual 134. Such measurements may include, for example, as discussed above, layered voice analysis, voice stress analysis, or the like.

The reaction of an individual to an administered bioactive agent and/or an artificial sensory experience, such as an event in a virtual world may be a recognizable vocal exclamation such as "Wow, that's nice!" that may be detectable by a brain activity surrogate marker measurer module 3348, such as a microphone monitoring the subject while being administered an artificial sensory experience. A brain activity surrogate marker measurer module 3348 may include a voice response module and/or a speech recognition function, such as a software program or computational device, that can identify and/or record an utterance of a subject as speech or voice data.

Operation 4106 illustrates assigning an artificial sensory experience to measure at least one effect of the bioactive agent in at least one of near real time or real time. For example, as shown in FIGS. 32A through 33, near real time measurer module 3350 may assign an artificial sensory experience to measure an effect of the bioactive agent in near real time. A near real time event may include the current time of an event plus processing time. In one embodiment, near real time measurer module 3350 may assign a virtual world, such as World of Warcraft, to measure a bioactive agent effect in near real time. A further example of measuring real time, including real-time medical alerting, may be found in McGovern, U.S. Pat. No. 6,909,359, which is incorporated herein by reference. In some instances, near real time measurer module 3350 may include a computer processor.

Figure 42:
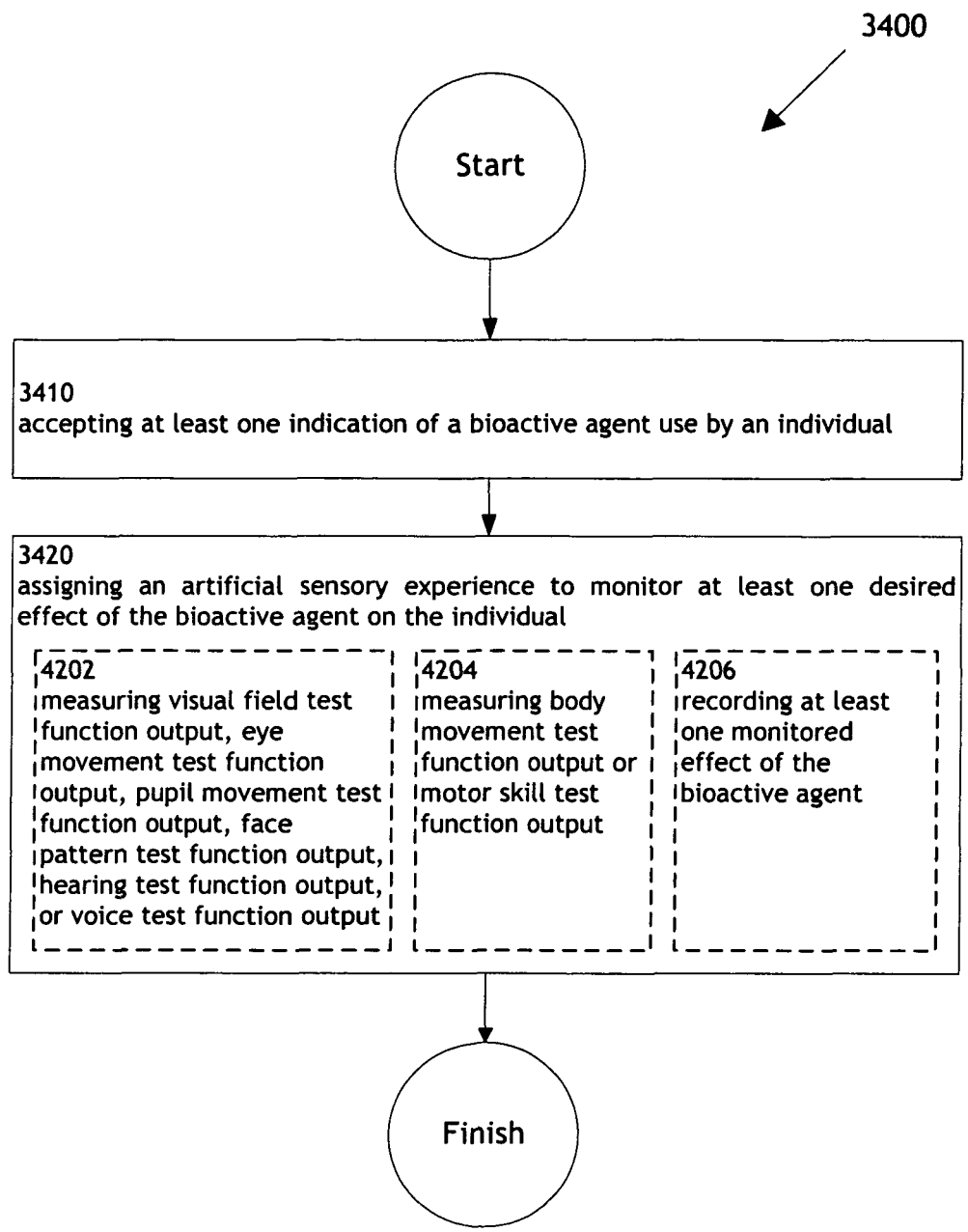
FIG. 42 illustrates an alternative embodiment of the operational flow of FIG. 34.

FIG. 42 illustrates alternative embodiments of the example operational flow 3400 of FIG. 34. FIG. 42 illustrates example embodiments where the operation 3420 may include at least one additional operation. Additional operations may include an operation 4202, an operation 4204, and/or an operation 4206.

Operation 4202 illustrates measuring visual field test function output, eye movement test function output, pupil movement test function output, face pattern test function output, hearing test function output, or voice test function output. For example, as shown in FIGS. 32A through 33, test function output measurer module 3352 may measure a visual field test function output. For example, an individual 134 may undertake a visual field test, for example, on a personal computer so as to obtain visual field test data. A visual field test function may include, for example, one or more visual field test functions, one or more pointing device manipulation test functions, and/or one more reading test functions. Visual field attributes are indicators of an individual's ability to see directly ahead and peripherally. An example of a visual field test function may be a measure of an individual's gross visual acuity, for example using a Snellen eye chart or visual equivalent on a display. Alternatively, a campimeter may be used to conduct a visual field test. Such visual field tests or campimeters are available online (e.g., at http://www.testvision.org/what_is.htm). Visual field testing could be done in the context of, for example, new email alerts that require clicking and that appear in various locations on a display. Based upon the location of decreased visual field, the defect can be localized, for example in a quadrant system.

In an embodiment, test function output measurer module 3352 may measure eye movement test function output. An eye movement test function or a pupil movement test function may include, for example, one or more eye movement test functions, one more pupil movement test functions, and/or one or more pointing device manipulation test functions. An example of an eye movement test function may be a measurement of an individual's ability to follow a target on a display with her eyes throughout a 360° range. Such testing may be done in the context of an individual experiencing an artificial sensory experience or participating in a virtual world. In such examples, eye movement test function output may be obtained through a camera in place as a monitoring device that can monitor the eye movements of the individual during interaction with administration of the artificial sensory experience and/or the bioactive agent. Another example of an eye movement test function may include eye tracking data from an individual monitoring device, such as a video communication device, for example, when a task requires tracking objects on a display, reading, or during resting states between activities in an application. A further example includes pupil movement tracking data from the individual 134 at rest or during an activity required by an application or user-health test function.

In an embodiment, test function output measurer module 3352 may measure pupil movement test function output. An example of a pupil movement test function may be a measure of an individual's pupils when exposed to light or objects at various distances. A pupillary movement test may assess the size and symmetry of an individual's pupils before and after a stimulus, such as light or focal point. In the above embodiments, altered eye movement ability and/or pupil movement ability may indicate and/or monitor a desired effect of an administered bioactive agent.

In an embodiment, test function output measurer module 3352 may measure face pattern test function output. A face pattern test function may include, for example, one or more face movement test functions involving an individual's ability to move the muscles of the face. An example of a face pattern test function may be a comparison of an individual's face while at rest, specifically looking for nasolabial fold flattening or drooping of the corner of the mouth, with the individual's face while moving certain facial features. The individual may be asked to raise her eyebrows, wrinkle her forehead, show her teeth, puff out her cheeks, or close her eyes tight. Such testing may be done via facial pattern recognition software used in conjunction with, for example, an artificial sensory experience. Abnormalities in facial expression or pattern may indicate efficacy of and/or a desired effect of a bioactive agent while experiencing an artificial sensory experience.

In one embodiment, test function output measurer module 3352 may measure measuring hearing test function output. A hearing test function may include, for example, one or more conversation hearing test functions such as one or more tests of an individual's ability to detect conversation, for example in a virtual world and/or an artificial sensory experience scenario. An example of a hearing test function may include a gross hearing assessment of an individual's ability to hear sounds. This may be done by simply presenting sounds to the individual or determining if the individual can hear sounds presented to each of the ears. For example, at least one hearing test device may vary volume settings or sound frequency over time to test an individual's hearing. For example, a mobile phone device or other communication device may carry out various hearing test functions. Altered hearing ability may indicate efficacy of and/or a desired effect of a bioactive agent while experiencing an artificial sensory experience.

In one embodiment, test function output measurer module 3352 may measure measuring hearing test function output. A voice test function may include, for example, one or more voice test functions. An example of a voice test function may be a measure of symmetrical elevation of the palate when the user says "aah" or a test of the gag reflex. A voice test function may monitor user voice frequency or volume data during, for example, gaming, such as a virtual world, an artificial sensory experience, videoconferencing, speech recognition software use, or mobile phone use. A voice test function may assess an individual's ability to make simple sounds or to say words, for example, consistently with an established voice pattern for the individual. An abnormal or altered voice may indicate efficacy of and/or a desired effect of a bioactive agent while experiencing an artificial sensory experience.

In some instances, test function output measurer module 3352 may include a computer processor and/or medical instrumentality, such as that described in the above paragraphs. One skilled in the art may select, establish or determine an appropriate pupil movement test function for monitoring a desired bioactive agent effect. Test function sets and test functions may be chosen by one skilled in the art based on knowledge, direct experience, or using available resources such as websites, textbooks, journal articles, or the like. An example of a relevant website can be found in the online Merck Manual at http://www.merck.com/mmhe/sec06/ch077/ch077c.htmt#tb077_1. Examples of relevant textbooks include Patten, J. P., "Neurological Differential Diagnosis," Second Ed., Springer-Verlag, London, 2005; Kasper, Braunwald, Fauci, Hauser, Longo, and Jameson, "Harrison's Principles of Internal Medicine," 16th Ed., McGraw-Hill, New York, 2005; Greenberg, M. S., "Handbook of Neurosurgery," 6th Ed., Thieme, Lakeland, 2006; and Victor, M., and Ropper, A. H., "Adams and Victor's Principles of Neurology," 7th Ed., McGraw-Hill, New York, 2001.

Operation 4204 illustrates measuring body movement test function output or motor skill test function output. For example, as shown in FIGS. 32A through 33, test function output measurer module 3352 may measure body movement test function output or motor skill test function output. An example of a body movement test function may include prompting an individual 134 to activate or click a specific area on a display to test, for example, arm movement, hand movement, or other body movement or motor skill function. Another example is visual tracking of an individual's body, for example during an artificial sensory experience, wherein changes in facial movement, limb movement, or other body movements are detectable. A further example is testing an individual's ability to move while using a game controller in an artificial sensory experience containing an accelerometer, for example, the Wii remote that is used for transmitting an individual's movement data to a computing device. A body movement test function may perform gait analysis, for example, in the context of video monitoring of the user. A body movement test function may also include a test function of fine movements of the hands and feet. Rapid alternating movements, such as wiping one palm alternately with the palm and dorsum of the other hand, may be tested as well. A common test of coordination is the finger-nose-finger test, in which the user is asked to alternately touch their nose and an examiner's finger as quickly as possible. Alternatively, testing of fine movements of the hands may be tested by measuring an individual's ability to make fine movements of a cursor on a display. To test the accuracy of movements in a way that requires very little strength, an individual may be prompted to repeatedly touch a line drawn on the crease of the individual's thumb with the tip of their forefinger; alternatively, an individual may be prompted to repeatedly touch an object on a touchscreen display. Abnormalities and/or alterations of body movement may indicate the efficacy of and/or a desired effect of a bioactive agent while experiencing an artificial sensory experience.

A motor skill test function may include, for example, one or more deliberate body movement test functions such as one or more tests of an individual's ability to move an object, including objects on a display, e.g., a cursor. An example of a motor skill test function may be a measure of an individual's ability to perform a physical task. A motor skill test function may measure, for example, an individual's ability to traverse a path on a display in straight line with a pointing device, to type a certain sequence of characters without error, or to type a certain number of characters without repetition. For example, a slowed cursor on a display may indicate a desired effect of a bioactive medication, such as an antianxiety medication. An antianxiety medication may work to calm an individual resulting in a slowed response time and a slowed cursor on a display and indicating a desired effect of a bioactive agent. Alternatively, an individual may be prompted to switch tasks, for example, to alternately type some characters using a keyboard and click on some target with a mouse. If a user has a motor skill deficiency, she may have difficulty stopping one task and starting the other task indicating a desired effect of a bioactive agent during an artificial sensory experience. In some instances, test function output measurer module 3352 may include a computer processor, computer equipment, such as a touch screen display, and/or medical instrumentality, such as that described in the above paragraphs.

Operation 4206 illustrates recording at least one monitored effect of the bioactive agent. For example, as shown in FIGS. 32A through 33, effect recorder module 3354 may record at least one monitored effect of the bioactive agent. Recording a monitored effect may include capturing data including the monitored effect to a record, or a format stored on a storage medium. In one embodiment, effect recorder module 3354 may record body movement test function output onto a hard disk drive. Other examples of a record and/or storage medium may include flash memory devices, a tape drive, circuitry with non-volatile and/or volatile RAM, an optical disc, for example a CD and/or DVD, and/or a paper record, such as a collection of printed spreadsheets and/or other lists of data. In an additional embodiment, effect recorder module 3354 may record a monitored effect by utilizing data acquisition software. Further discussion of data acquisition may be found in Green, T. et al., *PC-Based Medical Data Acquisition and Analysis, cbms*, p. 0159, EIGHTH IEEE SYMPOSIUM ON COMPUTER-BASED MEDICAL SYSTEMS (CBMS '95), 1995, which is incorporated herein by reference. In some instances, effect recorder module 3354 may include a computer processor and/or other data logging instrumentation, such as NI CompactDAQ hardware, available from National Instruments, Austin, Tex. (http://www.ni.com/dataacquisition/compact-daq/).

Figure 43:
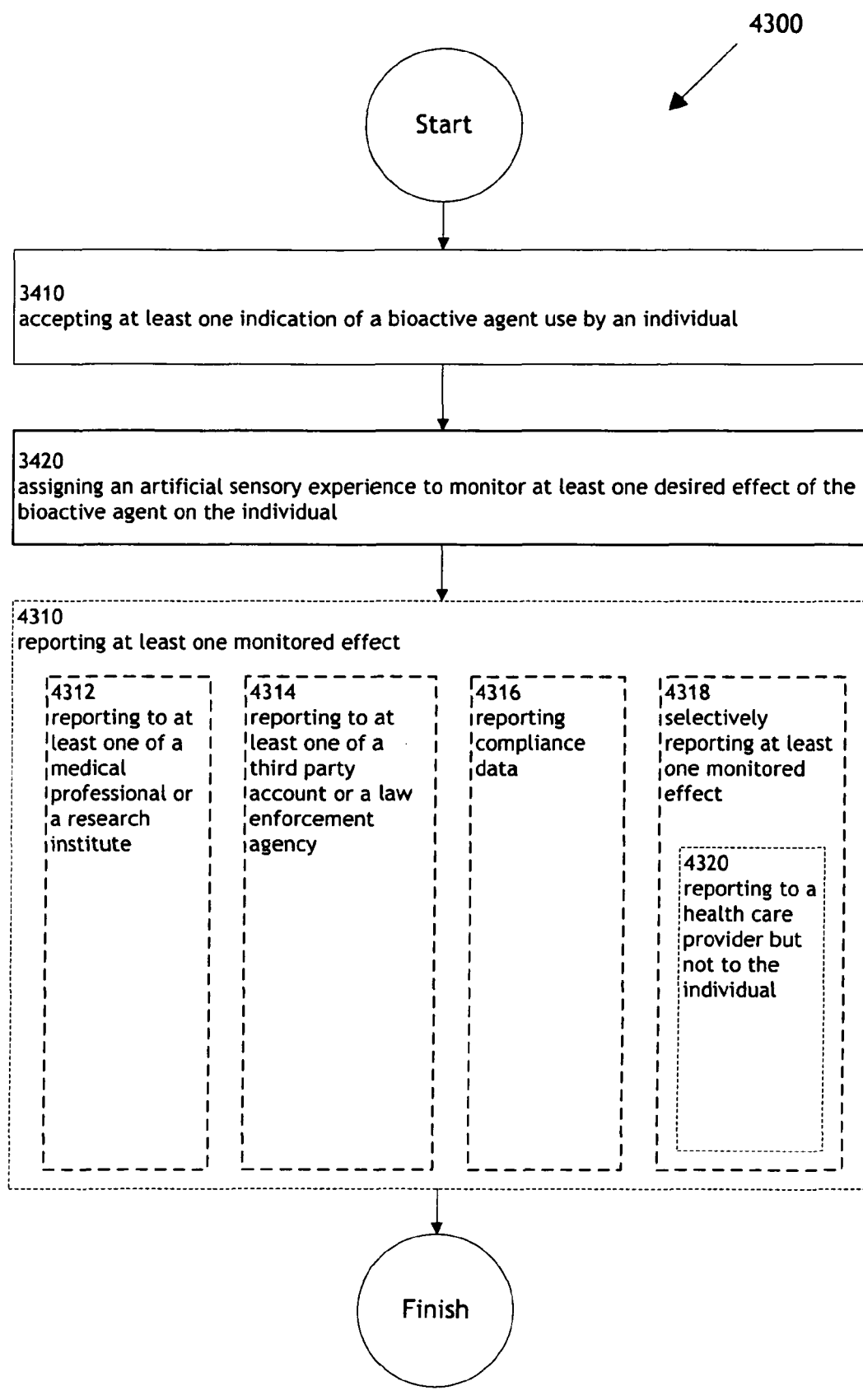
FIG. 43 illustrates an alternative embodiment of the operational flow of FIG. 34.

FIG. 43 illustrates an operational flow 4300 representing example operations related to accepting at least one indication of a bioactive agent use by an individual; assigning an artificial sensory experience to monitor at least one desired effect of the bioactive agent on the individual; and reporting at least one monitored effect. FIG. 43 illustrates an example embodiment where the example operational flow 3400 of FIG. 34 may include at least one additional operation. Additional operations may include an operation 4310, an operation 4312, an operation 4314, an operation 4316, an operation 4318, and/or an operation 4320.

After a start operation, operation 3410, and operation 3420, the operational flow 4300 moves to operation 4310. Operation 4310 illustrates reporting at least one monitored effect. For example, as shown in FIGS. 32A through 33, reporter module 3356 may report at least one monitored effect. Reporting may include relating or passing on information, and/or describing a monitored effect status. In one embodiment, reporter module 3356 may report acquired data including a monitored effect of an antidepressant, such as a heart rate, while an individual 134 is experiencing an artificial sensory experience, such as the social networking site MySpace with a brightened lighting scheme. In this embodiment, acquired data including an increased heart rate may be reported to a medical professional administering the artificial sensory experience to the individual 134 by giving the acquired data in the form of a CD. One example regarding a clinical information reporting system may be found in Selker, U.S. Pat. No. 5,277,188, which is incorporated herein by reference. In some instances, reporter module 3356 may include a computer processor.

Operation 4312 illustrates reporting to at least one of a medical professional or a research institution. For example, as shown in FIGS. 32A through 33, third party reporter module 3360 may report a monitored effect to a medical professional, such as a family physician. A medical professional may include at least one person, agency, department, unit, subcontractor, and/or other entity that delivers a health-related service. Some examples of a medical professional may include a physician, a nurse, a psychiatrist, a clinical social worker, a clinical psychologist, support staff, a pharmacist, a therapist, a hospital, and/or a medical insurance professional. In another embodiment, third party reporter module 3360 may report to a research institution. A research institution may include a research laboratory, an academic institution, a private research institution, and/or a commercial entity. Some examples of a research institution may include Oregon Health & Science University (OHSU), Bell Laboratories, SRI International, Boston Biomedical Research Institute (BBRI), and/or the National Institutes of Health (NIH). In one embodiment, data may be reported to a health clinic, which is further discussed in Selker, U.S. Pat. No. 5,277,188. In some instances, third party reporter module 3360 may include a computer processor and/or a communications link.

Operation 4314 illustrates reporting to at least one of a third party account or a law enforcement agency. For example, as shown in FIGS. 32A through 33, third party reporter module 3360 may report to a third party account. A third party may include a person, organization, and/or entity not actively involved in the current method. A third party account may include, for example, an account granting access to a third party by inputting a user name, password, and/or some other identifying information, such as an account number. Some examples of a third party account may include a gaming account, such as a World of Warcraft account, a website account, such as a personal and/or secured website where data may be uploaded or accessed, and/or an account on a networked computer, such as a ftp server account. In one specific embodiment, third party reporter module 3360 may report acquired data, such as at least one monitored effect of an antianxiety medication, to a World of Warcraft account, which in turn, for example, may be configured to modify an element of an artificial sensory experience.

In another embodiment, third party reporter module 3360 may report to a law enforcement agency, such as the Federal Bureau of Investigation (FBI). A law enforcement agency may include an agency and/or agency representative directly and/or indirectly responsible for enforcing the law of a governing body. Some examples of law enforcement agencies may include the Federal Bureau of Investigation (FBI), the New York City Police Department, the Drug Enforcement Administration (DEA), a county sheriff's department and/or a local police detective. In some instances, third party reporter module 3360 may include a computer processor and/or a communications link.

Operation 4316 illustrates reporting compliance data. For example, as shown in FIGS. 32A through 33, compliance data reporter module 3362 may report compliance data. Compliance data may include data demonstrating adherence to a standard or a regulation, such as, for example, compliance to a physician's prescription. In one embodiment, compliance data reporter module 3362 may report whether individual 134 has complied with a physician's prescription to take an antidepressant by correlating the amount of activity in an artificial sensory experience, such as an amount of avatar interaction by individual 134 in the virtual world Second Life, with efficacy of the antidepressant. In the current embodiment, a decreased amount of activity by individual 134 in Second Life may indicate noncompliance with the physician's prescription based on a tendency to be less active socially when depressed. The data, including the indication of noncompliance, may be then reported to an interested party. In some instances, compliance data reporter module 3362 may include a computer processor.

Operation 4318 illustrates selectively reporting at least one monitored effect. For example, as shown in FIGS. 32A through 33, selective reporter module 3370 may selectively report at least one monitored effect. Selective reporting may include limiting and/or blocking access of monitoring results to a specific party. For example, selective reporter module 3370 may report to a physician and not report to the individual 134. Selective reporter module 3370, for example, may report to only a third party. In another example, selective reporter module 3370 may report results only to individual 134. In one embodiment, selective reporter module 3370 may report to a law enforcement agency but not to an individual 134 data indicating the use of an illegal substance. In some instances, selective reporter module 3370 may include a computer processor.

Operation 4320 illustrates reporting to a health care provider but not to the individual. For example, as shown in FIGS. 32A through 33, selective reporter module 3370 may report to a health care provider but not to the individual. A health care provider may include a hospital, a doctor, a nurse, a medical clinic, a dentist, and/or any provider of preventive, diagnostic, therapeutic, rehabilitative, maintenance, or palliative care and/or counseling. Additionally, a healthcare provider may include a seller and/or dispenser of prescription drugs or medical devices. In one embodiment, selective reporter module 3370 may report to a physician and a hospital results from administering an antidepressant to an individual 134, assigning time spent on a social networking website, and monitoring the intensity of a desired effect of the bioactive agent on the individual 134, such as an increased disposition. In the current embodiment, an increased disposition may indicate that an antidepressant medication is effective when coupled with the social networking website. In some instances, compliance data reporter module 3362 may include a computer processor.

Figure 44:
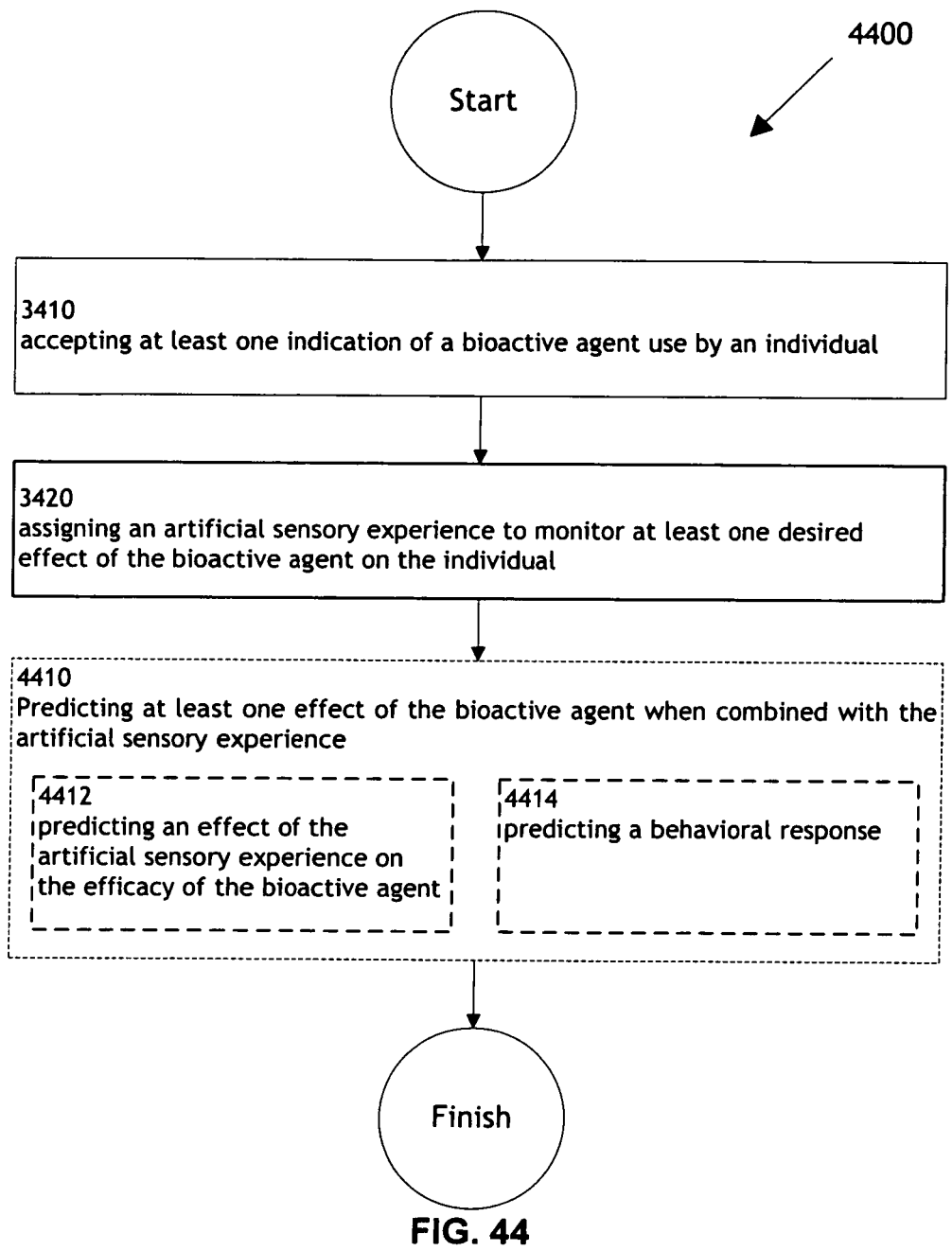
FIG. 44 illustrates an alternative embodiment of the operational flow of FIG. 34.

FIG. 44 illustrates an operational flow 4400 representing example operations related to accepting at least one indication of a bioactive agent use by an individual; assigning an artificial sensory experience to monitor at least one desired effect of the bioactive agent on the individual; and predicting at least one effect of the bioactive agent when combined with the artificial sensory experience. FIG. 44 illustrates an example embodiment where the example operational flow 3400 of FIG. 34 may include at least one additional operation. Additional operations may include an operation 4410, an operation 4412, and/or an operation 4414.

After a start operation, operation 3410, and operation 3420, the operational flow 4400 moves to operation 4410. Operation 4410 illustrates predicting at least one effect of the bioactive agent when combined with the artificial sensory experience. For example, as shown in FIGS. 32A through 33, predictor module 3364 may predict an effect of the bioactive agent, such as a higher Wii game score after being administered an antidepressant medication, when combined with the artificial sensory experience, such as a Wii sports game. Predicting an effect may, for example, include utilizing a mathematical model, prediction software, an algorithm, and/or a statistical model. In one embodiment, predictor module 3364 may predict a decrease in activity in an artificial sensory experience, such as troll-killing in World of Warcraft, when an individual 134 is administered a bioactive agent, such as an antianxiety medication. In the current embodiment, predictor module 3364 may arrive at a certain prediction by utilizing empirical data and comparing the empirical data with characteristics of the individual 134. Other examples of prediction may be found in Jokiniitty, J. M. et al., *Prediction of blood pressure level and need for antihypertensive medication: 10 years of follow-up*, J HYPERTENSION, 19(7):1193-201 (2001); Yamada, K. et al., *Prediction of medication noncompliance in outpatients with schizophrenia: 2-year follow-up study*, PSYCHIATRY RESEARCH, 141(1):61-69 (2004); and Parker, G. et al., *Prediction of response to antidepressant medication by a sign-based index of melancholia*, AUSTRALIAN AND NEW ZEALAND JOURNAL OF PSYCHIATRY, 27(1):56-61 (1993); each being incorporated herein by reference. In some instances, predictor module 3364 may include a computer processor.

Operation 4412 illustrates predicting an effect of the artificial sensory experience on the efficacy of the bioactive agent. For example, as shown in FIGS. 32A through 33, effect predictor module 3366 may predict an effect of the artificial sensory experience, such as a background color modification and the addition of calming music, on the efficacy of the bioactive agent. In one embodiment, effect predictor module 3366 may predict that the addition of uptempo music and bright background colors to a social networking website enhances the efficacy of an antidepressant. Effect predictor module 3366 may predict whether an artificial sensory experiment effect improves and/or decreases a bioactive agent efficacy by utilizing and comparing empirical data and characteristics of an individual 134, as described above. Further discussion of music effects may be found in Schellenberg, E. G. et al., *Exposure to music and cognitive performance: tests of children and adults*, PSYCHOLOGY OF MUSIC, Vol. 35, No. 1, 5-19 (2007), incorporated herein by reference. Discussion regarding the effects of color and/or light on nonvisual psychological processes may be found in Knez, *Effects of colour of light on nonvisual psychological processes*, JOUR- NAL OF ENVIRONMENTAL PSYCHOLOGY, 21 (2):201-208 (2001); M. R Basso Jr., *Neurobiological relationships between ambient lighting and the startle response to acoustic stress in humans*, INT J NEUROSCI., 110(3-4):147-57 (2001), and Lam et al., *The Can-SAD Study: a randomized controlled trial of the effectiveness of light therapy and fluoxetine in patients with winter seasonal affective disorder*, AMERICAN JOURNAL OF PSYCHIATRY, 163(5):805-12 (2006), each incorporated by reference.

Other methods for predicting an effect of the artificial sensory experience on the efficacy of the bioactive agent may include trend estimation, regression analysis, and or data extrapolation. In one embodiment, effect predictor module 3366 may utilize trend estimation to predict an effect of the artificial sensory experience, such as a snowy environment in a virtual world, on the efficacy of the bioactive agent, such as an analgesic. Trend estimation may include the application of statistics to make predictions about trends in data using previously measured data utilizing methods which may include, for example, the method of least squares, an R-squared fit, and a trend plus noise method. An additional example may be found in Greenland, S. et al., *Methods for Trend Estimation from Summarized Dose-Response Data, with Applications to Meta-Analysis*, AM. J. EPIDEMIOL., 135(11):1301-09 (1992), which is incorporated herein by reference.

In another embodiment, effect predictor module 3366 may utilize regression analysis to predict an effect of the artificial sensory experience, such as a snowy environment in a virtual world, on the efficacy of the bioactive agent, such as an analgesic. Regression analysis may include statistical technique for determining the best mathematical expression describing the functional relationship between one response, such as efficacy of the bioactive agent, and one or more independent variables, for example, an effect of the artificial sensory experience. A further discussion of regression analysis may be found in Matthews D. E. and Farewell V. T., *Using and Understanding Medical Statistics*, Basel, S. Karger A. G., 2007, which is incorporated herein by reference.

In another embodiment, effect predictor module 3366 may utilize data extrapolation to predict an effect of the artificial sensory experience, such as a snowy environment in a virtual world, on the efficacy of the bioactive agent, for example an analgesic. Data extrapolation may include the process of constructing new data points outside a discrete set of known data points. For example, a bioagent's efficacy may be predicted by using and/or comparing previous measurements of an artificial sensory experience effect on a bioagent's efficacy using a population with similar characteristics as individual 134. One example using a data extrapolation algorithm may be found in Smith, M. R., et al., *A data extrapolation algorithm using a complex domain neuralnetwork*, IEEE TRANSACTIONS ON CIRCUITS AND SYSTEMS II: ANALOG AND DIGITAL SIGNAL PROCESSING, 44(2):143-47 (1997), which is incorporated herein by reference. In some instances, effect predictor module 3366 may include a computer processor.

Operation 4414 illustrates predicting a behavioral response. For example, as shown in FIGS. 32A through 33, behavioral response predictor module 3368 may predict a behavioral response. In one embodiment, behavioral response predictor module 3368 may predict an increased score in an artificial sensory experience, such as a Wii Sports game, when an individual is administered an antidepressant. In this embodiment, the administration of an antidepressant may serve to heighten the mood of an individual 134 and increase a desire to be competitive while experiencing an artificial sensory experience. Behavioral response predictor module 3368 may predict using methods described above, such as using empirical data and regression analysis, trend estimation, and or data extrapolation. Other examples of a behavioral response may include a lack of ability to concentrate while experiencing acute stress and/or flinching when exposed to a loud sound and/or loud acoustics. In some instances, behavioral response predictor module 3368 may include a computer processor.

Figure 45:
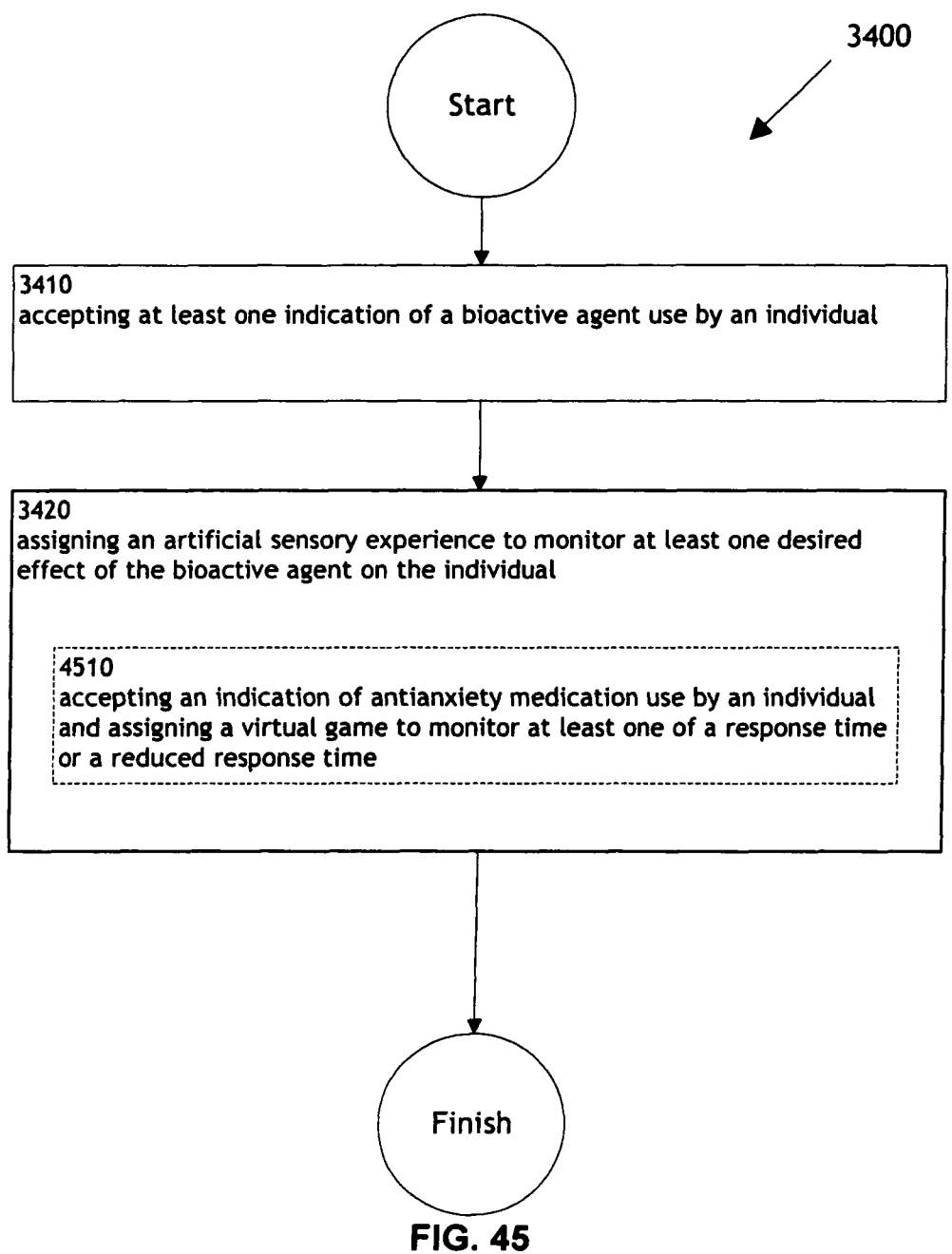
FIG. 45 illustrates an alternative embodiment of the operational flow of FIG. 34.

FIG. 45 illustrates an operational flow 3400 representing example operations related to accepting at least one indication of a bioactive agent use by an individual and assigning an artificial sensory experience to monitor at least one desired effect of the bioactive agent on the individual. FIG. 45 illustrates an example embodiment where the example operational flow 3400 of FIG. 34 may include at least one additional operation. Additional operations may include an operation 4510.

After a start operation, the operational flow 3400 moves to operation 4510. Operation 4510 illustrates accepting an indication of antianxiety medication use by an individual and assigning a virtual game to monitor at least one of a response time or a reduced response time. For example, as shown in FIGS. 32A through 33, accepter module 102 and assigner module 3334 may accept an indication of antianxiety medication use by an individual, such as an input from a physician indicating the antianxiety medication has been administered and is bioactive, and assign a virtual game, such as World of Warcraft, to monitor a response time by comparing and/or analyzing an amount of activity by the individual's avatar (e.g. troll killing). In some instances, accepter module 102 and/or assigner module 3334 may include a computer processor.

Figure 46:
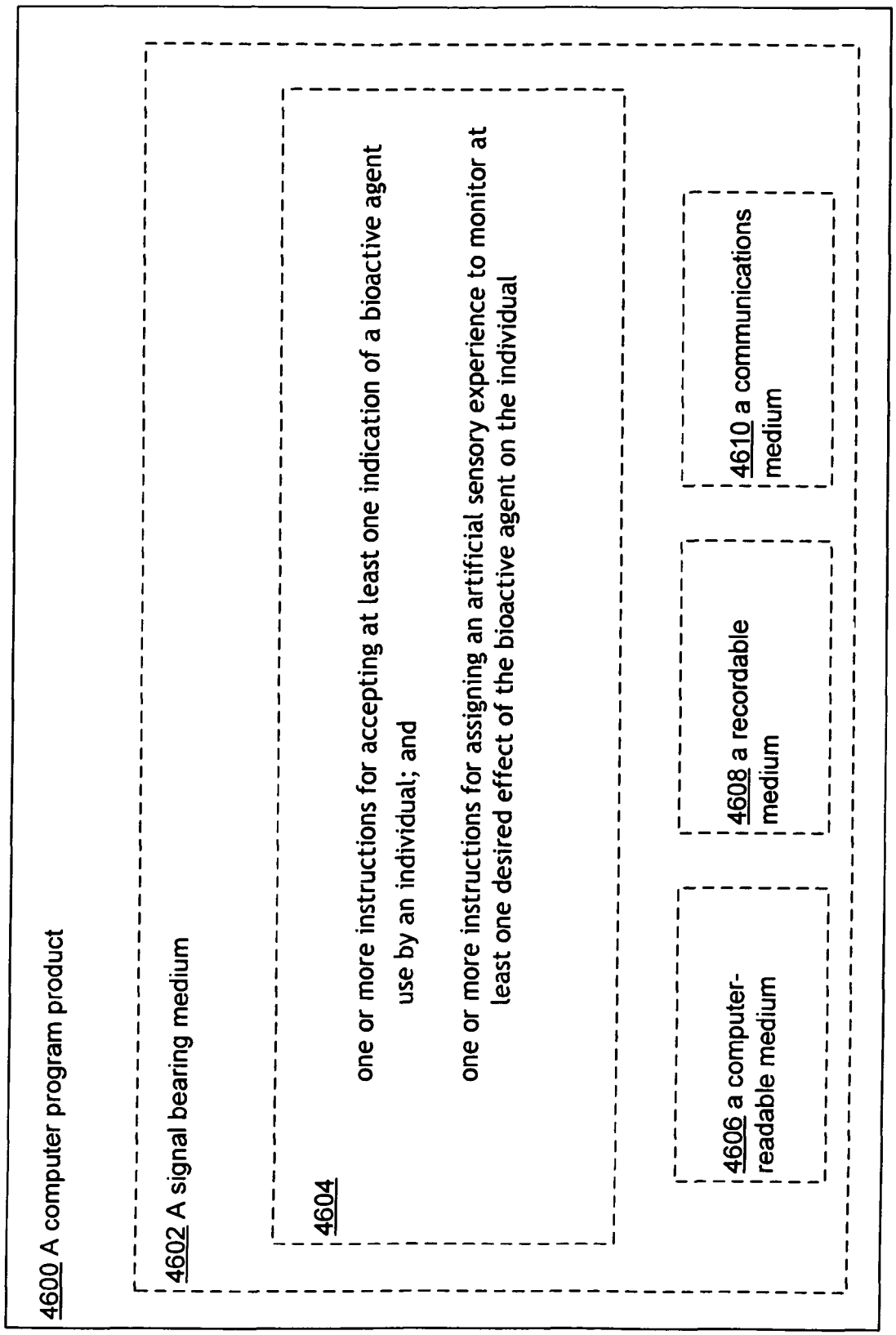
FIG. 46 illustrates a computer program product related to assigning an artificial sensory experience to monitor at least one desired effect of a bioactive agent.

FIG. 46 illustrates a partial view of an example computer program product 4600 that includes a computer program 4604 for executing a computer process on a computing device. An embodiment of the example computer program product 4600 is provided using a signal-bearing medium bearing 4602, and may include one or more instructions for accepting at least one indication of a bioactive agent use by an individual and one or more instructions for assigning an artificial sensory experience to monitor at least one desired effect of the bioactive agent on the individual. The one or more instructions may be, for example, computer executable and/or logic-implemented instructions. In one implementation, the signal-bearing medium 4602 may include a computer-readable medium 4606. In one implementation, the signal bearing medium 4602 may include a recordable medium 4608. In one implementation, the signal bearing medium 4602 may include a communications medium 4610.

Figure 47:
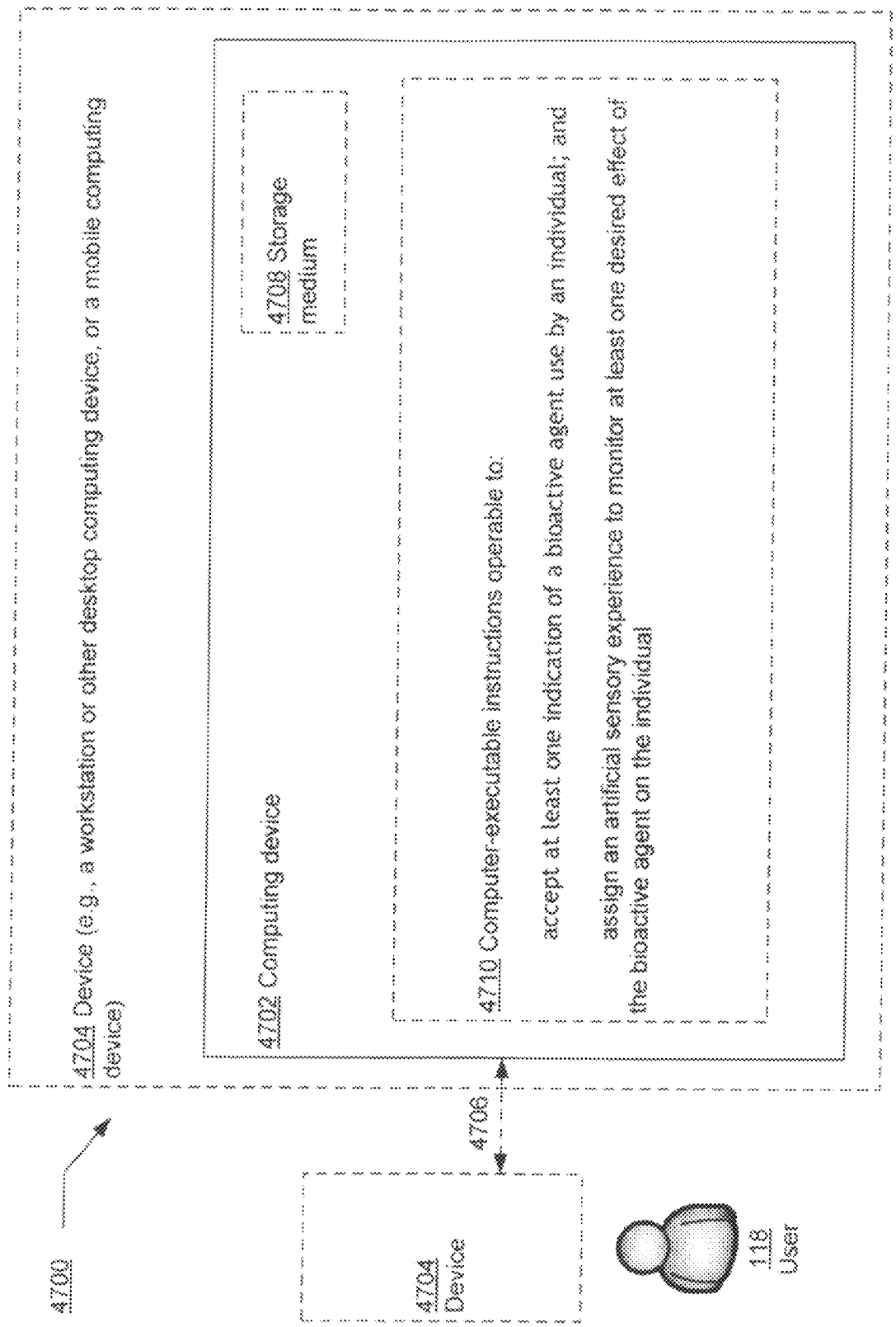
FIG. 47 illustrates a system related to assigning an artificial sensory experience to monitor at least one desired effect of a bioactive agent.

FIG. 47 illustrates an example system 4700 in which embodiments may be implemented. The system 4700 includes a computing system environment. The system 4700 also illustrates the user 118 using a device 4704, which is optionally shown as being in communication with a computing device 4702 by way of an optional coupling 4706. The optional coupling 4706 may represent a local, wide-area, or peer-to-peer network, or may represent a bus that is internal to a computing device (e.g., in example embodiments in which the computing device 4702 is contained in whole or in part within the device 4704). A storage medium 4708 may be any computer storage media.

The computing device 4702 includes computer-executable instructions 4710 that when executed on the computing device 4702 cause the computing device 4702 to accept at least one indication of bioactive agent use by an individual and assign an artificial sensory experience to monitor at least one desired effect of the bioactive agent on the individual. As referenced above and as shown in FIG. 47, in some examples, the computing device 4702 may optionally be contained in whole or in part within the device 4704.

In FIG. 47, then, the system 4700 includes at least one computing device (e.g., 4702 and/or 4704). The computer-executable instructions 4710 may be executed on one or more of the at least one computing device. For example, the computing device 4702 may implement the computer-executable instructions 4710 and output a result to (and/or receive data from) the computing device 4704. Since the computing device 4702 may be wholly or partially contained within the computing device 4704, the device 4704 also may be said to execute some or all of the computer-executable instructions 4710, in order to be caused to perform or implement, for example, various ones of the techniques described herein, or other techniques.

The device 4704 may include, for example, a portable computing device, workstation, or desktop computing device. In another example embodiment, the computing device 4702 is operable to communicate with the device 4704 associated with the user 118 to receive information about the input from the user 118 for performing data access and data processing and presenting an output of the user-health test function at least partly based on the user data.

Although a user 118 is shown/described herein as a single illustrated figure, those skilled in the art will appreciate that a user 118 may be representative of a human user, a robotic user (e.g., computational entity), and/or substantially any combination thereof (e.g., a user may be assisted by one or more robotic agents). In addition, a user 118, as set forth herein, although shown as a single entity may in fact be composed of two or more entities. Those skilled in the art will appreciate that, in general, the same may be said of "sender" and/or other entity-oriented terms as such terms are used herein.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also tends itself well to modular and/or object-oriented program design paradigms.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electromechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f)

a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although user 118 is shown/described herein as a single illustrated figure, those skilled in the art will appreciate that user 118 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent wilt be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system, comprising:
    an acceptor module configured to accept at least one indication of bioactive agent use by an individual;
    an assigner module configured to assign a virtual world to monitor at least one response time of the individual;
    an effect predictor module configured to predict at least one response time of the individual in the virtual world based at least in part on the indicated bioactive agent accepted by the acceptor module; and
    a reporter module configured to report the at least one response time predicted by the effect predictor module and at least one monitored response time in the virtual world assigned by the assigner module,
    wherein at least one of the acceptor module, the assigner module, the effect predictor module or the reporter module is at least partially implemented in computing hardware.

2. The system of claim 1, wherein the acceptor module configured to accept at least one indication of bioactive agent use by an individual comprises:
    a bioactive agent identification acceptor module configured to accept an identification of at least one bioactive agent prescribed for the individual.

3. The system of claim 1, wherein the acceptor module configured to accept at least one indication of bioactive agent use by an individual comprises:
    a substance abuse indication acceptor module configured to accept an indication of a substance subject to abuse used by the individual.

4. The system of claim 1, wherein the acceptor module configured to accept at least one indication of bioactive agent use by an individual comprises:
    a nutraceutical identification acceptor module configured to accept an indication of nutraceutical use by the individual.

5. The system of claim 1, wherein the assigner module configured to assign a virtual world to monitor at least one response time of the individual comprises:
    a sensate experience assigner module configured to assign a sensate experience.

6. The system of claim 5, wherein the sensate experience assigner module configured to assign a sensate experience comprises:
    a stimulus assessor module configured to assess at least one reaction to at least one of an olfactory stimulus, a haptic stimulus, a visual stimulus, an auditory stimulus, or a taste stimulus.

7. The system of claim 1, wherein the assigner module configured to assign a virtual world to monitor at least one response time of the individual comprises:
    an automated medical device receiver module configured to receive data from an automated medical device.

8. The system of claim 1, wherein the assigner module configured to assign a virtual world to monitor at least one response time of the individual comprises:
    an assigner module configured to assign at least one of a virtual world, a modification to a virtual world, a computer game, a modification to a computer game, a website, a modification to a website, an online course, or a modification to an online course.

9. The system of claim 1, wherein the assigner module configured to assign a virtual world to monitor at least one response time of the individual comprises:
    a monitorer module configured to monitor at least one of physical activity, body weight, body mass index, heart rate, blood oxygen level, or blood pressure temporally associated with an artificial sensory experience.

10. The system of claim 1, wherein the assigner module configured to assign a virtual world to monitor at least one response time of the individual comprises:
    a neurophysiological measurement monitorer module configured to monitor a neurophysiological measurement.

11. The system of claim 10, wherein the neurophysiological measurement monitorer module configured to monitor a neurophysiological measurement comprises:
    a physiologic activity measurer module configured to measure at least one physiologic activity using at least one of electroencephalography, computed axial tomography, positron emission tomography, magnetic resonance imaging, functional magnetic resonance imaging, functional near-infrared imaging, or magnetoencephalography.

12. The system of claim 1, wherein the assigner module configured to assign a virtual world to monitor at least one response time of the individual comprises:
    a brain activity surrogate marker measurer module configured to measure at least one brain activity surrogate marker.

13. The system of claim 1, wherein the assigner module configured to assign a virtual world to monitor at least one response time of the individual comprises:
    a near real time measurer module configured to assign an artificial sensory experience to measure at least one effect of the bioactive agent in at least one of near real time or real time.

14. The system of claim 1, wherein the assigner module configured to assign a virtual world to monitor at least one response time of the individual comprises:
    a test function output measurer module configured to measure at least one of visual field test function output, eye movement test function output, pupil movement test function output, face pattern test function output, hearing test function output, or voice test function output.

15. The system of claim 1, wherein the assigner module configured to assign a virtual world to monitor at least one response time of the individual comprises:

an effect recorder module configured to record at least one monitored effect of the bioactive agent.

16. The system of claim 1, further comprising:
an effect reporter module configured to report at least one monitored effect.

17. The system of claim 16, wherein the effect reporter module configured to report at least one monitored effect comprises:
a third party reporter module configured to report to at least one third party.

18. The system of claim 16, wherein the effect reporter module configured to report at least one monitored effect comprises:
a compliance data reporter module configured to report at least some compliance data.

19. The system of claim 16, wherein the effect reporter module configured to report at least one monitored effect comprises:
a selective reporter module configured to selectively report at least one monitored effect.

20. The system of claim 1, further comprising:
a predictor module configured to predict at least one effect of the bioactive agent.

21. The system of claim 20, wherein the predictor module configured to predict at least one effect of the bioactive agent comprises:
an effect predictor module configured to predict at least one effect of the virtual world on at least one efficacy of the bioactive agent.

22. The system of claim 20, wherein the predictor module configured to predict at least one effect of the bioactive agent comprises:
a behavioral response predictor module configured to predict at least one behavioral response.

23. The system of claim 1, wherein the acceptor module configured to accept at least one indication of bioactive agent use by an individual comprises:
an acceptor module configured to accept at least one indication of an effect associated with a bioactive agent.

24. The system of claim 1, wherein the effect predictor module configured to predict at least one response time of the individual in the virtual world based at least in part on the indicated bioactive agent accepted by the acceptor module comprises:
an effect predictor module associated with at least one of a mathematical model, prediction software, an algorithm, or a statistical model.

25. The system of claim 1, wherein the effect predictor module configured to predict at least one response time of the individual in the virtual world based at least in part on the indicated bioactive agent accepted by the acceptor module comprises:
an effect predictor module configured to utilize empirical data and compare the empirical data with characteristics of the individual.

26. The system of claim 1, wherein the effect predictor module configured to predict at least one response time of the individual in the virtual world based at least in part on the indicated bioactive agent accepted by the acceptor module comprises:
an effect predictor module associated with at least one of trend estimation, regression analysis, or data extrapolation.

* * * * *